(12) United States Patent
McCauley

(10) Patent No.: US 12,029,821 B2
(45) Date of Patent: Jul. 9, 2024

(54) EXTRACELLULAR VESICLES FOR INHALATION

(71) Applicant: OMNISPIRANT LIMITED, Clonmel (IE)

(72) Inventor: Gerard Bernard McCauley, Clonmel (IE)

(73) Assignee: OMNISPIRANT LIMITED, Clonmel (IE)

( * ) Notice: Subject to any disclaimer, the term of this patent is extended or adjusted under 35 U.S.C. 154(b) by 533 days.

(21) Appl. No.: 17/267,158

(22) PCT Filed: Aug. 9, 2019

(86) PCT No.: PCT/EP2019/071511
§ 371 (c)(1),
(2) Date: Feb. 9, 2021

(87) PCT Pub. No.: WO2020/030817
PCT Pub. Date: Feb. 13, 2020

(65) Prior Publication Data
US 2021/0308067 A1    Oct. 7, 2021

(30) Foreign Application Priority Data

Aug. 10, 2018  (EP) .................................... 18188591
Jan. 29, 2019  (EP) .................................... 19154302

(51) Int. Cl.
| | | |
|---|---|---|
| A61K 9/50 | (2006.01) | |
| A61K 9/00 | (2006.01) | |
| A61K 9/127 | (2006.01) | |
| A61K 48/00 | (2006.01) | |
| A61M 11/00 | (2006.01) | |
| A61P 11/00 | (2006.01) | |

(52) U.S. Cl.
CPC .......... *A61K 9/5068* (2013.01); *A61K 9/0078* (2013.01); *A61K 48/0091* (2013.01); *A61M 11/005* (2013.01); *A61P 11/00* (2018.01)

(58) Field of Classification Search
CPC ................ A61K 9/5068; A61K 9/0078; A61K 48/0091; A61K 9/1271; A61M 11/005; A61P 11/00
See application file for complete search history.

(56) References Cited

U.S. PATENT DOCUMENTS

| 9,901,600 B2 | 2/2018 | Mitsialis et al. | |
|---|---|---|---|
| 2015/0079046 A1 | 3/2015 | Sinden et al. | |
| 2018/0177727 A1* | 6/2018 | Kalluri .................... | A23L 23/10 |

FOREIGN PATENT DOCUMENTS

| AU | WO 2018112557 | * | 6/2018 |
|---|---|---|---|
| CN | 107625727 | * | 1/2018 |
| CN | 107625727 A | * | 1/2018 |
| WO | WO 2015/002956 A1 | | 1/2015 |
| WO | WO 2017/075708 A1 | | 5/2017 |

OTHER PUBLICATIONS

Kooijmans et al (PEGylated and targeted extracellular vesicles display enhanced cell specificity and circulation time), Journal of controlled release 224(2016) 77-85. (Year: 2016).*
International Search Report and Written Opinion for International Application No. PCT/EP2019/071511, dated Nov. 18, 2019, 11 pages.
Huckaby et al., "PEGylation for enhancing nanoparticle diffusion in mucus", Advanced Drug Delivery Reviews, 2017, vol. 124, No. 4, pp. 125-139.
Kim et al., "Engineering macrophage-derived exosomes for targeted paclitaxel delivery to pulmonary metastases: in vitro and in vivo evaluations", Nanomedicine: Nanotechnology, Biology and Medicine, 2018, vol. 14, No. 1, p. 195-204.
Kleemann et al., "Iloprost-containing liposomes for aerosol application in pulmonary arterial hypertension: formulation aspects and stability", Pharmaceutical research, 2007, vol. 24, No. 2, p. 277-287.
Kooijmans et al., "PEGylated and targeted extracellular vesicles display enhanced cell specificity and circulation time", J Control Release. 2016, vol. 224, pp. 77-85.
Zulueta et al., "Lung mesenchymal stem cells-derived extracellular vesicles attenuate the inflammatory profile of Cystic Fibrosis epithelial cells", Cellular Signalling, 2018, vol. 51, No. 1, pp. 110-118.
Endo-Takahashi et al., "Systemic delivery of miR-126 by miRNA-loaded Bubble liposomes for the treatment of hindlimb ischemia", Scientific Reports, vol. 4, No. 1, Jan. 24, 2014.

* cited by examiner

*Primary Examiner* — Mina Haghighatian
(74) *Attorney, Agent, or Firm* — FINNEGAN, HENDERSON, FARABOW, GARRETT & DUNNER LLP

(57) ABSTRACT

Vesicles, including exosomes, having a coating of a hydrophilic, neutral polymer such as PEG have an increased ability to form a suspension or colloid compared to uncoated vesicles. This enables the coated vesicles to be used to form aerosol droplets such that a liquid formulation containing vesicles can be used in a nebulizer for inhaled administration thereof. Such coated vesicles are also able to pass through mucus and can deliver their cargo into l

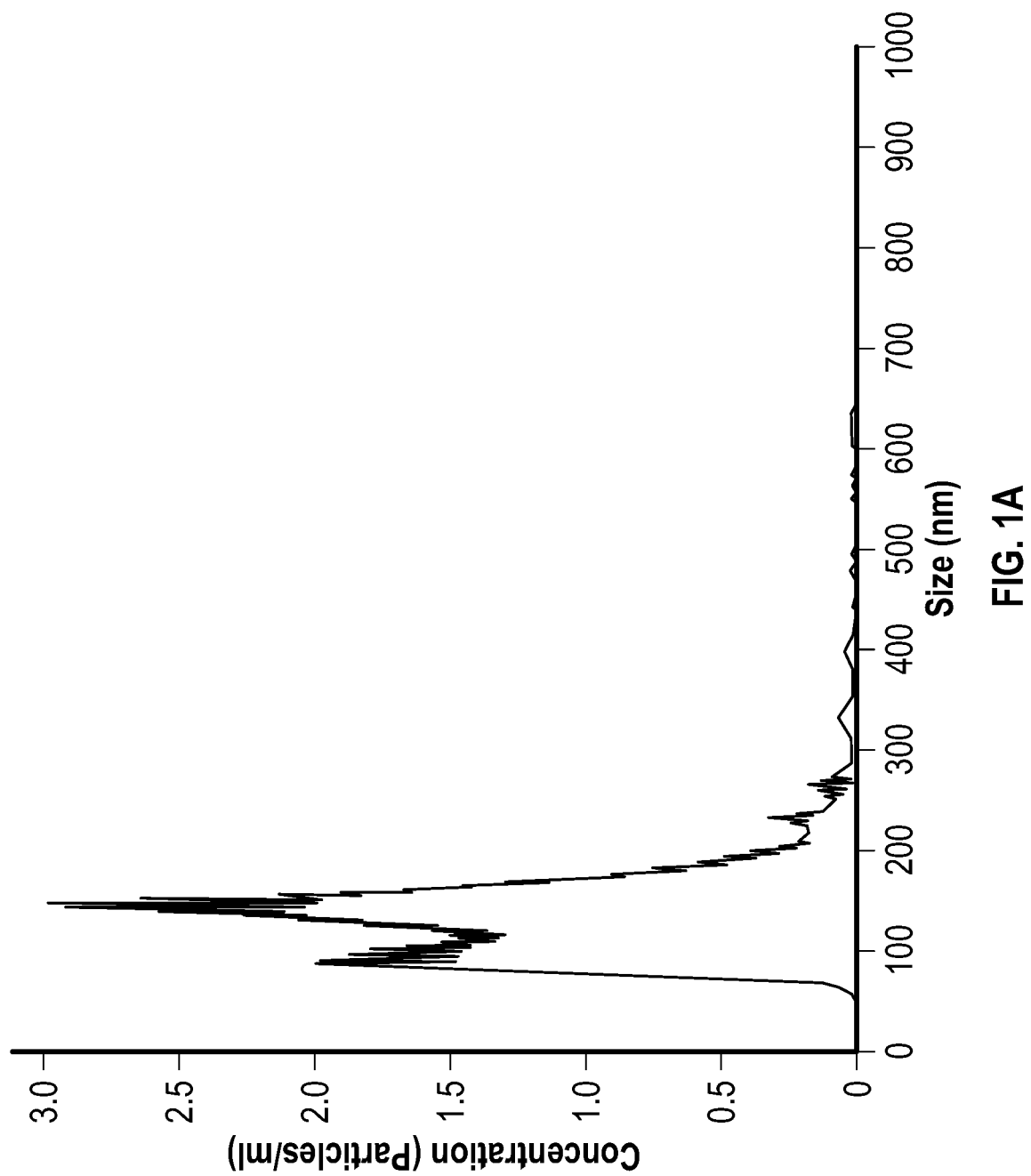

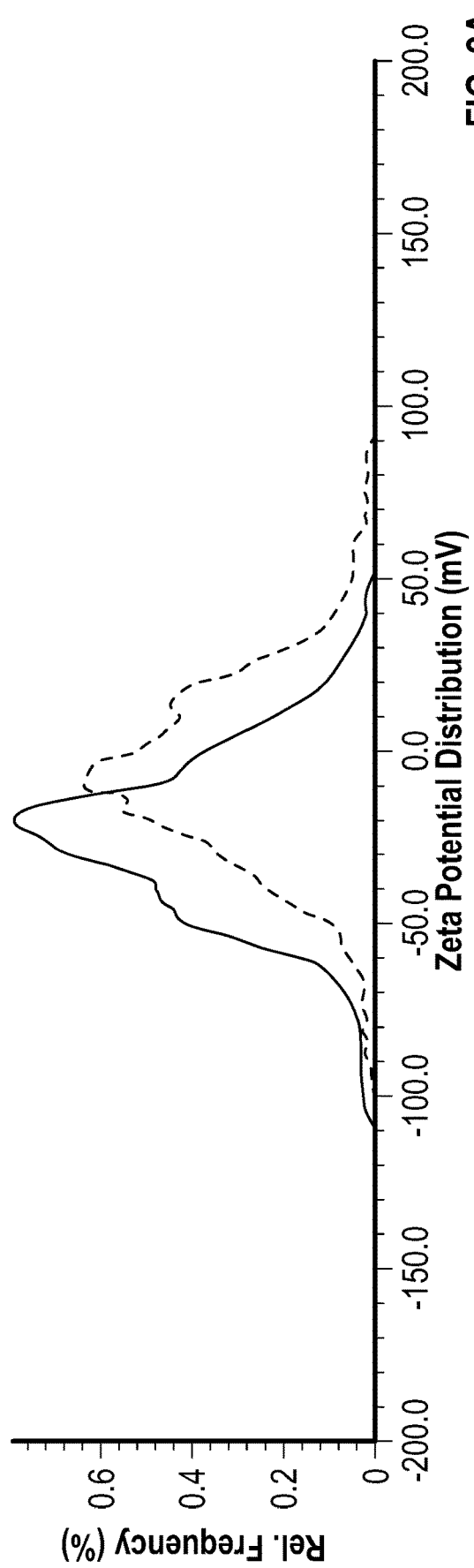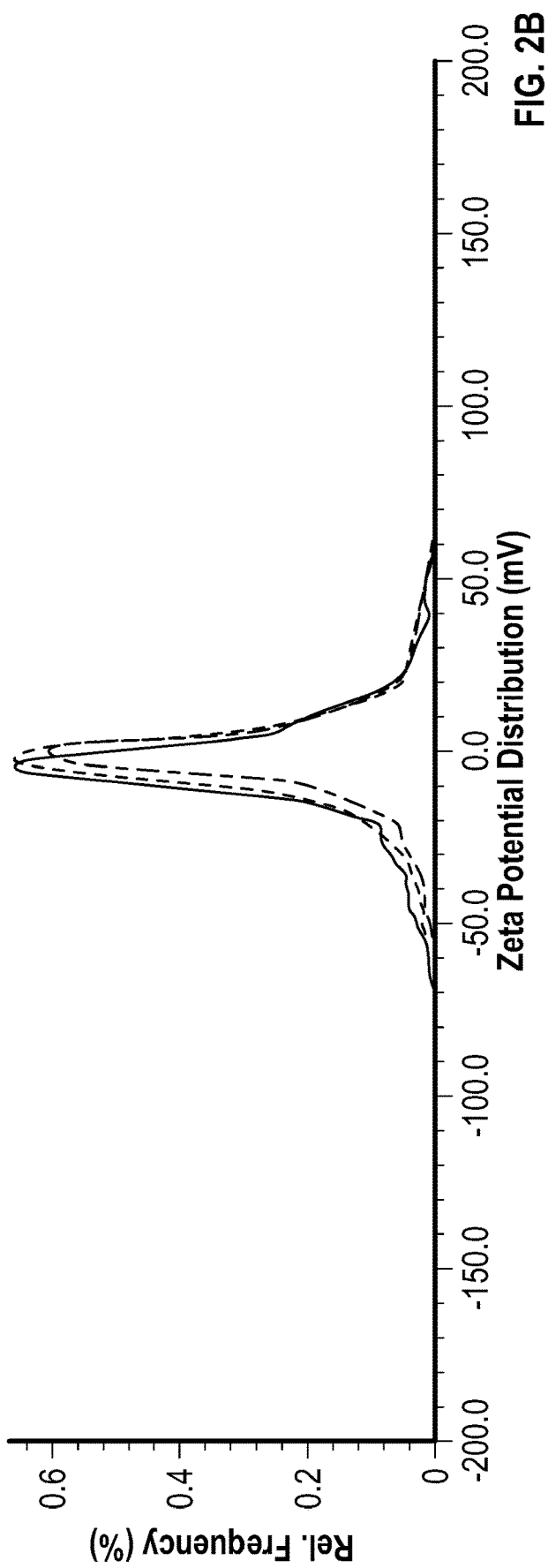

EXTRACELLULAR VESICLES FOR INHALATION

This application is a national stage application under 35 U.S.C. § 371 of International Application No. PCT/EP2019/071511, filed Aug. 9, 2019, which designated the U.S. and claims priority to European Patent Application No. 18188591.4, filed Aug. 10, 2018, and European Patent Application No. 19154302.4, filed Jan. 29, 2019, the disclosure of each of which is incorporated herein by reference in its entirety.

INTRODUCTION

The present invention relates to extracellular vesicles, in particular exosomes, compositions containing the vesicles, their uses and methods for the use and manufacture thereof. The present invention also relates to the use of such vesicles in therapy and gene therapy, particularly for the treatment of respiratory tract diseases such as cystic fibrosis (CF), COPD and lung cancers.

BACKGROUND TO THE INVENTION

Extracellular vesicles are nano-sized membranous vesicles encapsulated by a lipid bi-layer and actively secreted by most prokaryotic and eukaryotic cells. Extracellular vesicles include exosomes, microvesicles and membrane blebs.

Vesicles in general are formed by exocytosis from living cells. Exosomes differ from many other extracellular vesicles in that they originate from endocytic compartments in the cells, and are expelled from the cell by means of exocytosis when multivesicular bodies fuse with the plasma membrane.

Formation of the multivesicular bodies is a step-by-step process that begins by the formation of early endosomes. These early endosomes mature into late endosomes and during this process, several cargos, either for destruction in the lysosomal compartment or sorted into small vesicles to be secreted, are selectively taken into the interior of endosomes by the invagination of their membrane and gradually form numerous intraluminal vesicles. These endosomes with numerous intraluminal vesicles are now called late endosomes and then mature to form MVBs, which eventually fuse with the plasma membrane to release these vesicles as exosomes.

Extracellular vesicles generally have a size in the range of up to about 1000 nm, with exosomes generally have a size in the range of 30-150 nm. In addition to their signature membrane molecules vesicles, including exosomes, naturally have an intravesicular cargo that can include a variety of proteins, RNAs, and microRNAs in aqueous solution/suspension.

Vesicles, in particular exosomes, are involved in cell-cell communication and inter-cellular signal transduction. As a result, exosomes and other vesicles have recently started being used in experimental disease models to deliver drugs or desired molecules. Due to their natural origin, exosomes hold a distinct advantage over liposome-based drug delivery as an efficient and reliable means to deliver various nucleic acid based therapeutics, macromolecules and drugs.

Vesicles' capacity to carry proteins, RNAs and microRNAs in a cytoplasmic core makes them convenient drug delivery vehicles. Additionally, the presence of a lipid bilayer provides structural integrity, shields the nucleic acids from degradation and enables the exosomes to withstand shear stress.

Exosomes are known be able to penetrate cell membranes easily and also to evade the immune system, partly due to their size. As exosomes are naturally occurring nanovesicles, they do not have a cytotoxic effect as liposomal or other nanoparticle based drug carriers might have and have a better circulatory half-life and better penetration across various biological barriers.

Cystic fibrosis (CF) is a genetic disorder in which the patient has inherited mutation in both copies of the gene for the cystic fibrosis transmembrane conductance regulator (CFTR) protein. CFTR is involved in the production of various secretions, in particular mucus, digestive fluids and sweat. Whereas such secretions are usually thin, as a result of the mutation in cystic fibrosis patients the secretions are thick. In the lungs, such thick secretions result in significant phlegm production, decreased clearance of the mucus, clogging of the airways due to the mucus build-up, persistent coughing, frequent lung infections and difficulty in breathing.

While there are currently no known cures for CF, gene therapy is being explored as a possible potential cure. Various approaches have been tried for gene therapy, including liposomes and viral vectors. However, such treatments have been found to be inefficient, largely due to vector inefficiency and safety concerns. Viral vectors may elicit an undesirable immune response which hinders repeated administration and may also cause potentially carcinogenic insertional mutagenesis via integration of viral DNA with the host genome.

As CF causes significant problems in the lungs, efficient delivery of gene therapy to the lungs is considered to be a requirement for an effective therapy.

Vesicles, including exosomes, appear to be possible delivery vehicles for gene therapy, and indeed other types of therapy, for example regenerative medicine, protein, antibody or small molecule based therapy, to the lung. However, there are at least two significant difficulties. Firstly, mucus in the lung provides a significant barrier to any gene transfer vehicle reaching the cells of the lungs. Mucus is a sticky viscoelastic gel that protects against pathogens, toxins, and debris at various points of entry into the body, including the eyes, nose, lungs, gastrointestinal tract, and female reproductive tract. Many nanoparticles are strongly mucoadhesive and become effectively trapped in the rapidly-cleared peripheral mucus layer, vastly limiting their distribution throughout the mucosal membrane as well as penetration toward the underlying tissue. Clinical trials testing viral gene vectors, including adenovirus (AdV) and adeno-associated virus (AAV) serotype 2 and non-viral liposome vectors for inhaled gene therapy have failed to provide clinically significant benefits due to inefficient gene transfer to airway epithelium, generation of therapy-inactivating host immune responses and in the case of liposomal gene therapy the delivery of sufficient doses was another recognized challenge. Various studies have shown that mucus trapping impedes access of these vectors to the underlying epithelium and thus prevents successful gene transfer. The residence time of these trapped particles is limited by the turnover rate of the peripheral mucus layer, which, depending on the organ, ranges from seconds to several hours. To ensure effective delivery of particles including pharmaceutical agents via mucus membranes, such particles must be able to readily diffuse through the mucus barrier, avoiding mucus adhesion and escaping the mucociliary clearance defences.

Furthermore, once the mucus barrier has been crossed, it is also necessary to cross the cell membrane barrier. This is also designed to provide a barrier to prevent access to the cell, particularly for viruses and foreign particles.

Viral vectors may also be neutralised by existing immune responses or by acquired immune responses upon repeated administration. The use of stem cell exosomes or EVs, which are immune privileged, can bypass this problem. The PEG coating can further increase the stealth properties of stem cell exosomes by effectively shielding surface antigens.

In addition, the aerosol delivery of therapeutically relevant doses of vesicles may be problematic for many standard nebulizers. Vesicles in an aqueous nanosuspension or colloid can aggregate or agglomerate. Inter-particle forces, especially in concentrated nanofluids, result in increased viscosity which in turn causes very significant difficulties in aerosolization. Additionally the aggregation or agglomeration results in the vesicles not forming a true suspension or colloid, as the vesicles are not spread throughout the fluid, but clumped together or adhered to the walls of the vessel in which the nanosuspension or colloid is held.

The efficient delivery of cargo, in particular nucleotide sequences and proteins, to lung airway epithelial cells remains a common problem for all approaches.

Kooijmans et, "PEGylated and targeting extracellular vesicles display enhanced cell specificity and circulation time", Journal of Controlled Release, vo. 224, 7 Jan. 2016, p 77-85 describes the decoration of extracellular vesicles with targeting ligands conjugated to polyethylene glycol in order to improve the specificity of vesicles and prolong their time in the circulation system before clearance. This paper describes the production of extracellular vesicles from mouse neuroblastoma cells and does not address the issues of mucus penetration or cell membrane penetration. Indeed this paper suggested that PEGylation adversely affects cellular uptake.

Myung Soo Kim, "Engineered macrophage-derived exosomes for targeting paclitaxel delivery to pulmonary metastases: in vitro and in vivo evaluations", Nanomedecine: Nanotechnology, Biology and Medicine, vol. 14, no. 1, 2 Oct. 2017, pages 195-204 also describes exosomes decorated with PEG conjugated with a cell/receptor specific ligand. Again this document does not address any of the issues associated with delivery of vesicles to the lung, and does not mention crossing the mucus barrier or the cell membrane. In addition this document describes a cargo of paclitaxel.

U.S. Pat. No. 9,901,600, in the name of Alexander Mitsialis, describes the use of exosomes for the treatment and/or prevention of lung diseases. The exosomes may include a cargo of proteins or nucleic acids. These exosomes are uncoated and do not address the issues of the mucus barrier or the cell membrane barrier. While this document suggests administration by injection or inhalation, no information of how aerosolisation of the exosomes, as needed for inhalation, can be achieved.

It is desirable to provide vehicles for the delivery of gene therapy to the cells of the lung, using an inhaled delivery system. It is also desirable to provide a delivery vehicle that can pass through a layer of mucus and penetrate cell membranes, additionally the delivery vehicle should be carried in a formulation that can be aerosolized.

It is an object of the invention to provide a vesicle, in particular an exosome, that can be aerosolized and pass through a mucus layer to penetrate into lung cells. It is a further object of the invention to provide vesicles, in particular exosomes, for use in therapy, specifically for therapy of lung diseases.

SUMMARY OF THE INVENTION

According to the invention there is provided an aerosolizable composition comprising extracellular vesicles from mesenchymal stem cells (MSCs) having a surface coating of the hydrophilic polymer polyethylene glycol (PEG), the vesicles carrying a cargo comprising of one or more of a microRNA (miR), an anti-MIR, mRNA, a long non-coding RNA, a circular RNA, a small interfering RNA, a short hairpin RNA, a piwi-interacting RNA, a CRISPR RNA sequence, modifications of the foregoing or artificially designed nucleic acid sequences, a protein, a cytokine or a lipid.

Such compositions suitably comprise surface-coated vesicles in the form of a colloid or suspension. The coating of hydrophilic polymer generally results in vesicles that are able to form a suspension or colloid in an aqueous formulation, and are able to penetrate mucus and enter cells to deliver therapeutic cargo.

The invention also provides the vesicles per se and such a vesicle-containing composition, e.g. as colloid or suspension, for use in therapy, wherein the vesicles have a therapeutic cargo and a surface coating of a hydrophilic polymer.

Such cargo may comprise a microRNA (miR), a microRNA modulating nucleic acid sequence such as an antimiR/antagomir or other non-coding nucleic acid sequences which may alter gene expression in the targeted disease cells (e.g. long non-coding RNA or circular RNA which may act as microRNA sponges, thus exerting antimiR effects; small interfering RNA or short hairpin RNA for specific gene knockdown, piwi-interacting RNA for disease implicated gene or transposon silencing, etc.), an mRNA, lipids, proteins, cytokines or small molecules, for delivery to target cells. All of the nucleic acids may be altered or sequence engineered for modified effects. Such cargoes may comprise one or more or two or more or all of a microRNA (miR), a mRNA, an antimiR, other naturally occurring or artificially produced nucleic acid sequences, a lipid, a protein, a cytokine and a small molecule therapeutic agent. Such cargoes can be introduced e.g. into exosomes during biogenesis by their parent cells (e.g. by overexpressing a microRNA via genetic modification of the producing cell type) or a therapeutic molecule can be introduced into an exosome after it is isolated from the culture medium (e.g. using electroporation, heat shock, transfer solutions/reagents or other methods to introduce a small molecule, protein or nucleic acid sequence such as an anti-microRNA, mRNA or microRNA). When vesicles, e.g. exosomes, are introduced into the cytoplasm of a targeted lung cell they can provide a treatment against cystic fibrosis (CF), Chronic Obstructive Pulmonary Disease (COPD), lung cancers, idiopathic pulmonary fibrosis, obstructive lung disease, asthma, pulmonary hypertension, bronchopulmonary dysplasia and other lung conditions and diseases.

The invention also provides a composition as described above for use in therapy.

According to the invention there is also provided a method of treating a patient having a lung disease, comprising providing a composition as described above;
forming an aerosol of vesicles of the composition; and
administering the aerosol to the patient.

DETAILS OF THE INVENTION

The provision of a surface coating of a hydrophilic polymer on vesicles reduces their propensity to aggregate or agglomerate, resulting in a colloid or suspension of coated vesicles which can be aerosolized and also has the ability to pass through mucus to penetrate into cells and, if present, deposit their additional therapeutic cargo which has been incorporated into the EVs either as a result of genetic modification of the EV producing cells or otherwise incorporated exogenous cargo.

Preferably the vesicles are exosomes, as used e.g. in the examples below. Alternatively, the vesicles may be microvesicles, membrane blebs or membrane particles.

Preferably the vesicles, particularly exosomes, are derived from animal cells, more preferably from human cells. The cells may be somatic cells or stem cells.

In preferred embodiments of the invention, exosomes are derived from mesenchymal stem cells (MSCs), especially human MSCs. Such vesicles display innate therapeutic properties and delivery of these into target cells has been shown to modulate fibrosis, inflammation, tissue regeneration and pro-survival effects. More preferably the vesicles, particularly exosomes, are derived from hTERT immortalised adipose or bone marrow derived mesenchymal stem cells. MSCs can be genetically modified to overexpress specific miRs; there are commercially available overexpression constructs for microRNAs and antimiRs (e.g. XMIRXpress Lentivectors from Systems Biosciences that can transform cells to overexpress the miR/antimiR of choice while the XMotif directs high concentrations of miRNAs to exosomes). The MSCs can package these miRs into exosomes or other vesicles, which can be harvested, and purified, using standard techniques for use as described. Immortalised MSCs are an ideal source cell bank, possessing an enormous capacity for stable overexpression of bioengineered nucleic acid cargoes and expansion which is ideal to produce commercial scale vesicle, in particular exosome, therapeutics.

Vesicles, in particular exosomes, can be used for the treatment of many disease conditions. Vesicles with a hydrophilic polymer coating can be aerosolized and, upon deposition in the appropriate areas of the lung, are also better able to pass through mucus and unexpectedly, in spite of the surface modification, they demonstrate a retained ability to readily cross the cell membrane. As such, the vesicles of the invention are particularly suitable to be tailored for use in the treatment of lung conditions, such as but not limited to cystic fibrosis (CF), chronic obstructive pulmonary disease (COPD), lung cancer, asthma, pulmonary hypertension, Acute Respiratory Distress Syndrome (ARDS), Idiopathic Pulmonary Fibrosis and other conditions affecting the lungs.

Exposed organs, in particular the airways, secret a viscoelastic mucus in order to trap and eliminate foreign pathogen and ultrafine particles. As a result, mucus provides a significant barrier to the penetration of therapeutic agents delivered to the lungs. While small molecule drugs are generally able to penetrate the mucus barrier resulting in aerosol delivery of such therapeutics being a successful delivery method, the mucus barrier has proved very problematic for the delivery of biological molecules, such as gene transfer agents or vectors for use in gene therapy.

Vesicles, in particular exosomes, of the invention comprise a coating of a hydrophilic polymer. It is advantageously found that these coated vesicles have improved properties of aerosol formation. It is separately found that the coated vesicles penetrate more easily the lung mucus, facilitating access to lung tissue in treatment of lung disease or in other therapeutic applications wherein actives are delivered to or via lung tissue.

Coated vesicles, in particular exosomes, of the invention are found to form suspensions and/or colloids that have reduced viscosity compared with uncoated exosomes, this effect is believed to be the result of steric stabilisation of the exosomes in nanosuspension/colloid. The formation of a suspension having dispersed particles, or a colloid, facilitates formation of aerosols with aerosol particles in a suitable size range for delivery to the lungs and containing useful concentrations of vesicles. These compositions are useful for delivery of the vesicles, for example exosomes, per se and also useful for delivery of vesicles comprising additional components for therapeutic use via delivery in or incorporated into or onto the vesicles. Such exosomes may display additional cell specific targeting moieties either attached (e.g. via click chemistry) or those which have been expressed as a result of genetic engineering. Such targeting ligands may enhance the uptake of exosomes into specific cell types (e.g. fibroblasts, immune cells, endothelial or epithelial cells).

The hydrophilic polymers used in the invention thus result in vesicles that show reduced aggregation or agglomeration in solution forming a colloid and suspension. Suitably, the polymers are substantially non-ionic and substantially uncharged. One result is that coated exosomes of the invention generally have a surface charge that is reduced compared to uncoated exosomes and tends towards a substantially neutral net surface charge.

A surface coating of the hydrophilic polymer polyethylene glycol (PEG) indicates that the PEG is on the outer surface of the extracellular vesicle, such that its functionality is available. This enables the properties of PEG to influence the properties of the extracellular vesicle, for example its hydrophilic properties. As such the PEG is not an inside part of another coating and does not have any significant coating on the PEG. The PEG coating is the outermost coating on the extracellular vesicles. No additional ligands or other elements are conjugated on the distal ends of the PEG. The PEG forms substantially the only coating on the extracellular vesicles.

The low molecular weight PEG is preferred to have a molecular weight of less than 3 kDa and preferably provides the EVs with a dense surface coating of 65% or greater, which is sufficient to substantively neutralise the surface charge of the EVs (i.e. between −8 mV and 0 mV).

Preferably the surface coating will cover at least 65%, more preferably at least 70% and most preferably at least 75% of the vesicles surface to provide sufficient steric stabilization and surface charge neutralisation to minimise exosome agglomeration and aggregation. In specific examples, illustrated below, a surface coverage of approximately 70% or higher was seen in coated exosomes that generated aerosols and penetrated mucus.

The surface coating polymer generally has a low molecular weight, preferably <5 kDa, more preferably <4 kDa, more preferably <3 kDa and most preferably between 2 kDa and 3 kDa. In specific examples, illustrated below, a coating was formed from the attachment of polymer chains of approximately 2 kDa to the surface of the vesicles. As a result the chains do not provide steric interference or hindrance with mucin chains that can be encountered in the lungs mucus layer. The polymers are suitably incorporated in a concentration that is sufficient to substantially neutralise the vesicles surface charge and prevent agglomeration or aggregation; such a dense coating will allow the conformation of the hydrophilic chains in the optimal 'brush' orientation/conformation. The concentration of polymer required depends on many variables such as the chain length of the chosen polymer, the efficiency of polymer binding to the vesicle surface and the molar concentration and particle size distribution of the isolated vesicle sample. For example, a polymer incubated with 100 nm exosomes may be used at approximately 8 mol % or greater to ensure dense coverage and suitable vesicle characteristics post modification. However, care must be taken to avoid excessively high polymer concentrations which may result in damage to the vesicle membrane via detergent mediated disruptive effects at higher concentrations.

Vesicles of the invention typically have a size in the range of 20-1000 nm, more suitably in the range up 300 nm. Exosomes typically have a size in the range of 30-150 nm, and microvesicles typically have a size in the range of 100-1000 nm. Typically, exosomes of the invention with a surface coating have a size in the range of up to 200 nm, preferably 20-200 nm and most preferably 30-180 nm. Sizes may be measured using dynamic light scattering techniques (Degiorgio, V., et al., 1979) or nanoparticle tracking analysis (NTA, used in the examples below).

As indicated, preferably the vesicles are derived from mesenchymal stem cell and as such have the major advantage of possessing innate regenerative and therapeutic properties. Studies have shown that unmodified MSC exosomes and MSCs themselves exhibit anti-apoptotic, pro-angiogenic and anti-inflammatory effects via a variety of factors (e.g. microRNAs, mRNAs, lncRNAs, KGF, HGF, VEGF, IGF-1, TIMP3) and by an array of mechanisms (e.g. by polarization of macrophages from pro-inflammatory M1 phenotype to an anti-inflammatory M2 phenotype, modulation of antigen presentation, modulation of cytokine release, enhancing glycolysis via ATP generating enzyme transfer and activation of survival kinases (e.g., ERK & AKT via CD73), and by reducing complement activation through CD59).

These beneficial effects can be enhanced by the addition of relevant cargo to the vesicle, for example the exosomes. Indeed, whatever the source of the vesicle, the cargo can provide a beneficial therapeutic effect.

The vesicles, in particular exosomes, may also carry a cargo to be delivered to the target cells. Preferably, this cargo is a microRNA (miR) or anti-microRNA (antimiR). Alternatively, the cargo may be an mRNA, or another endogenous or exogenous nucleic acid construct, a sequence engineered, chemically modified or synthetic version of the foregoing, a protein or a pharmaceutical small molecule. The nucleic acid may be sequence engineered or use modified base pairs and loaded into exosomes via a variety of mechanisms.

The vesicles also have utility for in vivo pulmonary delivery of CRISPR-Cas9 or other modes of gene editing as intracellular delivery to the cells underlying the mucus barrier is a problem that needs to be overcome in order to successfully edit genes in the case of respiratory diseases.

In some embodiments of the invention, hTERT mRNA and the hTERT enzyme catalytic subunit may be incorporated into the exosomes as a result of lentiviral hTERT immortalisation of the EV producing stem cells, these active moieties are useful for combating cellular senescence in target disease cells (e.g. AEC2 alveolar epithelial progenitor cells) which is a feature of COPD, IPF and is becoming increasingly implicated in other lung diseases. Similarly, other major component of the telomerase enzyme, TERC (hTR) may be incorporated into the EVs as an RNA molecule. These cargoes will act within the target cells to enhance the regenerative medicine capacity of the stem cell EVs. Importantly, these effects will be transient and reversible in nature as they will act in the cytoplasm and not integrate into the target cells genome which is an important regulatory consideration as no enduring effects will be demonstrable in the target cells or indeed any daughter cells produced by the targeted cells.

MicroRNAs (miRs) are small non-coding RNA molecules, typically containing of the order of 20-25 nucleotides, found in plants, animals and some viruses, which primarily function in RNA silencing and post-transcriptional regulation of gene expression. miRs function via base-pairing with complementary sequences within mRNA molecules and are key regulators of gene expression. The cargo may also be antimiRs or antagomiRs. The cargo will be customised for applicability to the condition to be treated or modulation of gene expression in a specified target cell type. Typically, conditions or disease states result in the upregulating of certain miRs, and the downregulating of other miRs. Where the miR is downregulated treatment to replace that miR can be effective, while where a miR is upregulated, provision of the anti-miR or antagomiR can be effective.

The cargoes of the EVs may be other non-coding nucleic acid sequences which may alter gene expression in the targeted disease cells. For example long non-coding RNA or circular RNAs (endogenous or artificially constructed) which may act as microRNA 'sponges' or 'mops', thus exerting antimiR effects; small interfering RNA or short hairpin RNA for specific gene knockdown; and piwi-interacting RNA for disease implicated gene or transposon silencing.

Where the cargo is a miR, and the treatment is for COPD, preferably the cargo is selected from one or more of miR-125b-5p, miR-125b-1-3p, miR-513a-5p, miR-34c, miR-452, miR-146a, Let-7c, miR-576-3p, miR-513a-3p, miR-923, miR-937, miR-422a, miR-25, miR-99b, miR-24 and miR-187. More preferably the miR is selected from miR-125b-5p, miR-125b-1-3p and miR-513a-5p which represent new genetic targets for disease reversal. The selected microRNAs, hsa-miR-125b-5p, hsa-miR-125b-1-3p & hsa-miR-513a-5p, are key regulators in COPD, targeting important genes involved in COPD pathogenesis. These miRs are under-expressed in smokers with COPD compared to smokers without COPD and are known to target and downregulate several important mRNAs via functional microRNA-Target-Interactions (MTIs), which are involved in disease pathogenesis.

Specifically, MicroRNA 125b-5p is a suitable cargo and has been shown to target & downregulate the following important COPD associated genes:

[1] ADAMTS4 (Aggrecanase-1) in studies on human osteoarthritic chondrocytes. ADAMTS4 is a proteolytic enzyme involved in extracellular matrix disassembly and is the most overexpressed mRNA (8.91-fold increase) in smokers with COPD vs. those without COPD. Furthermore, ADAMTS4 has been shown to be anti-angiogenic by binding VEGF, downregulation of ADAMTS4 may thus aid in angiogenic regeneration of the alveolar compartments;

[2] SFRP5, a WNT antagonist whose levels were found to be significantly higher in COPD compared to healthy controls;

[3] DKK3, a notch antagonist, whose downregulation may aid alveolar regeneration;
[4] EGFR bronchial epithelial cell expression is significantly higher in smokers compared to healthy controls & also higher in smokers with COPD compared to those without COPD. EGFR plays an important role in regulating mucus production & goblet cell hyperplasia in airway epithelium;
[5] Receptor for IL-6 (IL6R), well-recognized key inflammatory pathway in COPD;
[6] MMP13, a collagenase MMP sub-family member that has been shown to be upregulated in COPD alveolar macrophages and alveolar type II cells. MMP13 is implicated as an important mediator of disease pathogenesis in response to cigarette smoke and PR8 influenza virus exposure in an animal model of COPD exacerbations;
[7] ANGPT2, an ANGPT1 (angiopoietin) antagonist. ANGPTL1 has decreased levels in advanced COPD vs. stable phase/normal levels (associated with vascular regression, levels strongly correlate with loss of lung function);
[8] APC, WNT Signaling Pathway Regulator, inhibitory as APC is a component of beta catenin destruction complex;
[9] MAPK14 (P38 inhibition is promising in COPD clinical trials); and
[10] Various other targets that are strongly associated with COPD: SGPL1, BMPR1B, BTG2, CEBPA, Fas, FGFR2, FZD6, GLI1, HK2, HMGA1, HMGA2, IGF1R, IGF2, MMP2, MMP26, MUC1, SMAD4, STAT3, TNF, TNFAIP3, TP53 & BCL2—pro & anti apoptosis mediators respectively but BAK1, BCL2 Antagonist/Killer 1, is also a target, TP53INP1, VDR, ERBB2 & ERBB3.

Furthermore, enforced expression of miR-125b-5p has shown attenuation of LPS-induced acute lung injury and inflammation in mice.

MiR-125b-1-3p is a suitable cargo and has been shown to target COPD relevant genes:
[1] Increased expression of TACSTD2 (aka TROP2) in airway basal cells potentially contributes to airway remodelling in COPD and airway remodelling through increased basal cells hyperplasia;
[2] SGPL1, a sphingosine-1-phosphate (S1P) degrading enzyme with a 4.5-fold increase in expression in COPD alveolar macrophages vs. controls. Contributes to alveolar macrophage defects in apoptotic cell phagocytosis (efferocytosis) in COPD;
[3] FRZB, a WNT antagonist, whose downregulation is expected to exhibit regenerative effects;
[4] TP53, increased expression of pro-apoptotic P53 in alveolar type II cells of COPD. Thus, downregulation is expected to have a pro-survival effect, note that 125b-5p is also a target for P53;
[5] S1PR1 (cell adhesion, immunomodulatory);
[6] BIK, accelerates programmed cell death;
[7] MTFP1;
[8] MAP2K7, involved in environmental/cellular responses;
[9] BGLAP and
[10] ITGA9.

MiR-513a-5p is also a suitable cargo for vesicles of the invention because of its relevant effects on COPD gene expression:
[1] CBL—miR-513a-5p has been shown to target CBL, negatively impacting the phosphoinositide 3-kinase (PI3K)-AKT & nuclear factor-κB (NF-κB) pathways through its downstream genes, spleen tyrosine kinase (SYK) & epidermal growth factor receptor (EGFR). Increased 513a-5p thus decreased secretion of cytokine factors interleukin (IL)-10, γ-interferon (γ-IFN), tumor necrosis factor-α (TNF-α) & IL-12;
[2] CD274 (Programmed Death Ligand 1) Emphysematous bullae (EB) associated lung adenocarcinomas express PD-L1 protein more frequently than those without EB. PD-L1—immune checkpoint is incompletely understood but dysregulated in COPD. PD-L1 protein is induced in various non-lymphoid tissue cells, including epithelial, endothelial, smooth muscle cells, in response to inflammatory cytokines. The well recognized COPD-lung cancer co-morbidity makes CD274 a target of particular interest;
[3] miR-513a-5p has many additional and interesting in silico predicted targets for investigation (TargetScan 7.2): AGER (encodes RAGE, upregulated in COPD—RAGE KO mice show decreased inflammatory responses and upregulation of RAGE causes increased alveolar cell apoptosis); ADAMS and INHBA (aka Activin A, TGFB superfamily increased in COPD & associated with airflow limitation).

Additionally, miRs identified herein as suitable for the invention have shown functional MTI (Weak) for many more COPD associated genes.

Lung cancer is a highly significant and deadly comorbidity of COPD. The increased risk of lung cancer exhibited by individuals with COPD is independent of smoking history. In forthcoming experiments, we aim to reduce the lung cancer risk by the modulation of miR-21-5p in the COPD diseased and surrounding lung tissues, such a reduction of miR-21 is believed to be capable of reducing the risk of COPD patients developing lung cancer and will be achieved by genetic modification of stem cells to overexpress an antimiR sequence to miR-21 (hsa-miR-21-5p) which will load into EVs. The miR-21-5p inhibitor is either a short RNA with the reverse complementary sequence of the miRNA or it may take the form of a circular RNA sequence with several miR-21-5p binding sites and the use of intron terminal sequences to drive circularization. Alternatively a naturally occurring or modified long non-coding RNA sequence may be utilised to achieve a reduction of miR-21.

Where the cargo is a miR and the treatment is for CF, preferably the cargo comprises miR-17, to reduce hyper-inflammation in the CF lung. CF is a multisystem disease but the vast majority of complications and fatalities occur due to lung related disease. Administration of anti-inflammatory MSC exosomes of the invention with microRNA cargoes are suitable to dramatically improve lung function. Furthermore exosomes delivered to the lung are expected to have a degree of systemic absorption and effects due to the high surface area and vasculature of the lungs.

The cargo may additionally or alternatively comprise mRNA. Where the treatment is for CF, the cargo may be a modified CFTR mRNA. For example, the modified CFTR mRNA may include mutated or deleted miR binding sites for miR-101, miR-223, miR-494 and/or miR-509-3p as these are upregulated in CF and repress CFTR expression. Alternatively, the introduced CFTR mRNA may incorporate synthetic 3' and 5' UTRs that are designed to express freely in the majority of cell types & will also be devoid of the noted disease upregulated miR binding sites. Recent studies have shown that miR target site blockade or site mutagenesis at these sites have led to increased CFTR expression. In addition, modified CFTR mRNA is resistant to in vivo intracellular miRNA degradation and therefore has a longer half-life for prolonged in vivo CFTR expression. In addition, enhanced efficacy compared to target site blockers may be achieved because functional CFTR protein will be translated from a wild type protein coding sequence as opposed to the rescue of endogenous mutant CFTR mRNA expression which can elicit cellular stress due to unfolded protein responses.

Where the exosomes are used in the treatment of lung cancer specifically adenocarcinoma, the cargo may be one or more of miR-126-3p, miR-218-5p, miR-486-5p, miR-145-5p, miR-338-3p, miR-195-5p, miR-143-3p, miR-139-5p, miR-126-5p, miR-144-3p, miR-34c-5p, miR-30a-3p, let-7c-5p, miR-451a, miR-1-3p and miR-133a-3p. Additionally or alternatively, the cargo may be one or more of the anti-miRs of miR-21-5p, miR-210-3p, miR-182-5p, miR-183-5p, miR-9-5p, miR-135b-5p, miR-9-3p, miR-96-5p, miR-205-5p, miR-31-5p, miR-708-5p, miR-196b-5p, miR-375, miR-345-5p, miR-200a-3p and miR-130b-3p.

Other suitable cargos may include microRNAs or anti-miRs selected for the treatment of other lung diseases e.g. Idiopathic Pulmonary Fibrosis.

The compositions are suitably provided as suspensions or colloids for delivery to the lungs via aerosolization using nebulizers. Preferably the suspensions or colloids are aqueous based. The compositions may also include other pharmaceutically acceptable excipients such as but not limited to salts, surfactants, stabilizers, preservatives, cryoprotectants, buffering and pH adjusting agents.

Compositions of the invention are for generation of aerosols containing droplets that may be delivered to a lung of a patient. Suitable sizes and aerosol generating devices are known in this field, and aerosols typically comprise droplets sized 10 μm and less. Aerosolized droplets of >5 μm are generally considered too large for respiratory delivery under normal breathing conditions. In order to reach and adhere to the bronchial and alveolar cells the aerosol droplets are very suitably in the range 1-5 μm, i.e. the aerosol includes droplets in this range. Those familiar with the art will recognize that droplets larger than 5 μm in diameter may deposit in the desired lung regions when appropriate limitations are imposed on inspiratory flow rates and aerosol velocities. Larger droplets, being spherical, carry a much larger volume than smaller droplets—for example a droplet that is 10 μm in diameter has a thousand times greater volume (and hence dose loading capacity) than a droplet that is 1 μm in diameter. The targeting of aerosol deposition to the desired lung region can be effectively controlled by variation of the aerosol delivery device and formulation parameters to suitably influence the aerosol droplet size and inhalation flow rates. Aerosol droplet size can be measured for example by Mass Median Aerodynamic Diameter (MMAD) values which are defined as the aerosol diameter at which 50% of the particles by mass are larger and 50% are smaller.

In order to achieve successful aerosolization it is generally preferred that the viscosity of the colloid or suspension is not too high; these parameters are, however, also device type and model dependent. Preferably the viscosity should be less than 6 cP, for example less than 4 cP, more preferably less than 3 cP and most preferably less than 2 cP. Where a colloid or suspension is too viscous, the process of aerosolization may lead to foaming and spluttering and thus significantly reduce aerosolization or if aerosol generation is possible, the droplets generated may be too small to have useful deposition for the intended region of the lung. Equally, where the particles in the suspension or colloid have a tendency to aggregate or agglomerate, then the aggregated particles are not aerosolized, but can instead remain in a colloid or suspension of increasing concentration in the nebulizer's reservoir. This then results in an increase in the viscosity of the suspension or colloid and failure of aerosolization or reductions in the delivered dose. Free vesicles, including exosomes, have a strong tendency to aggregate or agglomerate, forming a viscous colloid or suspension and thus cannot be aerosolized efficiently. However, vesicles of the invention having a hydrophilic polymer coating have been found to show a significantly reduced tendency to aggregate and agglomerate. As a result a colloid or suspension of a suitable viscosity can be formed, and the coated vesicles provided herein can be successfully aerosolized.

The size of aerosol droplets formed is generally inversely proportional to the viscosity of the formulation being nebulized. The viscosity of nanoscale colloidal systems such as exosome formulations increases sharply as the volume fraction of the exosomes increases. As previously mentioned, steric stabilisation of the vesicles of the invention can significantly mitigate this effect. This effect can be used to contribute to aerosol deposition of the formed aerosols in the targeted region of the lung, where smaller droplets (with a constant velocity and inspiratory flow rate) will deposit in the smaller airways and peripheral/distal regions of the lung and larger droplets will have a more central deposition pattern. For example, in the case of Cystic Fibrosis a central aerosol deposition pattern is desirable targeting the bronchial regions and large conducting airways. Conversely in the case of emphysema the distal alveolar regions and small airways are the primary regions of interest and smaller droplet size distributions are preferred.

Aerosolization may be carried out using a nebulizer. Nebulizers use oxygen, compressed air or gases and/or nozzles or ultrasonic power to break up solutions, suspensions and colloids into small droplets, forming a mist that can be inhaled. Nebulizers were previously designed to aerosolize small molecules and all commercial types are successful at this if the drug is in solution. However, the type of nebulizer used is more important for larger biological agents, which can be damaged by nebulizers which impart too much energy to the solution, suspension or colloid, and generate enough hydrodynamic stresses to shear biological molecules, resulting in loss of activity. For example, ultrasonic nebulizers are completely unsuited to delivery of nanosuspensions and compression nebulizers cause continual recirculation of the aerosol resulting in repeated shear stresses which can damage biologic molecules, such nebulizers also preferentially aerosolize the aqueous carrier resulting in concentration of the formulation in the reservoir. The 'dead volume' of the formulation that is not aerosolized but left in the reservoir is typically 1 ml in compression nebulizers and this is completely unacceptable and commercially unviable from a cost of goods perspective with regard to advanced therapies such as exosome formulations.

Of the regulatory approved nebulizer types vibrating mesh nebulizers are especially suitable for the delivery of vesicles as
1. droplets only change phase from liquid to air once on droplet generation (compared to 'recycling' and repeated shear stresses in compression nebulizers);
2. ultrasonic nebulizers are unsuited to the delivery of nanosuspensions;
3. vibrating mesh nebulizers can be adapted to efficiently deliver small volumes of formulations with minimal residual dead volumes; and 4. compression nebulizers can preferentially aerosolize the solvent and concentrate the remaining formulation in the reservoir.

Surface Acoustic Wave (SAW) nebulizers, which generate surface acoustic waves on piezoelectric chips, have been shown to aerosolize suspensions of fragile nucleic acid molecules such as plasmid DNA vaccines and stem cells. The high frequency, low power mechanism of SAW nebulization is beneficial to avoid minimal damage to biological molecules, including nucleic acids. SAW nebulizers are more successful in aerosolization of more viscous solutions and suspensions than many other types of nebulizer, making them ideal for aerosolization of the suspensions and colloids formed from the aqueous mixture of exosomes, in particular exosomes having a surface coating of a hydrophilic polymer. The viscosity of the liquid determines, in part, the size of the droplets produced by a SAW nebulizer. However, these types of nebulizers have not to date been approved for clinical study uses by any regulatory bodies.

EXAMPLES

To help understanding of the invention, a specific embodiment with a variant thereof will now be described by way of example and with reference of the accompanying drawings, in which:—

FIGS. 1A and 1B are graphs of concentration v size of unPEGylated and PEGylated exosomes, in nanoparticle tracking analysis (NTA);

FIGS. 2A and 2B shows the zeta potential distribution of PEGylated and unPEGylated exosomes;

EXAMPLE 1

Figure 1B:
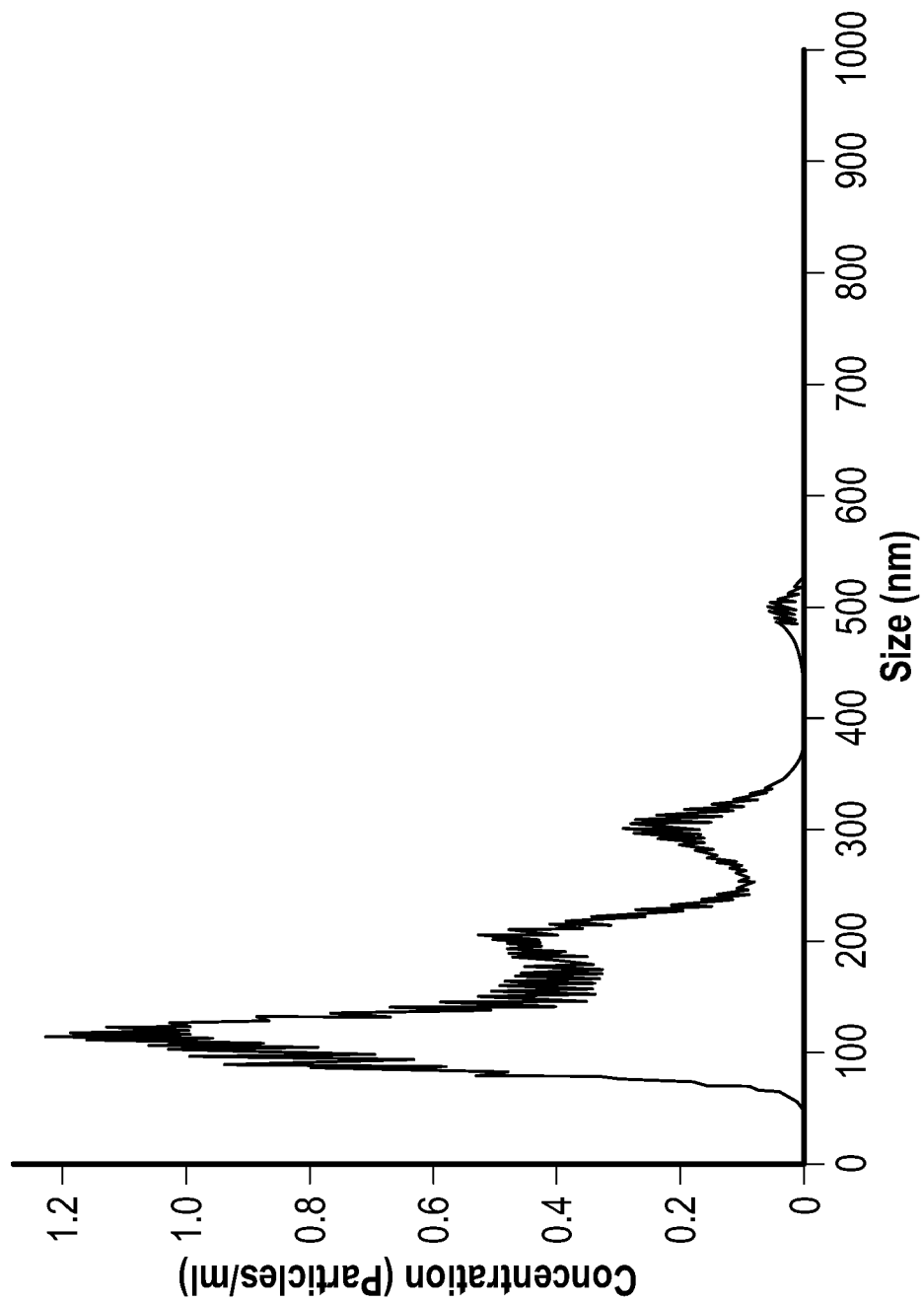

Aims of the example were to isolate exosomes from the human mesenchymal stem cells (hMSC) and to effectively modify their surface with low-molecular-weight lipid-modified polyethylene glycol (lipid-PEG) to improve exosome properties of aerosolization and mucus penetration.

Fluorescent Labelling of hMSCs

Frozen bone marrow MSCs (Donor #163) were thawed before they plated directly into 15 T-175 flasks ($1 \times 10^6$ cells for each flask) in EV-depleted complete culture media (CCM) with 10 ng/ml of human basic fibroblast growth factor (bFGF), passaged when they reached 80-85% confluency. Cells were pooled together before they were pelleted and resuspended in PBS, incubated in the dark with 2 µg/$1 \times 10^6$ cells Far-Red dye (excitation/emission ~630/661 nm) (Cell Trace) for 20 min at the room temperature (this will label exosomes as Far-Red dye labels cytosolic proteins). After incubation, MSC culture media was added to stop the reaction and incubated further for another 5 min before pelleting the cells them and resuspending in EV-depleted CCM.

hMSC Culture for Exosome Isolation

Far-Red labelled hMSCs (Donor #163) were cultured in complete conditioned medium (CCM) and exosomes were isolated according to the previously published data (Thery et al., 2006). Briefly, labelled MSCs were directly seeded into 30 T-175 flasks ($1 \times 10^6$ cells for each flask) in CCM with 10 ng/ml of human basic fibroblast growth factor (bFGF). After 24 hours, media from all the flasks were discarded and replaced with fresh media. Within 3-4 days cells were reached 80% confluency, conditioned media was then collected from each flask and cells were counted from randomly selected 5 flasks. Conditioned media from all the flasks were pooled together before exosome isolation. For exosome isolation, the media was centrifuged at 400×g for 10 min and 2000×g for 30 min to remove cell debris and apoptotic bodies respectively. After each spin, the pellet was discarded and the supernatant was used. The supernatant was then filtered using a 220 nm vacuum filter for further purification and stored at 4° C. until ultracentrifugation (Sorvall Discovery 100SE, Hitachi). Finally, the supernatant was ultracentrifuged at 120000×g for 75 min to pellet exosomes. The pellet was resuspended in PBS to wash exosomes, spun again at the same high speed, the resulting pellet was resuspended in 100 µl PBS and stored at −80° C. until further experiments. All the centrifugation steps were performed at 4° C. and sterile tubes were used.

Post-Isolation Modification of Exosomes by DSPE-PEG

DSPE-PEG (2000) Amine (Avanti Polar Lipids, Inc) was purchased from Sigma Aldrich (Wicklow, Ireland). PEGylated exosomes were prepared based on previously published data on Pegylated liposomal preparation (Li and Huang et al., 2009). A final volume 300 µl of exosome suspension was prepared by mixing 50 µl of concentrated exosome with PBS and 37.8 µl of aqueous solution DSPE-PEG (10 mg/ml) (final concentration of 1.26 mg of PEG in mL of exosome). The sample was then incubated at 37° C. for 1 hr and vortexed at every 10 min to prevent clumping of PEG molecules or exosomes. After incubation, the sample was suspended in more PBS and finally ultracentrifuged at 120000×g for 75 min to wash off unbound PEG molecules. The exosome pellet was then resuspended in 50 µl PBS and stored at −80° C.

Nanoparticle Tracking Analysis (NTA)

Both PEGylated and unPEGylated exosome samples were analysed via Nanoparticle Tracking Analysis (NTA) (Malvern UK) using a NanoSight NS 500 system running NTA version 3.2 using optimized and validated protocols (Maguire et al., 2017, Hole et al., 2013, Gerlach et al., 2017). All the samples were analysed using a NanoSight NS 500 equipped with a 405 nm laser and 430 nm long pass filter. All samples were stored on dry ice prior to analysis. Dilutions for NTA were made up in DPBS buffer (Gibco) that was certified particle free by NTA immediately prior to measurement. Samples were vortexed briefly before loading to ensure adequate mixing and breaking up of weakly bound exosome clusters. Each sample was diluted manually in PBS to obtain an optimum particle concentration suitable for NTA (between 20 and 70 exosomes per field of view), with each dilution factor for being recorded in the automatically generated reports. A total of six×60-second videos were recorded for each exosome sample and the detection threshold during analysis was selected to ensure that only distinct nano-objects were analysed, to ensure that artefacts were removed.

Zeta Potential Measurement

The zeta potential of exosomes was measured using a Litesizer 500, a light-scattering instrument for particle analysis (Litesizer™ 500, Anton Paar Ltd, UK). The zeta potential was measured at slipping plane (15°) of the exosome vesicle and ensured the concentration of particles in each dilution was high enough to provide meaningful measurements by generating a mean detected light intensity of >20 kcounts/s.

Flowcytometric Analysis of Exosome Sample (with Bead Coupling)

For flow cytometric analysis, exosomes ($2\times10^9$ total particles) isolated from Far-Red labelled MSCs were incubated with 10 µl of aldehyde latex beads (0=4 µm) in PBS for 15 min in room temperature without rotation. The sample was then mixed with 950 µl of PBS and incubated overnight at 4° C. with rotation. The remaining binding sites of exosome-beads were then blocked by adding 1M glycine in PBS for 30 min at room temperature. The exosome-coated bead samples were then centrifuged at 1700 RCF for 5 min and the pellet was resuspended in 0.5% BSA in PBS solution. Samples were washed 3 times in a similar manner and resuspended in a final volume of 1 ml of 0.5% BSA in PBS. Exosome-coated bead samples were then either conjugated with a PE-conjugated mouse anti-human antibody to detect CD 9, CD 63, and CD 81 or left untreated as a control. Isotype control was also made by incubating exosome-coated beads with PE-conjugated mouse IgG1 κ, isotype 1 or 2. All the samples were then analysed using BD FACS CANTO and data analysed using FlowJo software.

Transmission Electron Microscopy (TEM)

Morphological examination of both PEGylated and unPEGylated exosomes were performed using an electron microscope (EM). Exosomes were fixed with 2% paraformaldehyde (PFA), washed thrice with PBS prior to being adsorbed to Formvar/Carbon 200 mesh gold EM grids. EM grids were then blocked with PBS/50 mM glycine and PBS/5% BSA before treating them with mouse-anti-human primary antibodies to either CD63 (cat #sc5275, Santa Cruz) or TSG-101 (cat #sc7964, Santa Cruz) (secondary only control on PBS/0.1% BSA) overnight and followed by 30 min in the goat-anti-mouse IgG-Gold secondary antibody (cat #G7652, Sigma). Grids were then fixed with 1% glutaraldehyde and incubated in 2% phosphotungstic acid in PBS to add contrast to the exosome membrane. Exosome grids were then washed in PBS and allowed to air dry before analysing them with TEM microscope.

Mucus Penetration and Cell Internalisation Experiments with Cystic Fibrosis Epithelial Cells Cultured at Air-Liquid-Interface.

Cystic fibrosis (CF) is a genetic disease in which impaired innate host defence results in repeated, severe airway infections. Airway epithelial cell cultures (AECCs) at air-liquid interface differentiate into cells typically encountered in the bronchial epithelium (ciliated epithelial and goblet cells) and produce thick, viscous dehydrated mucus at the apical surface which is exposed to air. The Air-Liquid-Interface model is thus an accurate recapitulation of the conditions that an aerosol delivered gene therapy will encounter in the actual CF lung. Surprisingly, we found that mucus penetration and cell internalisation was achieved by application of high concentrations of non-treated exosomes to the mucus surface of ALI cultures. 25 µl of treated exosomes and untreated exosomes were then applied to the apical mucus surface of the ALI cultures with the dose of treated exosomes being approximately half of the untreated exosomes. (2.65E+07 exosomes per microlitre of untreated control and 1.22E+07 exosomes per microlitre of treated test formulation). After 8 hours of incubation the samples were washed 3 times with PBS, fixed in 4% PFA and stained with phalloidin (tight junctions) and Hoechst (nuceli)

Confocal fluorescent microscopic analysis via Zeiss LSM 710 Confocal. Scanning for xyz image analysis of epithelial cells in treated and untreated samples.

Results

Exosomes isolated from the human bone marrow MSCs were characterized using different methods to quantify their size, to measure their surface charge and to identify them with the presence of some surface markers. Both PEGylated and unPEGylated exosomes were used for characterization (Except for flow cytometry). We isolated exosomes using differential ultracentrifugation as this method remains the most widely used standard method to isolate exosomes from different biological fluids or cell culture supernatants (Chia et al., 2017, Chia et al., 2016, Thery et al., 2006). The nanoparticle tracking analysis (NTA) of both unPEGylated and PEGylated exosomes revealed that their mean size was 143.2±3.5 nm and 165.6±6.0 nm respectively (FIGS. 1A&B). On the other hand, when PEG molecules alone suspended in PBS were analysed with NTA they failed to qualify the quality control criteria. This indicates that the number of particles showed in the PEGylated exosomes sample was not an artefact caused by PEG molecules. As NTA measures the particle hydrodynamic diameter of the particle, the measured diameter of both exosome samples obtained by TEM was smaller than the NTA analysis measured.

Figure 3C:
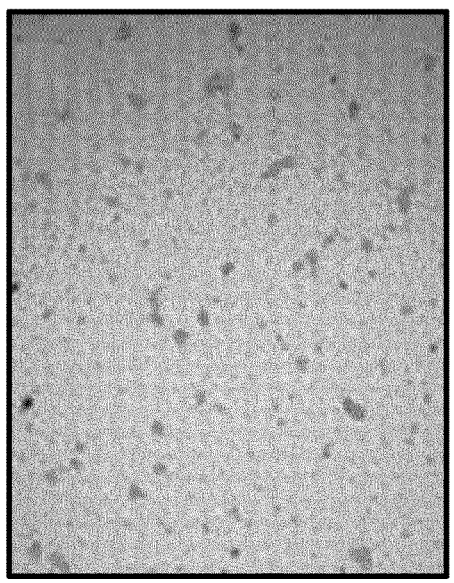
FIGS. 3A-3F are a series of transmission electron microscopy images of PEGylated and unPEGylated exosomes.
Figure 3F:
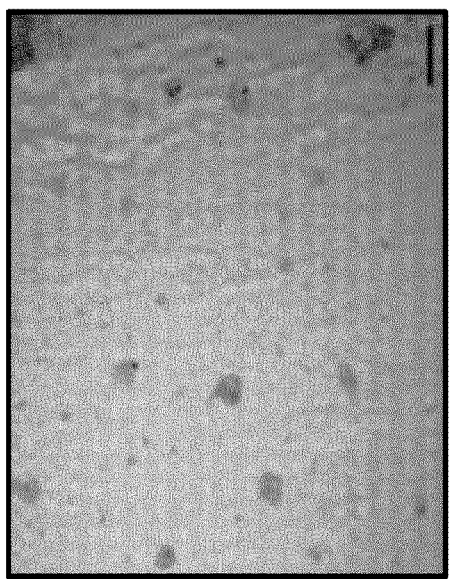
Figure 3B:
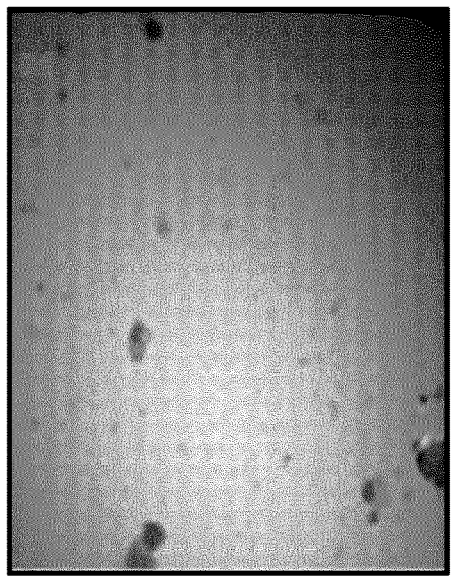
Figure 3E:
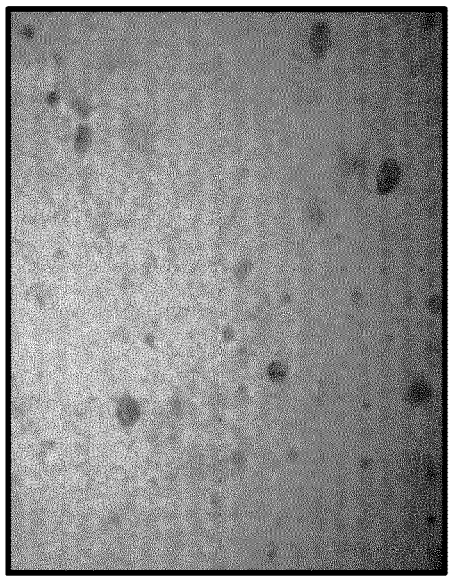
Figure 3A:
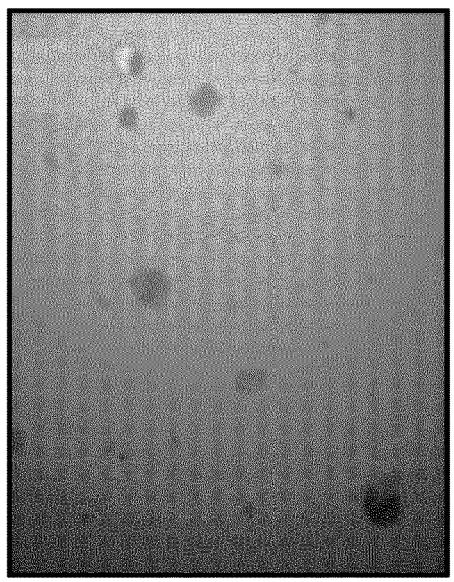
Figure 3D:
Figure 4A:
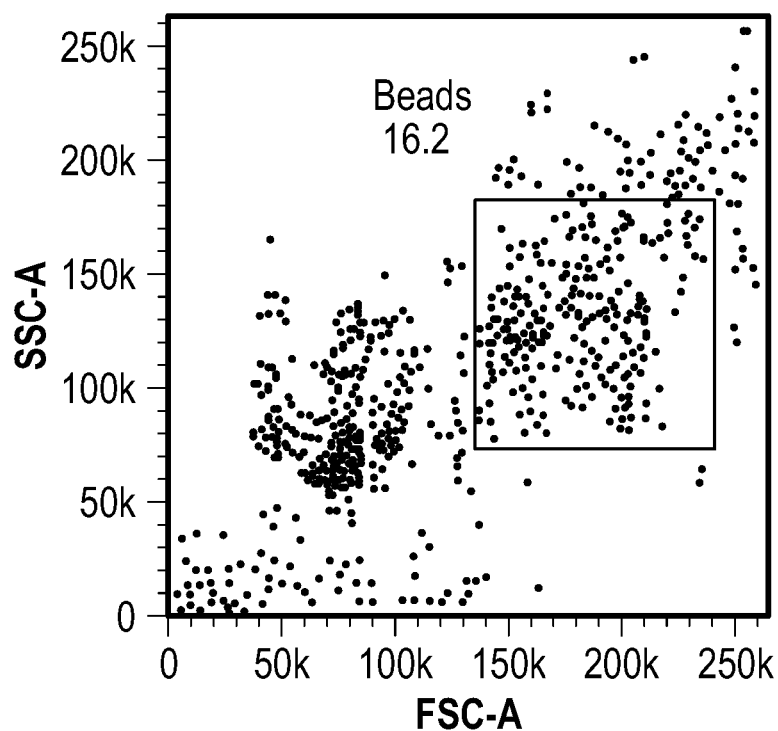
FIGS. 4A-4E is a series of flow cytometry graphs showing labelling of MSCs and exosomes with Far-Red dye.
Figure 4B:
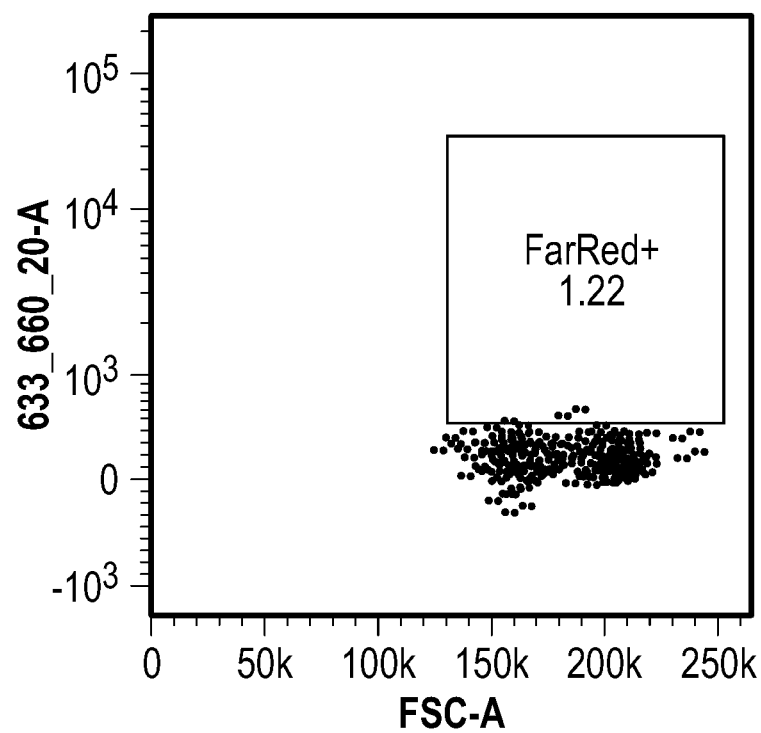
Figure 4C:
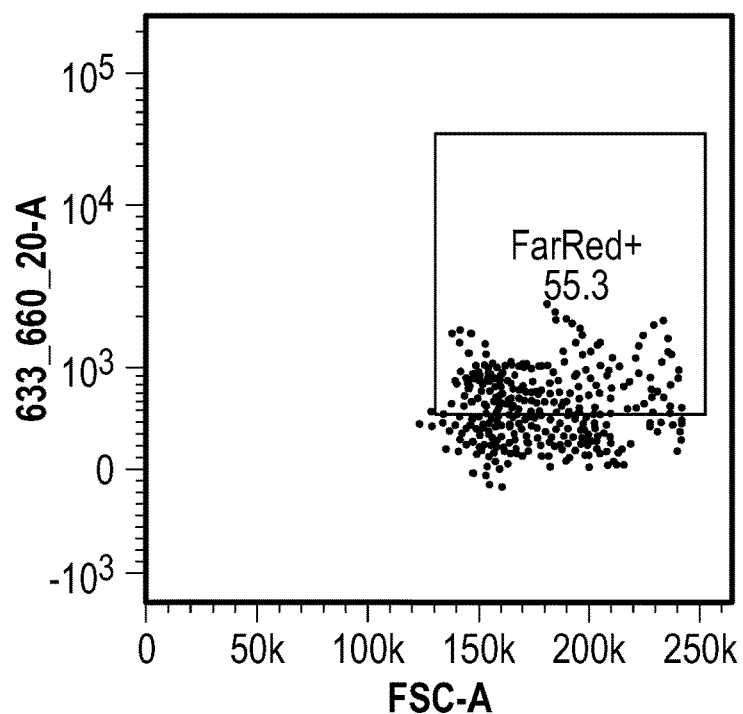
Figure 4D:
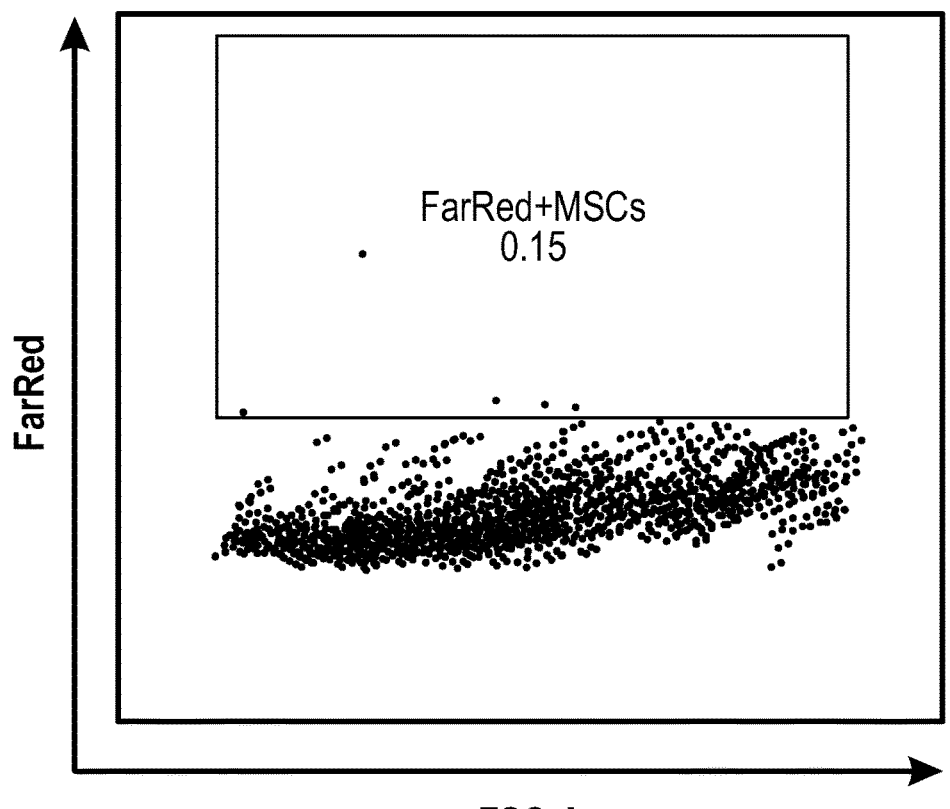
Figure 4E:
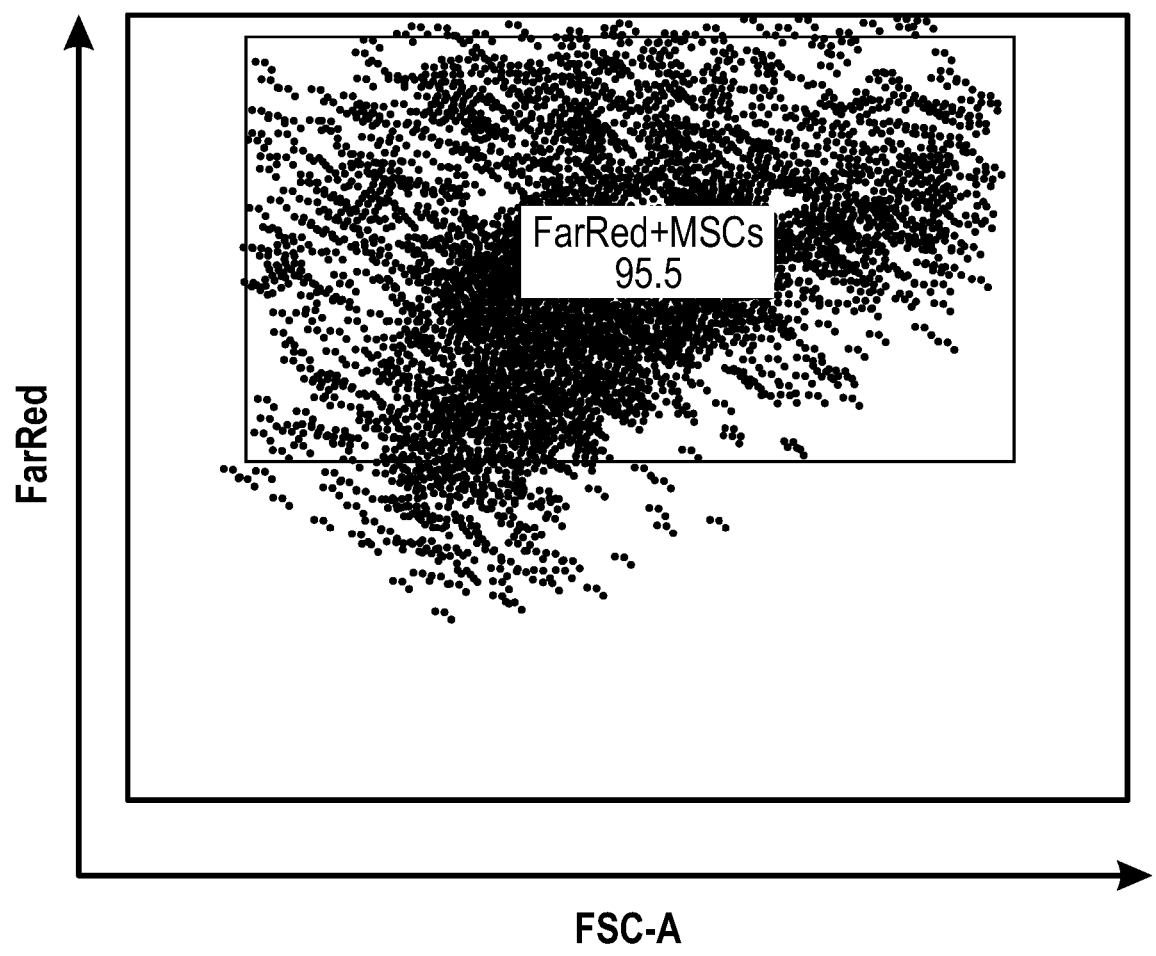

As indicated by the NTA analysis, the mean size of PEGylated exosomes was slightly higher than of unPEGylated exosomes. This size difference is attributed to incorporation of PEG molecules into the surface of the exosomes. Additionally, the zeta potential distribution was measured using a Litesizer 500. The surface charge was measured multiple times and the zeta potential of unPEGylated exosomes was about −16.5 mV and the PEGylated were about −2.6 mV (FIGS. 2A&B). The y axis shows the relative frequency which gives a probability of a particular charge recorded over a particular time period—in this case the exosome charge was recorded a 1000 frames per minute. This is a clear indication that exosomes have been effectively PEGylated and the presence of PEG molecules on the membrane of exosomes nearly neutralised the surface charge. Furthermore, as exosome samples required an additional ultracentrifugation step to remove excess PEG molecules, the actual particle count after the isolation of exosomes may be higher than the number obtained after the PEGylation procedure. TEM analysis of immunogold labelled exosomes samples confirmed the presence of CD63 and TSG-101 markers (FIG. 3) and most of the exosomes were under 100 nm size. FIGS. 3A-3F shows transmission electron microscopy (TEM) images of immunogold labelled (CD63 & TSG 101) exosomes (PEGylated and unPEGylated) (black line, 100 nm). Both FIGS. 3A and 3B represent control group secondary only exosomes, unPEGylated and PEGylated respectively; FIG. 3C represents PEGylated CD 63 exosomes; FIG. 3D represents unPEGylated CD 63 exosomes; FIG. 3E represents PEGylated TSG 101 exosomes; and FIG. 3F represent TSG 101 unPEGylated exosomes. However, the number of CD63 and TSG-101 labelled PEGylated exosomes were markedly less than unPEGylated exosomes but did not show any observable change in the morphology. This might be an indication of effective PEGylation of exosome surface which prevented antibodies from binding their respective antigen. Additionally, the labelling status of both MSCs and exosomes with Far-Red dye was confirmed by the flow cytometry analysis (FIG. 4). FIGS. 4A-E show detection of Far-Red+ MSCs and bead conjugated exosomes by flow cytometry. FIGS. 4A-4C show images of Far-Red+ exosome coated beads, and FIGS. 4D and 4E show Far-Red positive MSCs (gated population). FIG. 4A indicates the bead population (gated population) and FIGS. 4B & 4C show the gated population for Far-Red+ exosome-coated beads.

We thus effectively modified the surface of human bone marrow-derived exosomes by a simple incubation method with low-molecular-weight DSPE-PEG. We used DSPE-PEG (i.e. PEG with a cross-linked lipid) for this experiment to incorporate the lipid portion to the bi-layer of exosomes to anchor the polymer.

In this example, we adopted "post-insertion" methods, used to PEGylate pre-formed liposomes (Nag et al., 2013), to anchor the polymer to the exosome surface after isolating exosomes by ultracentrifugation. In this method, we mixed fluorescently labelled exosome suspension with a certain concentration DSPE-PEG to allow incorporation of PEG to the exosome membrane. In liposomal preparations, samples are usually incubated at a higher temperature to achieve faster and maximum insertion of PEG. However, higher temperature conditions are not compatible with exosomal preparations, so we performed PEGylation procedures at 37° C. The PEGylated and unPEGylated exosomes were characterized by different methods and our results indicate that exosome surface has been modified by PEG in the PEGylated samples as indicated by the increase in mean hydrodynamic diameter, nearly neutralised surface charge and decreased TSG 101 and CD 63 positive exosomes compared to unPEGylated exosomes.

Confocal fluorescent microscopic analysis of the samples clearly shows that the fluorescent Far Red stained PEGylated exosomes were able to internalise into the epithelial cells underlying the mucus layer at less than half the dose of the non-PEGylated control exosomes. This is a highly significant improvement and the improved efficiencies will result in a huge reduction in stem cell culture volumes required to produce exosome treatments. The localisation of the exosomes to the areas surrounding the cell nuclei is also apparent which is where the cell's protein translation machinery is located i.e. on ribosome lining the endoplasmic reticulum. The degree of cell uptake is notable considering that smaller sized viral vectors can become completely trapped in these mucus layers. The invention hence envisages that modified exosomes will be capable of modulating gene expression—for example the introduction of only approx. 100 microRNA molecules are required to provide detectable changes in a cell. Similarly, protein producing mRNA transcripts in a cell only average approx. 40 transcripts in the case of the CFTR protein, which is also easily obtainable with the exosome internalisation into target cells demonstrated by the invention.

Referring to FIG. 5, the mucus penetration and cell internalisation experiments demonstrate the ability of surface modulated extracellular vesicles, particularly exosomes, to pass through mucus and enter the apical cells. The nucleus of the cells are coloured purple and the cell membranes can be identified from the tight junctions, coloured green. It is clear that the red dots, namely the exosomes, have penetrated the cells and are clustered around the nuclei. Thus this ability of PEGylated exosomes has been demonstrated.

Figure 5A:
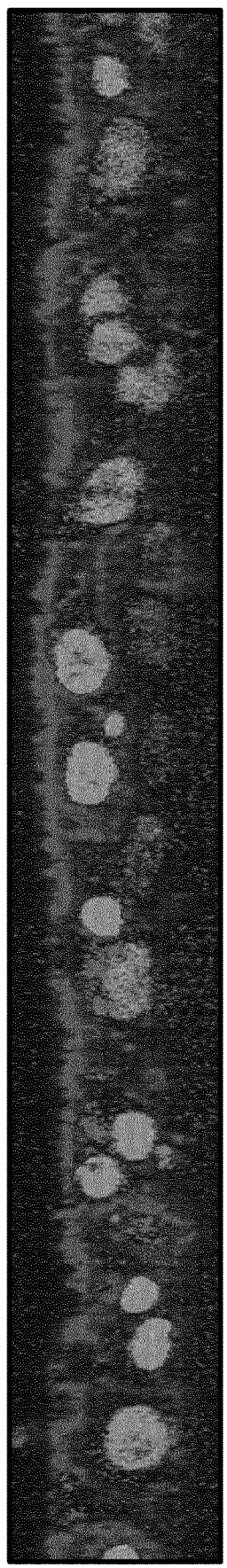
FIGS. 5A-5C are confocal microscopy images of treated and untreated exosomes that have entered into cystic fibrosis bronchial epithelial cells having first penetrated the mucus layer in air-liquid-interface culture.
Figure 5B:
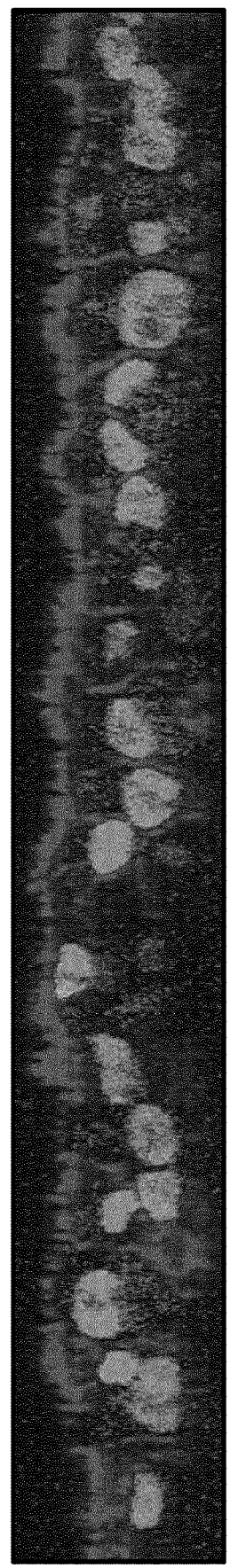
Figure 5C:
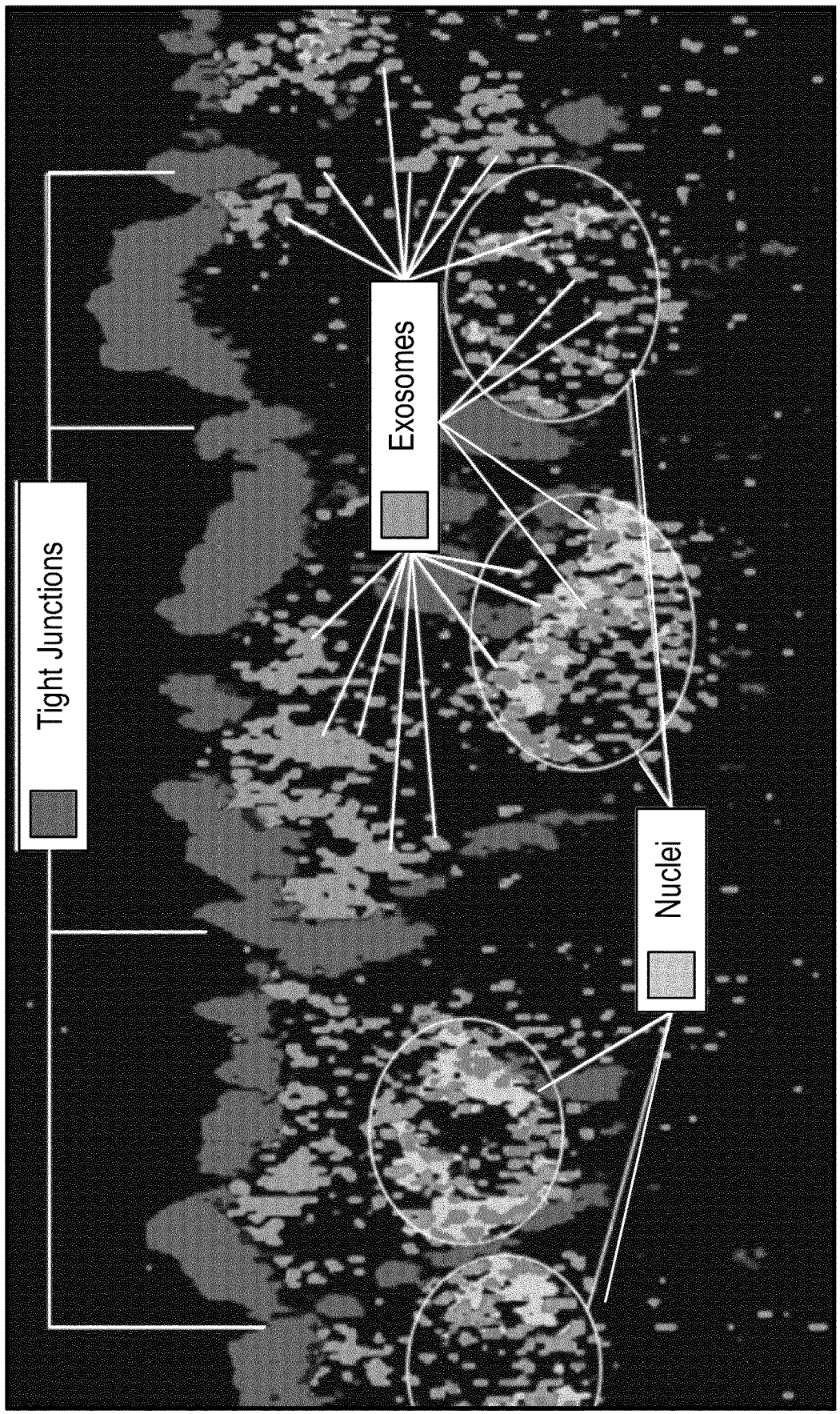

FIGS. 5A-5C are confocal microscopy images of well-differentiated Cystic Fibrosis bronchial epithelial cell cultures. 25 μl of exosomes were applied to the surface of the mucus layers overlying the apical cell surfaces prior to washing, fixing and staining of the samples. For FIG. 5A 3.05×10$^8$ exosomes in 25 μl of PSB (the exosomes treated to be densely coated with DSPE-PEG2000 and a surface charge of −2.5 mV) were applied to surface of the mucus layer. For FIG. 5B 6.63×10$^8$ exosomes in 25 μl of PSB (the exosomes being untreated exosomes, having no surface modification and a surface change of −19.5 mV) were applied to the surface of a mucus layer. As seen comparable mucus penetration and cell internalisation of treated exosomes was achieved with less than half of the applied exosomes. FIG. 5C is a labelled close up image showing exosomes in the apical compartments of epithelial cells and localised about the nuclei (endoplasmic reticulum and ribosomal protein translation machinery).

The surface engineered exosomes may be of beneficial therapeutic use when delivered without any genetic modification of their contents or genetic modification of the parent cells can optimize the exosomes contents for delivery into the targeted cells and the treatment of specific diseases. Further studies of the kinetics of mucus diffusion and cell internalization are planned as the speed of delivery is an important consideration that will influence the extent of intracellular delivery in vivo. The surface modified exosomes show accelerated uptake which is of significant benefit to avoid mucociliary clearance mechanisms and this may be demonstrated by comparing the permeation kinetics of equal 'doses' of surface modified and unmodified exosomes applied to the mucosal surface in a variety of concentrations with real time confocal microscopy video analysis.

The required doses of exosomes that need to be delivered by aerosol can also be approximately extrapolated from the in vitro mucus penetration experiments. A known number of exosomes were applied to a known surface area of mucus covered epithelial cells (60 mm 2) and very significant epithelial cell uptake was demonstrated. Some key assumptions are;
1. The viscosity of a given concentration of exosome formulation and achievable aerosol output at this viscosity;
2. That surface engineered exosomes will penetrate relatively quickly through the mucus layer which is reasonable given that concentration will greatly influence this via concentration driven diffusion and relatively very dilute exosome formulations were employed in the pilot studies (0.00063928% v/v of surface modified exosomes).

The following table illustrates the exosome loading capacity of aerosol droplet of various sizes @ a 1% w/v concentration of exosomes:

| Droplet MMAD μm | Droplet radius | Volume Droplet μm3 | Volume Droplet microliters | Exosome Diameter μm | Exosome Volume μm$^3$ | Exosome volume microliters | # Exosomes @ X % loading (e.g. 6% est @2 cP, 12%, cP est @ ~5.2) per droplet |
|---|---|---|---|---|---|---|---|
| 10 | 5 | 523.6 | 5.236E−07 | 0.1 | 0.000524 | 5.24E−13 | 9992.37 |
| 7 | 3.5 | 179.59 | 1.7959E−07 | 0.1 | 0.000524 | 5.24E−13 | 3427.29 |
| 6 | 3 | 113.1 | 1.131E−07 | 0.1 | 0.000524 | 5.24E−13 | 2158.40 |
| 5 | 2.5 | 65.45 | 6.545E−08 | 0.1 | 0.000524 | 5.24E−13 | 1249.05 |
| 4.5 | 2.25 | 47.71 | 4.771E−08 | 0.1 | 0.000524 | 5.24E−13 | 910.50 |
| 4 | 2 | 33.51 | 3.351E−08 | 0.1 | 0.000524 | 5.24E−13 | 639.50 |
| 3 | 1.5 | 14.14 | 1.414E−08 | 0.1 | 0.000524 | 5.24E−13 | 269.85 |
| 2 | 1 | 4.19 | 4.19E−09 | 0.1 | 0.000524 | 5.24E−13 | 79.96 |
| 1 | 0.5 | 0.52 | 5.2E−10 | 0.1 | 0.000524 | 5.24E−13 | 9.92 |
| 0.1 | 0.05 | 0.000524 | 5.24E−13 | 0.1 | 0.000524 | 5.24E−13 | 0.01 |
| | | | X % = | | | | 1% |

For example, in the case of Cystic Fibrosis, the targeted lung area is the total airway surface area from trachea to bronchioles which is approx. 2,471+/−320 cm$^2$ in the adult human lung. This surface area could be treated via a deposited aerosol volume of approx. 70 microlitres of a 1% w/v exosome formulation.

The surface area of the distal lung is far greater with approx. 18 times more alveolar cells than bronchial epithelial cells and targeting this area is desirable for treating emphysema and idiopathic pulmonary fibrosis for example. The cellular uptake of exosomes is expected to be far higher in these regions of the lung due to the lack of mucus barrier.

In conclusion, we have shown that exosomes were effectively PEGylated using lipid-conjugated PEG by a simple incubation method and the resultant exosomes penetrated viscous CF mucus and were internalised into epithelial cells, demonstrating a pulmonary exosome-based gene therapy platform or simply as therapeutically useful exosomes for treating inflammatory lung diseases.

PEGylation also results in a sterically stabilised formulation of exosomes that has significantly reduced viscosity compared to non-PEGylated formulations. Generation of an aerosol containing such exosomes possessing a dense hydrophilic corona to shield from hydrophobic interaction induced agglomeration is hence facilitated, meaning that aerosols for delivery of exosomes at an acceptable and useful concentration are now facilitated and enabled at higher concentrations. The pegylated exosomes demonstrate improved mucus penetration, this property then facilitating their passage through lung mucus to lung tissue, further enhancing the efficacy of the pegylated exosomes in therapeutic applications against lung disease. Lastly, PEGylated monoclonal antibodies and nanoparticles may also display enhanced 'stealth' properties that help them to avoid uptake and clearance by phagocytes such as alveolar macrophages which are present in increased numbers in inflammatory lung diseases.

The invention thus provides coated vesicles e.g. exosomes that can be used in gene therapy for CF, COPD, Adenocarcinoma and other lung conditions.

EXAMPLE 2

The aims of this example were to show the surface modification of exosomes can be effectively achieved and that genetically modified mesenchymal stem cell populations of bioengineered cells, over-expressing CFTR gene can be successfully established.

BT-20 and hMSC Cell Line Culture Techniques

BT-20 cells sourced as BT-20 human epithelial cells from ATCC® HTB-19™ were cultured in DMEM media supplemented with 10% FBS and 100 IU/ml of Penicillin/Streptomycin as complete condition media (CCM). Human Mesenchymal Stem Cells Donor No. 096 were used, the cells were cultured in Gibco's MEM Alpha Medium with 10% FBS and 100 IU/ml of Penicillin/Streptomycin and 1 ng/ml of human basic fibroblast growth factor (bFGF).

The feeding of the cells was done 3 days a week using aseptic technique, which was to remove spent media from culture flask with a pipette and add to waste bottle followed by replenishing of culture flask(s) with appropriate volume of fresh media (supplements included) to the ceiling of the culture flask so that the cell culture (monolayer) is not disturbed by the flow. The flask was then removed from the hood tilting the flask so its lid faced inward and placed in an incubator at 37° C. with 5% $CO_2$. The cells were examined routinely with a light microscope for signs of contamination such as turbidity, cells in suspension, change in media colour, large clumps or particles etc.

For splitting of the cells every 7-10 days and before cells reach 80-90% confluence, the cells were washed with 3-5 ml of PBS ensuring that it was delivered to the opposite side of the flask so as not to disturb the cells, followed by 5 ml of warmed T/E (Appropriate concentration, 37° C.) The flask was then rocked on its axis gently for 30 seconds, ensuring that all cells were covered, and the excess T/E poured off into waste a bottle by a pipette (leaving approx. 1 ml in flask). The cells were incubated with remaining trace of T/E at 37° C. for 3-5 mins, as the cells detached from the floor of the flask. The detached cells were resuspended in 4-6 ml of complete medium (volume depends on cell number expected). The cell suspension was then pipetted up and down with 10 ml pipette to ensure homogeneity and remove to 15 ml falcon. The flasks were incubated at 37° C.

Preparation for EV Free Media

EV free media is a pre-requisite of EV Isolation protocols for purified yield of EVs from cells in culture. This is to eliminate contamination of EV isolates of the cultured cells from microvesicles outside of the experimental setup.

130-140 mls of 20% FBS+Basal Medium (1:5) in an autoclaved sterile glass bottle was prepared and appropriate amount of the above was ultra-centrifuged at 110,000×g for 18 hours, at 4° C. After ultracentrifugation, the supernatant was aspirated carefully onto a fresh 50 ml falcon tube making sure not to disturb the pellet. The supernatant from 50 ml Falcons was filtered onto a fresh autoclaved glass container. To this was added an equal portion of Basal Media to bring to 1:1 proportion, making the total FBS concentration in the above solution to 10%. This yielded 10% EV free media to be used for EV isolation cell culture. The condition media was stored at 4° C. up to 4 weeks supplemented with 100 IU/ml of P/S (or other supplements) before using for EV Isolation protocol.

Cell Culture for EV Isolation and Preparation of EV Rich Condition Media

EVs were isolated according to the MISEV2018 guidelines and further refined protocols (Thery et al., 2006). BT-20 cells were brought to enough numbers 3-4 T-175 $cm^2$ flasks to seed 12×T-175 $cm^2$ T-flasks in EV free media (2×10$^6$ cells/flask). The cells were trypsynized and resuspended in EV depleted media and seeded onto 12×T-175 $cm^2$ T-Flasks in 10 mls of EV depleted media for 24 hours to allow the cells to adhere to the floor of the flask. The media was then replaced with equal amount of fresh EV free media (Condition Media). The flasks were left to incubate for 48 hours.

After 48 hours, conditioned media was then collected from each flask and pooled into 50 ml Falcons and cells in the flasks were trypsynized, a cell count was taken from total cell lysate (Appropriate number of cells were then either passaged/frozen/discarded). EV free media Culture Supernatant was poured from T-Flasks into 50 ml Falcons (4 flasks per 50 ml falcons). Then the 50 mls falcons containing supernatant were brought to centrifuge, to remove cell debris at 300×g for 10 mins, temperature −21° C. The supernatant was then aspirated using 25 ml pipettes, leaving the bottom 2-3 ml residue undisturbed, into fresh 50 ml Falcons respectively. The supernatant then centrifuged at 2000×g for 10 mins at a temperature of −21° C. After centrifugation, the supernatant was collected leaving dead cells pellet within bottom 2-3 ml residue. Then using a 0.2 µm pore size sterile filter and syringe, the top 25 ml of supernatant was aspirated and collected into fresh autoclaved ultra-centrifuge tubes. The filtered condition media was then ultra-centrifuged at 110,000×g for 70 mins at 4° C. in the Hitachi Micro Ultracentrifuge. After ultracentrifugation 1 ml of supernatant was taken from one of the tubes into a 1.5 ml tube and stored at −80° C. (Supernatant Analysis 1). The rest of the supernatant was discarded into waste container without scraping the pellet. The pellet containing EVs was re-suspended with 1 ml of PBS in each UCT and pooled together into a single UCT. This was ultracentrifuged at 110,000×g for 70 mins at 4° C. After ultracentrifugation, 1 ml of supernatant was taken into 1.5 ml Eppendorf from a UCT and stored at −80° C. (Supernatant Analysis 2). The rest of the supernatant was discarded into the waste container without scraping the pellet. 85 µls of sterile PBS was pipetted onto EV containing UCTs and the marked side was scraped off for about 5 mins with 100 µl pipette tip. After 5-8 mins of scraping, all PBS resuspension had been collected. All the residue including bubbles was collect onto a tapered tube for future PEGylation. This was pulse centrifuged for 10 seconds to get rid of bubbles and the supernatant was mixed in LFH with a pipette. 15-20 µls was pipetted into tube (NTA/Zeta) and 10 µls to protein analysis tube. All the isolated EV samples were stored at −80° Celsius. All the steps were performed using aseptic techniques and all the centrifugation steps were performed at −4° C.

Post-Isolation Modification of EVs by DSPE-PEG 2000 (AMINE)

DSPE-PEG (2000) Amine (Avanti Polar Lipids, Inc) was purchased from Sigma Aldrich (Wicklow, Ireland). PEGylated exosomes were prepared based on previously published data on Pegylated liposomal preparation (Kooijmans et al., 2016). A final volume of 1:4 ratio of isolated EV suspension (50 µls) was prepared by mixing concentrated EV suspension with PBS in a plastic or glass tube for samples 1, 2 and 6 and samples 4, 5 and 7 respectively. To this an equal ratio (or desired percentage) of 1:1 (ug protein: ug protein) DSPE-PEG 2000 Amine (10 mg/ml) was added which was kept for incubation at 37° C. for 1 hr, by placing the EV samples in a temperature controlled tube holder on top of a swaying rocker at low speeds to prevent clumping of PEG molecules or exosomes. After incubation, the EV-PEG suspension was introduced into 16-20 mls of PBS in an Ultracentrifuge tube. Ultracentrifugation was performed at 110000×g for 70 mins to wash off unbound PEG molecules. The EV pellet was then re-suspended in 75 µl of PBS and stored in appropriately sized glass containers with lid, and from this aliquot 20 µls for Zeta analysis in separate containers. This was stored at −80° C. or −20° C. for sample 1, 2, 6 and samples 4, 5, 7 respectively.

Nanoparticle Tracking Analysis (NTA)

Both PEGylated and unPEGylated exosome samples were analysed via Nanoparticle Tracking Analysis (NTA) (Malvern UK) using a NanoSight NS500 system running NTA version 3.2 using optimised and validated protocols (Maguire et al., 2017, Hole et al., 2013, Gerlach et al., 2017). All the samples were analysed using a NanoSight NS 500 equipped with a 405 nm laser and 430 nm long pass filter. All samples were stored on wet ice prior to analysis. Dilutions for NTA were made up in D-PBS [—$MgCl_2$, —$CaCl_2$)] (Gibco) that was certified particle free by NTA immediately prior to measurement. Samples were pipetted before loading to ensure adequate mixing and the breaking up of weakly bound EV clusters. Each sample was diluted manually in D-PBS to obtain an optimum particle concentration suitable for NTA (between 10 and 100 particles per field of view), with each dilution factor being recorded in the automatically generated reports. A total of six×60 second videos were recorded for each EV sample and the detection threshold during analysis was selected by the operator, to ensure that only distinct nano-objects were analysed and to ensure that artefacts were removed. As NTA measures the particle hydrodynamic diameter, i.e., the size of the solvated particle that is approximated as being spherical, the measured diameters may be larger than those obtained by electron microscopy (EM) based techniques. In general, exosomes possess diameters in the 30-150 nm size range. All samples were stored on dry ice prior to analysis. Dilutions for NTA were made up in DPBS buffer (Gibco) that was certified particle free by NTA immediately prior to measurement. Samples were vortexed briefly before loading to ensure adequate mixing and breaking up of weakly bound exosome clusters. Each sample was diluted manually in PBS to obtain an optimum particle concentration suitable for NTA (between 20 and 70 exosomes per field of view), with each dilution factor for being recorded in the automatically generated reports. A total of six×60-second videos were recorded for each exosome sample and the detection threshold during analysis was selected to ensure that only distinct nano-objects were analysed, to ensure that artefacts were removed.

Zeta Potential Measurement

The zeta potential of EVs was measured using a Litesizer 500, a light-scattering instrument for particle analysis (Litesizer™ 500, Anton Paar Ltd, UK). The zeta potential was measured by diluting the EV samples PEGylated/Non-PEGylated with PBS in 1:100 or 1:16 (EV Sample-PBS) in an Anton Paar Calliope Core Omega Cuvette using Smoluchowski approximation with Debeye Factor of 1.5 with equilibration time of 1 minute and target temperature of 25° C. with water as dispersion medium selected in the software as there was no option for PBS as dispersion medium. The samples intended for Zeta analysis were thawed in ice box/container and brought to the zeta analysis lab, where the samples were stored at 4° C. and taken out as used for the analysis, the dilution was done in the original tube containing PEGylated or Non-PEGylated EVs, just before the sample was to be added to the cuvette. The cuvette was washed using a syringe first time with DI-water and then three times with sterile PBS and then the sample was added using a sterile syringe. The maximum and minimum load capacity for each cuvette was 350 μls and 300 μls respectively. The concentration of particles in each dilution was high enough to provide meaningful measurements by generating a peak intensity for most of the zeta potential distribution of the particles (outliers included in the results).

Lentiviral Transduction of hMSCs with EGFP-Gene Constructs

Lentiviral transductions were performed on hMSCs Donor #096. The introduction of EGFP-CFTR and EGFP-NEG control was done to express amplified CFTR protein in the EGFP-CFTR transduced cells for production of CFTR gene and mRNA encapsulated RNAs which are to be further characterized once a viable population is reached. The transductions were completed using spin protocol.

hMSCs were split as normal and resuspended in 5 ml of complete media. The resuspended MSCs were pelleted by centrifuging at 1000×g for 4 mins after which complete media supernatant was discarded. The cells were resuspended gently in 5 ml basal media (no FBS, no antibiotic) and a cell count was done.

1×10$^6$ (or approximate) cells were further diluted in approx. 5 ml of basal media in separate 50 ml falcon tubes for each EGFP Lentivirus, positive control and negative control (receives no lentivirus). To each Experimental and Positive Control MOI of 3-4 (approximately 18 μls) of lentivirus was added. The negative control received no lentivirus and all the 50 ml falcon tubes were centrifuged for 90 mins at 2000×g at 37° C. after centrifugation discarded the media and re-suspend cell pellet again in complete media. The cells were then seeded onto appropriately sized T-Flasks (T175 or T-75) depending on the number of cells transduced and incubated in completed media supplemented with bFGF (1 ng/ml). After 48 hr incubation, the media was changed to complete media with bFGF and supplemented with of 4 μg/ml puromycin to select the transduced cells for 7-14 days, after which the cells were changed to normal complete media without puromycin. The cells were split every 7-10 days after the transduction was done.

Results

For the initial experiments, BT-20 Human Breast Cancer cell line was used for their high proliferative capacity and ease of culture. The cells were brought to 12×T-175 cm$^2$ T-Flasks. The EVs were isolated from the above using differential centrifugation followed by two ultracentifugation steps according to MISEV guidelines following most widely used and proven methods and then different methods were implemented for EV characterization including size distribution through Nanoparticle Tracking Analysis and Surface Charge Analysis through Zeta Potential studies using Litesizer™ 500 instrument. Both the PEGylated and non-PEGylated EVs were characterised using established protocols and techniques to the best-known practice.

EVs isolated from BT-20 cells were characterized using different methods to quantify their size and to measure their surface charge. We isolated exosomes using differential ultracentrifugation as this method remains the most widely used standard method to isolate exosomes from different biological fluids or cell culture supernatants (Chia et al., 2017, Thery et al., 2006). The nanoparticle tracking analysis (NTA) of both PEGylated and unPEGylated exosomes revealed that NTA Analysis is not a viable option for diluted fractions of PEGylated EVs. PEGylated EVs might be subject to surface modification due to interaction with plastic surfaces in Ultracentrifuge Tubes or due to degradation in plastic containers, for this we used glass containers for storing PEGylated EV fractions for sample 4, 5 and 7 and performed Zeta analysis for characterization of those samples instead of NTA analysis.

BT-20 Cell Culture Overview

All parameters relating to cell culture are briefly presented as below in Tables 1a and 1b, showing values of cell counts, protein concentration of EV-Isolates, DSPE PEG:Protein percentage for PEG treatment, Zeta potential and NTA readings for isolate EV Fractions. For NTA analysis readings, the values for Sample 1 are unreliable due to low particle counts per frame (i.e. <3 particles per frame). This also applies to the Mode NTA After PEG for samples 2 and 6. <10 particle counts per frame were also noted for the Mode NTA Before PEG for samples 3, 4, and 7. However, these results fulfil quality assessment criteria. All data is represented as cells/ml for cell count, μls for volume, mV for Zeta potential and nM for mode size distribution for NTA analysis results.

TABLE 1a

| Sample No | Isolation Date | Total Cell Count/ml | Dead Cells/ml | Lysate Volume (ml) | Total Cells from 12 T-175 cm² Flasks on EV harvest day | Total Viable Cells | Protein Conc. (µg/ml) |
|---|---|---|---|---|---|---|---|
| 1 | 14-Mar | 1.37E+06 | 5.10E+04 | 25 | 3.41E+07 | 3.29E+07 | 208.33 |
| 2 | 15-Mar | 1.61E+06 | 7.10E+04 | 25 | 4.01E+07 | 3.84E+07 | 391.67 |
| 3 | 21-Mar | 3.20E+06 | 2.70E+04 | 13 | 4.16E+07 | 4.13E+07 | 2268.75 |
| 4 | 28-Mar | 2.51E+06 | 2.60E+04 | 18 | 4.54E+07 | 4.48E+07 | 408.33 |
| 5 | 29-Mar | 2.39E+06 | 9.20E+04 | 19 | 4.53E+07 | 4.36E+07 | 187.50 |
| 6 | 4-Apr | 2.15E+06 | 2.95E+05 | 22 | 4.74E+07 | 4.09E+07 | 263.46 |
| 7 | 5-Apr | 2.23E+06 | 1.19E+05 | 22 | 4.90E+07 | 4.64E+07 | 125.00 |

TABLE 1b

| Sample No. | Prot. In µg in EV sample | PEG volume for 100% prot. Conc. (µls) | PEG:Protein (%) | DSPE PEG Volume used to PEGylate (µls) | Average pre-PEG ZP (mV) | Mode NTA before PEG (nM) | Mode NTA after PEG |
|---|---|---|---|---|---|---|---|
| 1 | 10.42 | 1.04 | 100% | 1.04 | −14.55 | 106.5 | 93 |
| 2 | 19.58 | 1.96 | 50% | 0.98 | −11.62 | 110.5 | 97 |
| 3 | | | | | −0.42 | 156 | |
| 4 | 9.38 | 1.63 | 50% | 0.82 | −12.93 | 120 | |
| 5 | 16.33 | 0.94 | 100% | 0.94 | −10.48 | 96 | |
| 6 | 13.17 | 1.32 | 75% | 0.99 | −0.63 | 112 | 117 |
| 7 | 6.25 | 0.63 | 150% | 0.94 | −15.85 | 93.5 | |

NTA Analysis:

Tables 2a and 2b set out below show values of replicate readings for NTA analysis as: Mode particle size distribution (nm), Total particle concentration and Particle concentration between 30-150 nm range in NPs/mL for isolated EV-fractions from BT-Cells, cultured in 12×T-175 cm T-Flasks following EV-isolation protocol (MISEV). Data is represented as Mean and SEM. Sample 1 and all the PEGylated Samples provided unreliable data as <3 particle counts per frame were recorded, which does not meet NTA quality assessment criteria. Samples 2 and 3 provided <10 particle counts were frame, though their measurement passes the quality assessment criteria. Sample 7 also has a particle count of <10 per frame on SEM, but again passes the quality assessment criteria.

TABLE 2a

| | | Mode Particle Size (NM) | |
|---|---|---|---|
| Sample # | Replicates | Mean | SEM |
| 1 | 6 | 106.5 | 9 |
| 2 | 6 | 110.5 | 5 |
| 3 | 4 | 156 | 43.5 |
| 4 | 6 | 120 | 26 |
| 5 | 6 | 96 | 3.5 |
| 6 | 6 | 112 | 5 |
| 7 | | 93.5 | 6 |
| PEGylated Sample 1 | 6 | 93 | 11.5 |
| PEGylated Sample 2 | 6 | 97 | 4.5 |
| PEGylated Sample 3 | 6 | 117 | 23.5 |
| 100 nm NIST | 6 | 106 | 1 |
| 30 nm AUNPs | 22 | 34.5 | 0.5 |
| D-PBS Control | 28 | 100 | 11 |

TABLE 2b

| | Total Particle Concentration (NPs/mL) | | Particle Concentration between 30-150 nm (NPs/mL) | |
|---|---|---|---|---|
| Sample # | Mean | SEM | Mean | SEM |
| 1 | 9.50E+08 | 1.84E+08 | 5.81E+08 | 1.39E+08 |
| 2 | 1.06E+11 | 6.67E+08 | 7.30E+10 | 1.75E+09 |
| 3 | 2.66E+09 | 1.83E+00 | 1.08E+09 | 4.08E+08 |
| 4 | 3.25E+09 | 1.88E+08 | 1.11E+09 | 1.43E+08 |
| 5 | 2.72E+10 | 1.96E+09 | 1.76E+10 | 9.96E+08 |
| 6 | 4.78E+10 | 2.57E+09 | 3.65E+10 | 2.10E+09 |
| 7 | 5.68E+09 | 5.78E+08 | 3.34E+09 | 3.14E+08 |
| PEGylated Sample 1 | 8.20E+08 | 1.63E+08 | 7.36E+08 | 1.64E+08 |
| PEGylated Sample 2 | 1.40E+09 | 2.04E+08 | 1.08E+09 | 1.58E+08 |
| PEGylated Sample 3 | 7.52E+08 | 1.01E+08 | 3.60E+08 | 1.15E+08 |
| 100 nm NIST | 1.70E+10 | 1.12E+09 | 1.15E+10 | 5.59E+08 |
| 30 nm AUNPs | 6.62E+10 | 1.44E+09 | 6.22E+10 | 1.64E+09 |
| D-PBS Control | 8.54E+05 | 8.54E+05 | 6.53E+06 | 6.72E+05 |

Table 2b

1. Calibration of the system before each day of analysis was verified using a 100 nm NIST polystyrene nanosphere size standard (100 nm NIST) and a 30 nm gold citrate nanoparticle (30 nm AuNPs).
2. All samples in the table below passed quality assessment criteria as discussed.
3. Samples #1, PEGylated Sample #1, PEGylated Sample #2 & PEGylated Sample #6 provided unreliable results as a consequence of low particle counts per frame (i.e. <3 particles per frame, which is classified as 'particle-free'). For this reason, they did not pass quality assessment criteria.
4. Samples #3 & #4 provided a low particle count per frame (i.e. <10). Though, their measurements passed quality assessment criteria.

5. Samples #7 provided a SEM of their respective particle counts per frame reaching <10. Though, their measurements passed quality assessment criteria, this may be cause for minor consideration in their concentration measurement and should be reported.

Figure 6A:
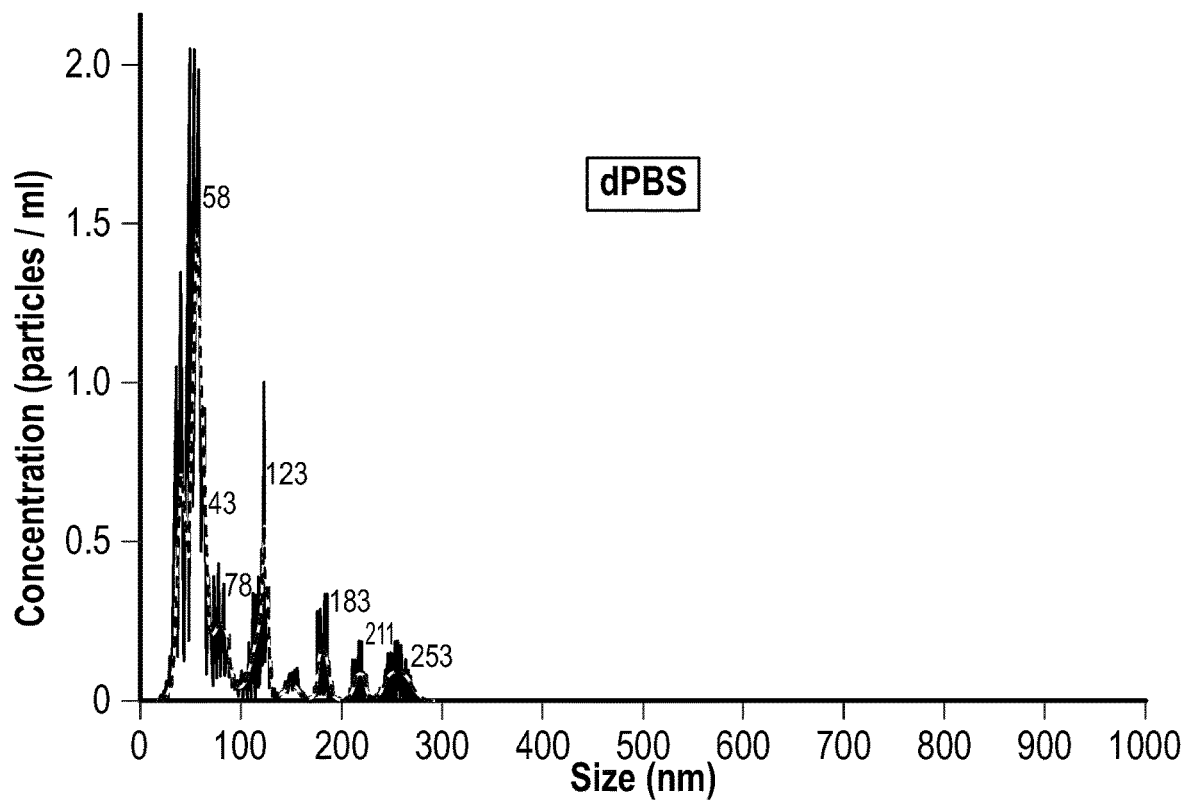
FIGS. 6a and 6b are nanoparticle tracking analysis readings for dPBS and nm gold (Au) nanoparticles as controls.
Figure 6B:
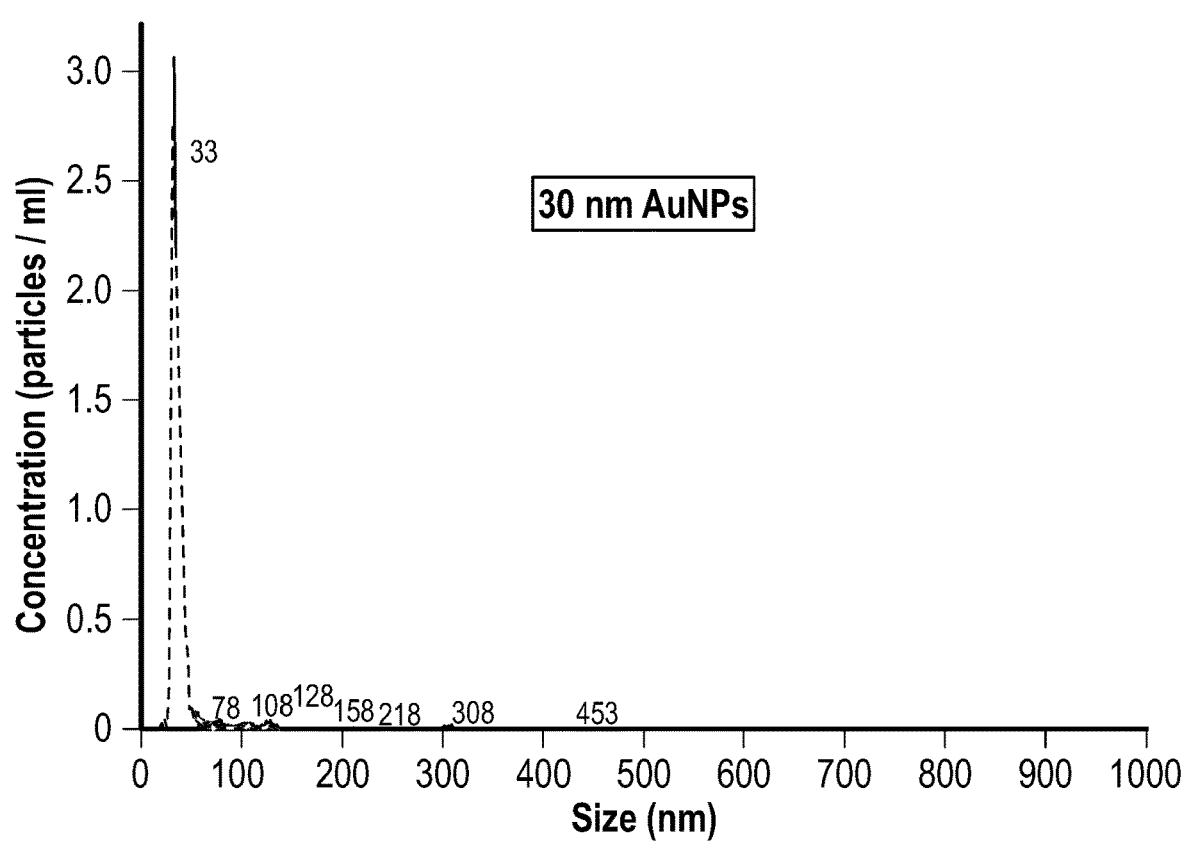

Controls:

FIGS. 6a and 6b show nanotracking analysis (NTA) reading for dPBS and 30 nm Gold (Au) nanoparticles as controls for particle size (nm) at X-axis and particle concentration distributions (particles/ml) at Y-axis. dPBS shows less than 1 count per frame i.e. particle free solution as expected and AuNPs show a definite peak with mean size of 34±0.5 nm and pass the quality control test. Table 3 below provided the respective values in mean and SEM.

TABLE 3

| Sample # | Replicates | Mean Particle Size (nm) Mean | SEM | Total Particle Conc. (NPs/mL) MEAN | SEM | Particle Conc. between 30-150 nm (NPs/mL) Mean | SEM |
|---|---|---|---|---|---|---|---|
| 30 nm AuNPs | 22 | 34.5 | 0.5 | 6.62E+10 | 1.44E+09 | 6.33E+10 | 1.64E+09 |
| D-PBS Control | 28 | 100 | 11 | 8.90E+06 | 8.54E+05 | 6.42E+06 | 6.72E+05 |

Sample 1

Figure 7A:
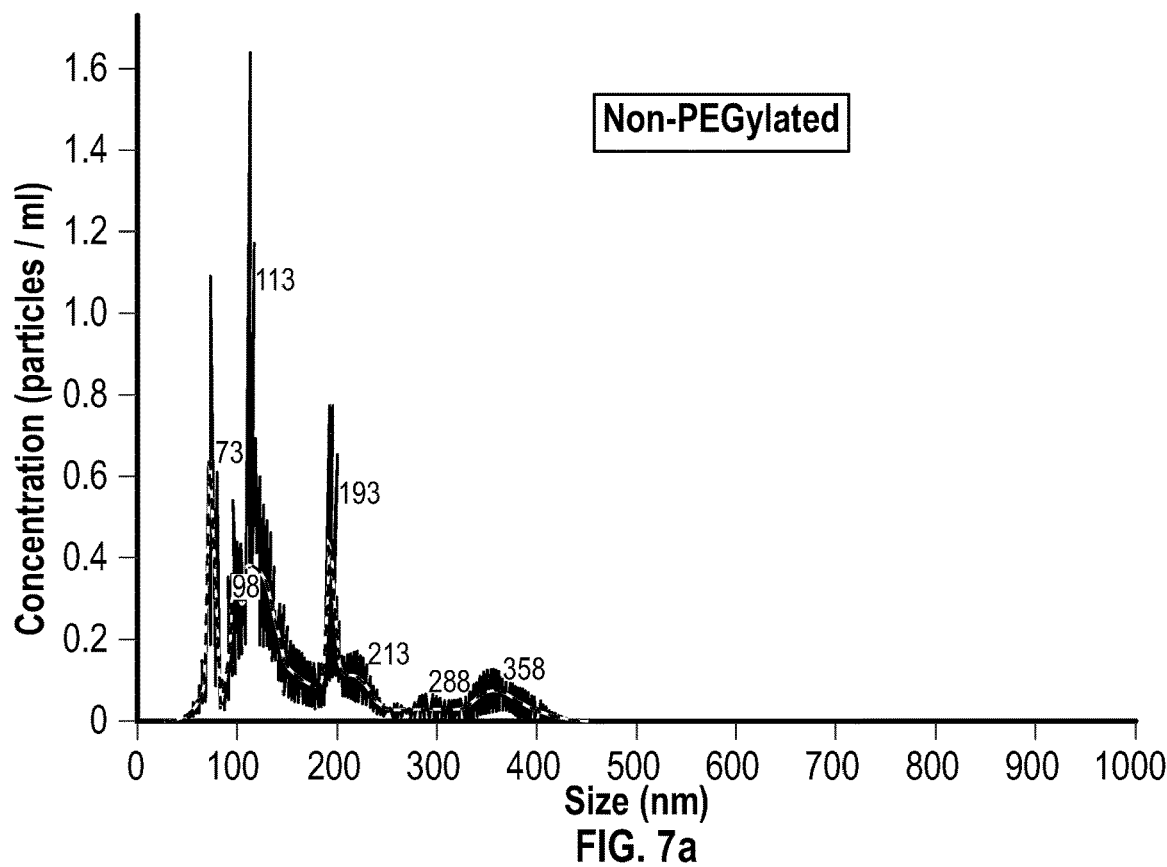
FIGS. 7a and 7b are nanoparticle tracking analysis readings for Sample 1.
Figure 7B:
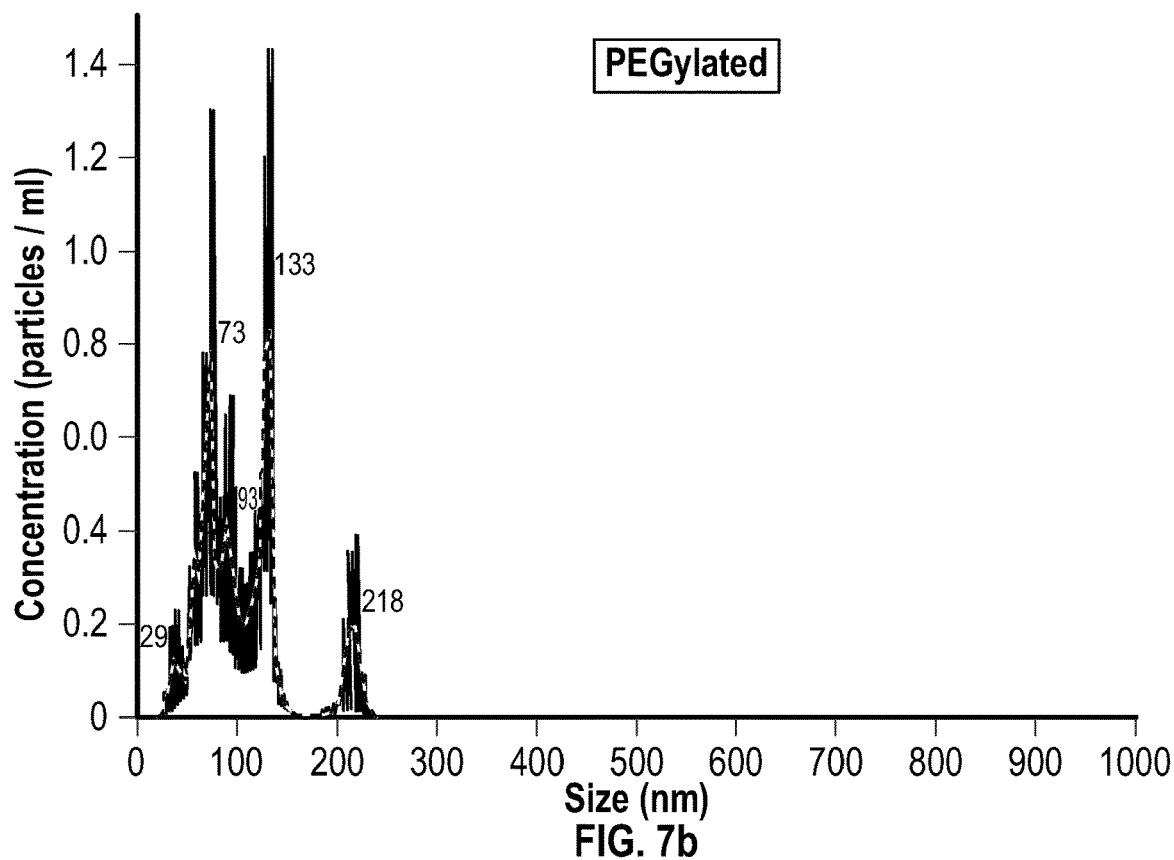

FIGS. 7a and 7b show nanoparticle tracking analysis distribution for sample-1. EV samples for particle size (nm) at X-axis and particle concentration distributions (particles/ml) at Y-axis. Both the non-PEGylated and PEGylated samples had less than 3 counts per frame and didn't pass the quality control test for NTA analysis i.e. particle free solution. The mean size distribution and particle concentration is set out in Table 4a below and the total cell count and particle distribution of the source cell lysate is set out in Table 4b. Data is presented in Mean SEM, particles/cell and particles/given volume respectively.

TABLE 4a

| Sample 1 | Replicates | Mean Particle Size (nm) Mean | SEM | Total Particle Conc. (NPs/mL) MEAN | SEM | Particle Conc. between 30-150 nm (NPs/mL) Mean | SEM |
|---|---|---|---|---|---|---|---|
| Non-PEGylated | 6 | 106.5 | 9 | 9.50E+08 | 1.84E+08 | 5.81E+08 | 1.39E+08 |
| PEGylated | 6 | 93 | 11.5 | 8.20E+08 | 1.63E+08 | 7.36E+08 | 1.64E+08 |

TABLE 4b

| Viable Cells | Total Particle conc. (NPs/85 μls) | 30-150 nm Particles (NPs/85 μls) | Total Particles/Cell | Total Particles (30-150 nm)/Cell |
|---|---|---|---|---|
| 3.37E+07 | 8.1E+07 | 4.9E+07 | 2 | 2 |

Sample 2

Figure 8A:
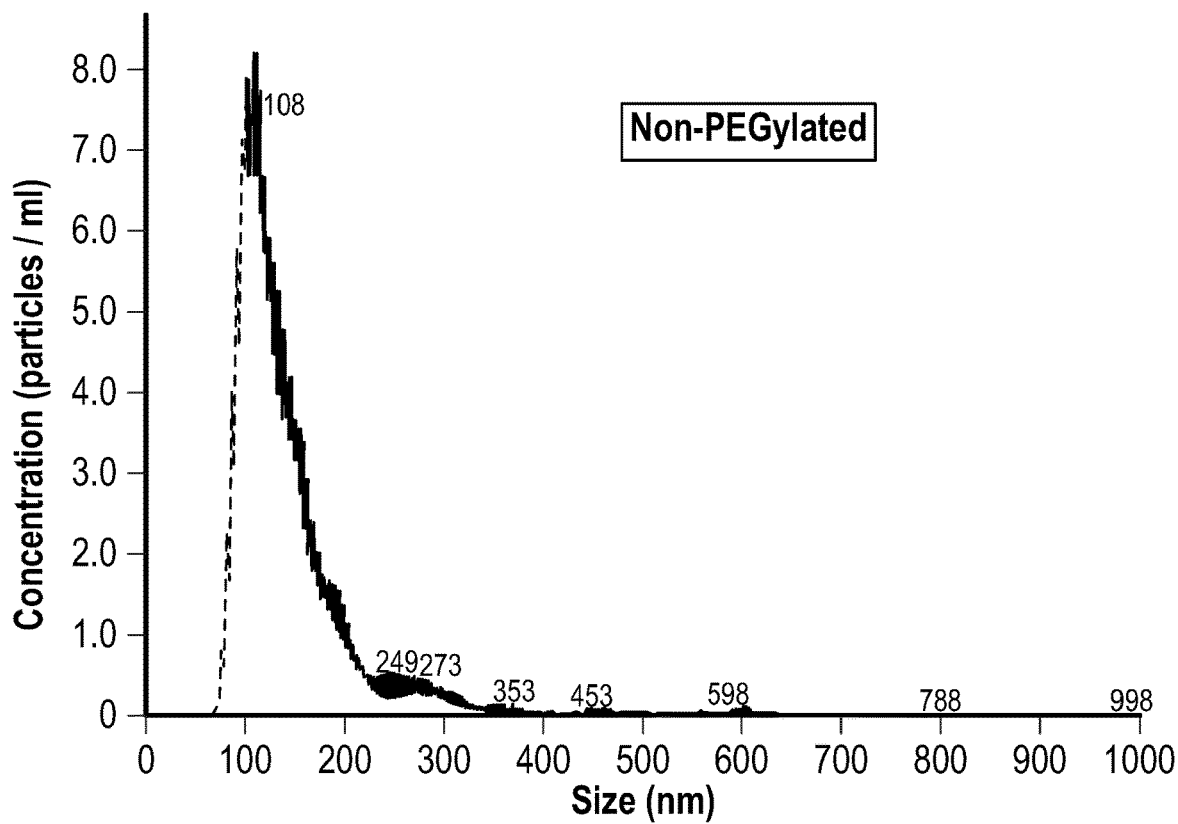
FIGS. 8a and 8b are nanoparticle tracking analysis readings for Sample 2.
Figure 8B:
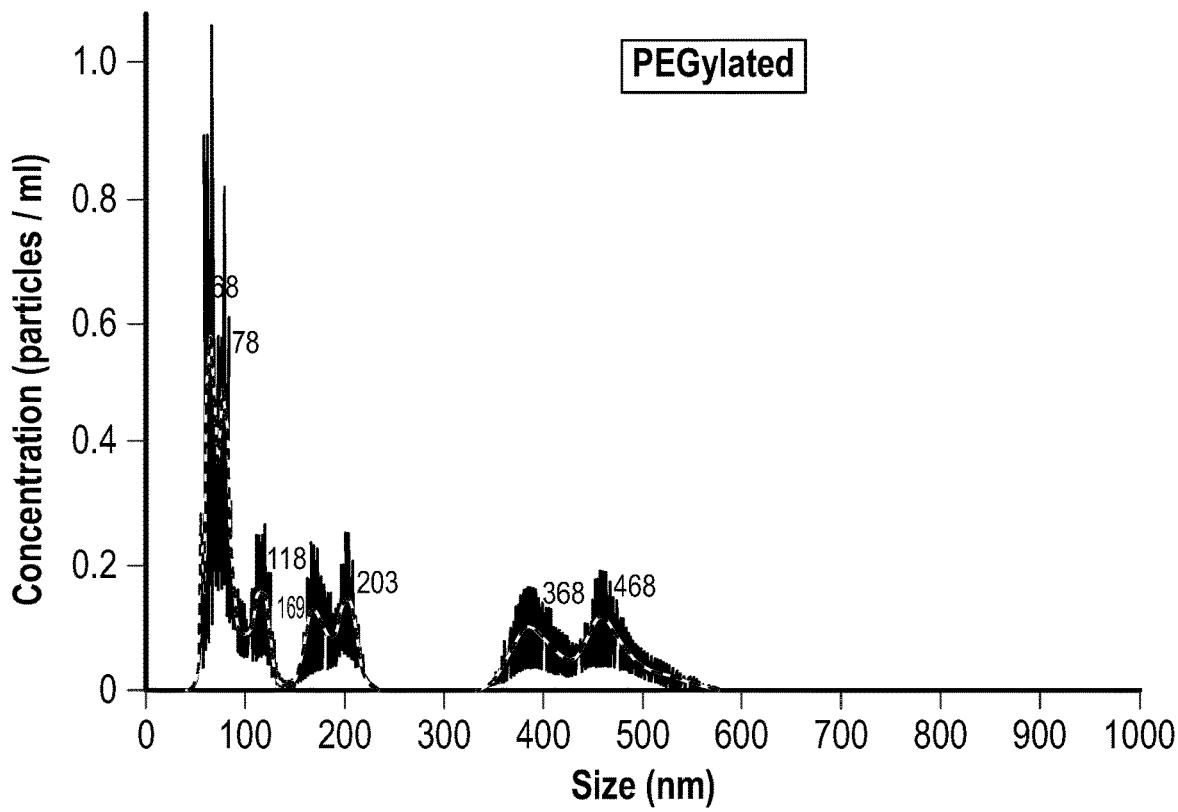

FIGS. 8a and 8b show nanoparticle tracking analysis (NTA) distribution for sample 2. EV samples for particle size (nm) at x-axis and particles concentration distributions (particles/ml) at y-axis. The non-PEGylated sample shows a definite peak at 110.5±5 nm and passed the quality test for NTA analysis although the PEGylated samples had less than 3 counts per frame and didn't pass the quality control test for NTA analysis i.e. particle free solution. The mean size distribution and particle concentration is shown in Table 5a and the total cell count and particle distribution of the source cell lysate is shown in Table 5b. Data is presented as mean, SEM, particles/cell and particles/volume of sample respectively.

TABLE 5a

| Sample 2 | Replicates | Mean Particle Size (nm) Mean | SEM | Total Particle Conc. (NPs/mL) MEAN | SEM | Particle Conc. between 30-150 nm (NPs/mL) Mean | SEM |
|---|---|---|---|---|---|---|---|
| Non-PEGylated | 6 | 110.5 | 5 | 1.06E+11 | 6.67E+08 | 7.30E+10 | 1.75E+09 |
| PEGylated | 6 | 97 | 4.5 | 1.40E+09 | 2.04E+08 | 1.08E+09 | 1.58E+08 |

TABLE 5b

| Viable Cells | Total Particle conc. (NPs/85 μls) | 30-150 nm Particles (NPs/85 μls) | Total Particles/ Cell | Total Particles (30-150 nm)/ Cell |
|---|---|---|---|---|
| 3.8E+07 | 9.0E+09 | 6.2E+09 | 235 | 162 |

Sample 3

Figure 9:
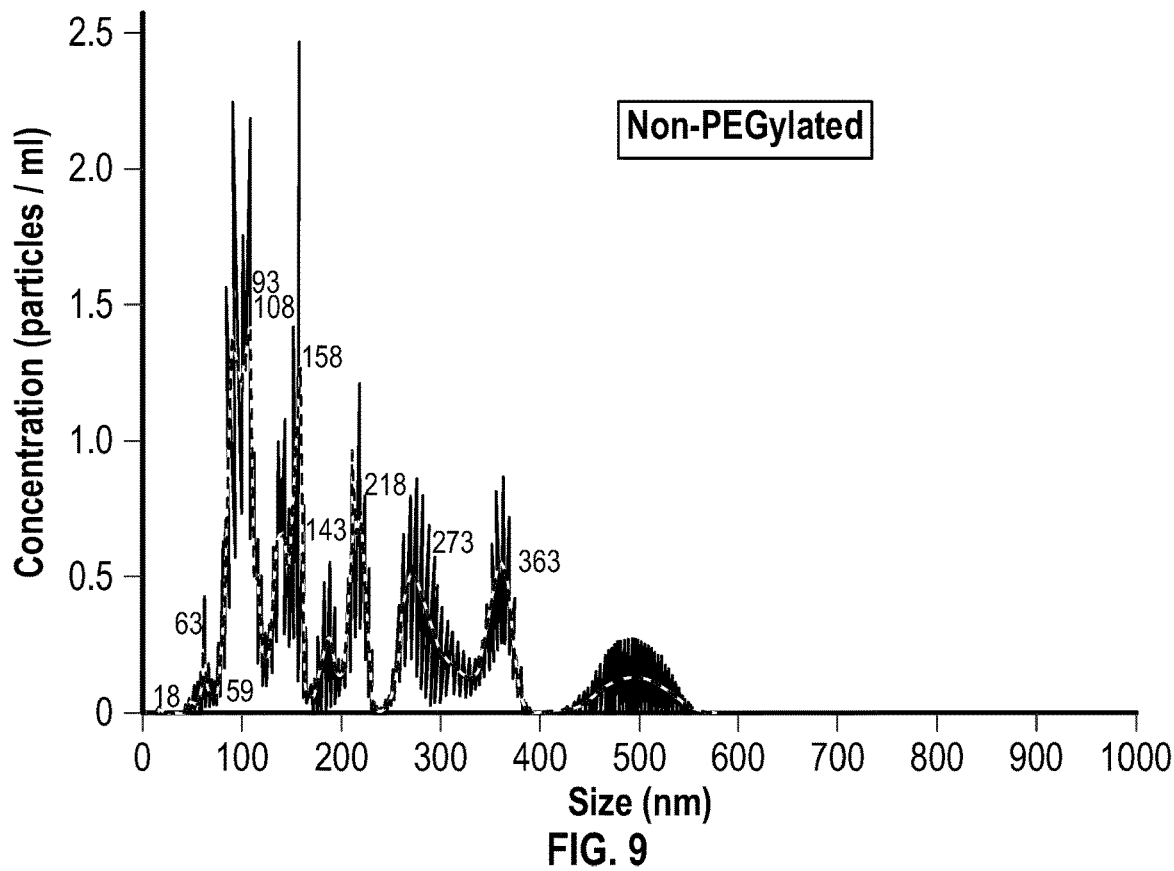
FIG. 9 is a nanoparticle tracking analysis distribution for Sample 3.

FIG. 9 shows nanoparticle tracking analysis (NTA) distribution for Sample 3 EV samples for particle size (nm) at x-axis and particle concentration distributions (particles/ml) at y-axis. The non-PEGylated sample shown has a mean size distribution at 1.56±43.5 nm and although it has passed quality test for NTA analysis but had less than 10 counts per frame for NTA analysis. The mean size distribution and particle concentrations is shown in Table 6a below, and the total cell count and particle distribution of the source cell lysate is shown in Table 6b. Data is presented as mean, SEM, particle/cell and particles/volume of sample respectively.

TABLE 6a

| Sample 3 | Replicates | Mean Particle Size (nm) Mean | SEM | Total Particle Conc. (NPs/mL) MEAN | SEM | Particle Conc. between 30-150 nm (NPs/mL) Mean | SEM |
|---|---|---|---|---|---|---|---|
| Non-PEGylated | 4 | 156 | 43.6 | 2.66E+09 | 1.83E+08 | 1.08E+09 | 4/08E+08 |

TABLE 6b

| Viable Cells | Total Particle conc. (NPs/85 μls) | 30-150 nm Particles (NPs/85 μls) | Total Particles/ Cell | Total Particles (30-150 nm)/ Cell |
|---|---|---|---|---|
| 4.1E+07 | 2.3E+08 | 9.2E+07 | 5 | 2 |

Sample 4

Figure 10:
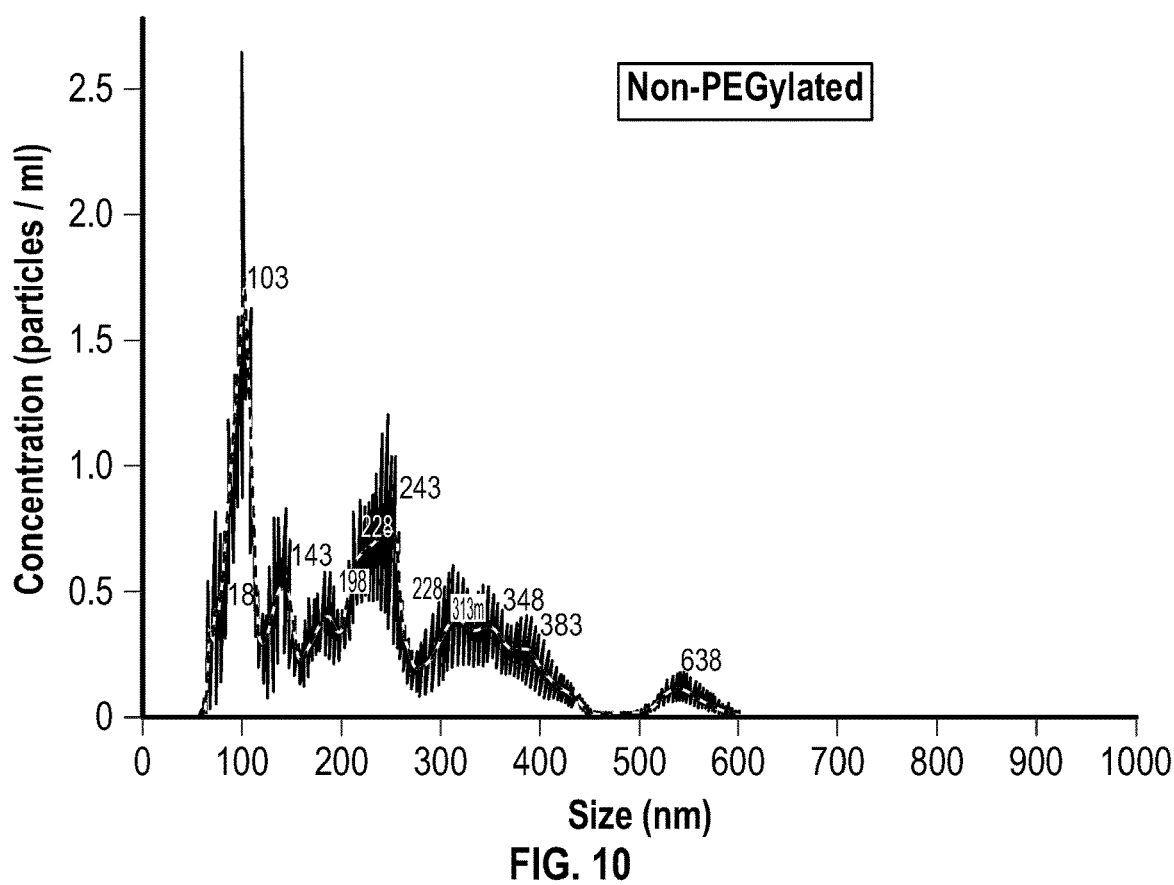
FIG. 10 is nanoparticle tracking analysis distribution for Sample 4.

FIG. 10 shows nanoparticle tracking analysis (NTA) distribution for Sample 4. EV samples for particle size (nm) at x-axis and particle concentration distributions (particles/ml) at y-axis. The non-PEGylated sample shown has a mean size distribution at 120±26 nm and although it has passed quality test for NTA analysis but had less than 10 counts per frame for NTA analysis. The mean size distribution and particle concentration is shown in Table 7a below, and the total cell count and particle distribution of the source cell lysate is shown in Table 7b. Data is presented as mean, SEM, particle/cell and particles/volume of sample respectively.

TABLE 7a

| Sample 4 | Replicates | Mean Particle Size (nm) Mean | SEM | Total Particle Conc. (NPs/mL) MEAN | SEM | Particle Conc. between 30-150 nm (NPs/mL) Mean | SEM |
|---|---|---|---|---|---|---|---|
| Non-PEGylated | 6 | 120 | 26 | 3.25E+09 | 1.88E+08 | 1.11E+09 | 1.43E+08 |

TABLE 7b

| Viable Cells | Total Particle conc. (NPs/85 μls) | 30-150 nm Particles (NPs/85 μls) | Total Particles/ Cell | Total Particles (30-150 nm)/ Cell |
|---|---|---|---|---|
| 4.5E+07 | 2.8E+08 | 9.4E+07 | 6 | 2 |

Sample 5

Figure 11:
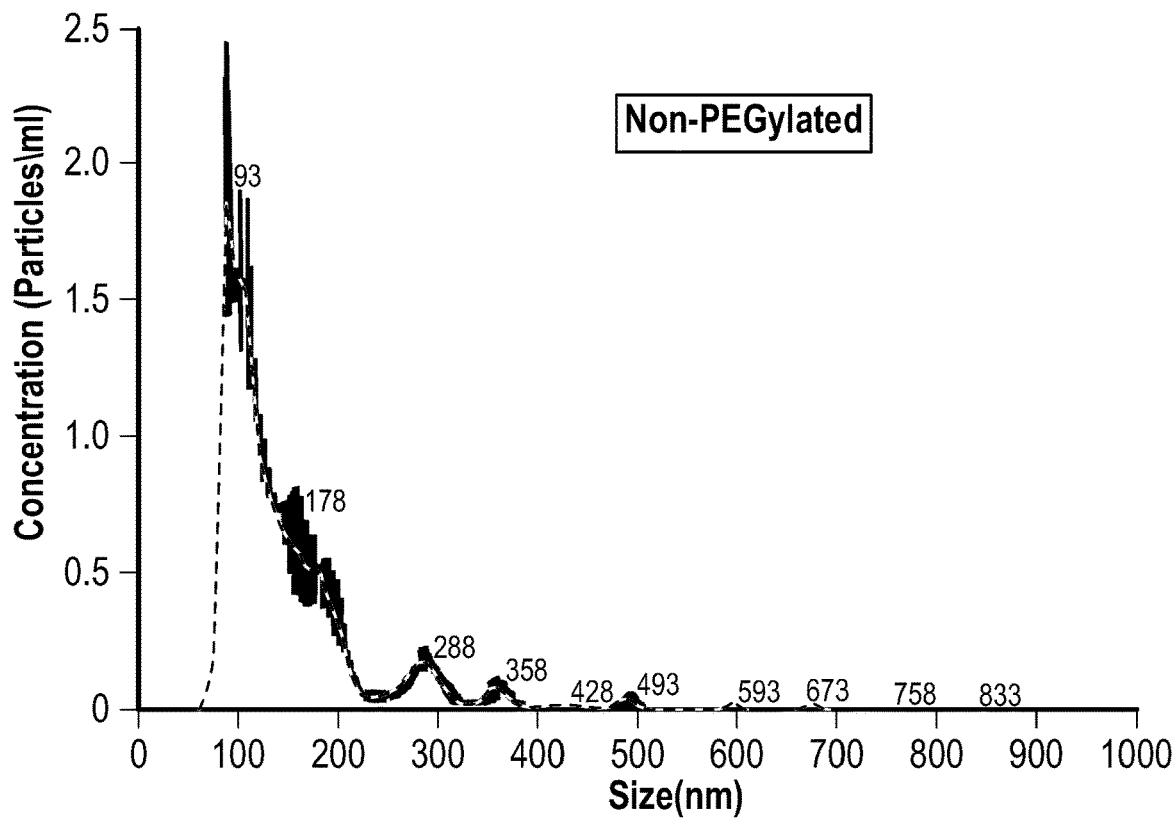
FIG. 11 is nanoparticle tracking analysis distribution for Sample 5.

FIG. 11 shows nanoparticle tracking analysis (NTA) distribution for Sample 5. EV samples for particle size (nm) at x-axis and particle concentration distributions (particles/ml) at y-axis. The non-PEGylated sample shown has a mean size distribution at 96±3.5 nm and although it has passed quality test for NTA analysis but had less than 10 counts per frame for NTA analysis. The mean size distribution and particle concentration is shown in Table 8a below, and the total cell count and particle distribution of the source cell lysate is shown in Table 8b. Data is presented as mean, SEM, particle/cell and particles/volume of sample respectively.

TABLE 8a

| Sample 5 | Replicates | Mean Particle Size (nm) | | Total Particle Conc. (NPs/mL) | | Particle Conc. between 30-150 nm (NPs/mL) | |
|---|---|---|---|---|---|---|---|
| | | Mean | SEM | MEAN | SEM | Mean | SEM |
| Non-PEGylated | 6 | 96 | 3.5 | 2.72E+10 | 1.96E+09 | 1.76E+10 | 9.96E+08 |

TABLE 8b

| Viable Cells | Total Particle conc. (NPs/85 μls) | 30-150 nm Particles (NPs/85 μls) | Total Particles/ Cell | Total Particles (30-150 nm)/ Cell |
|---|---|---|---|---|
| 4.4E+07 | 2.3E+09 | 1.5E+09 | 53 | 34 |

Sample 6

Figure 12A:
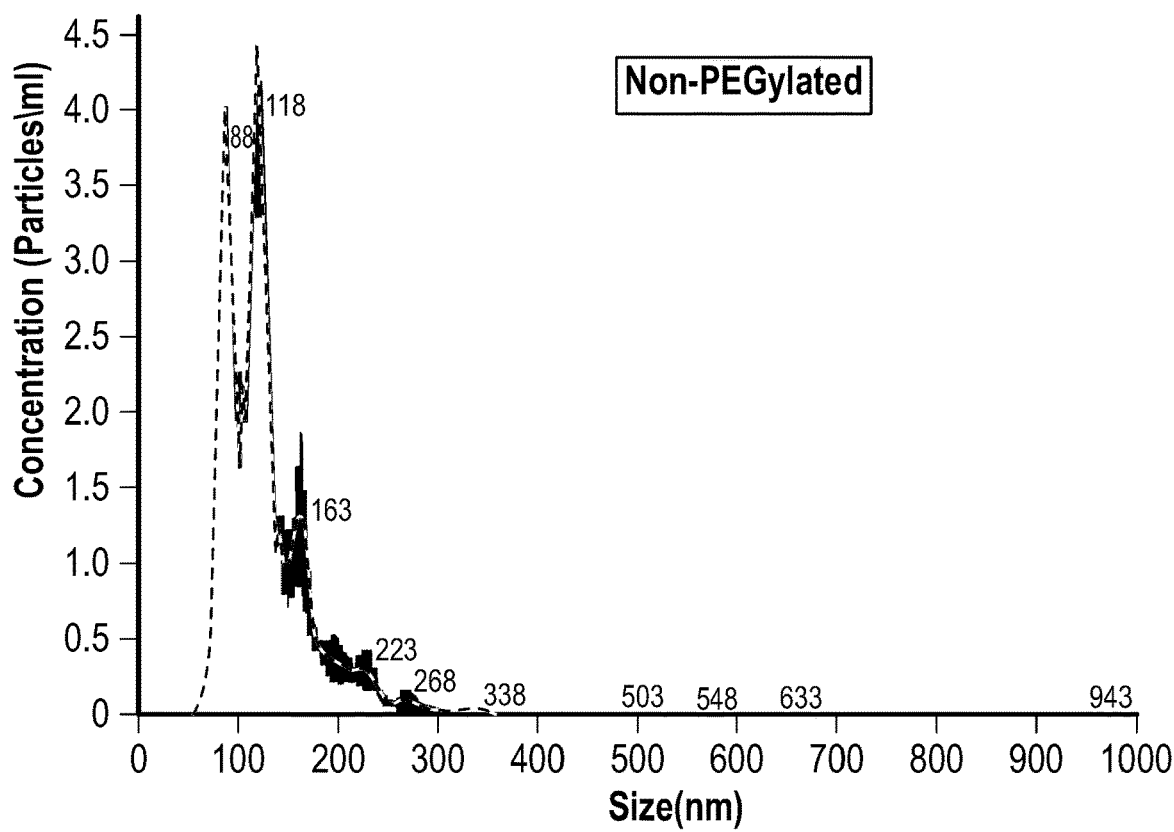
FIGS. 12a and 12b are nanoparticle tracking analysis distributions for Sample 6.
Figure 12B:
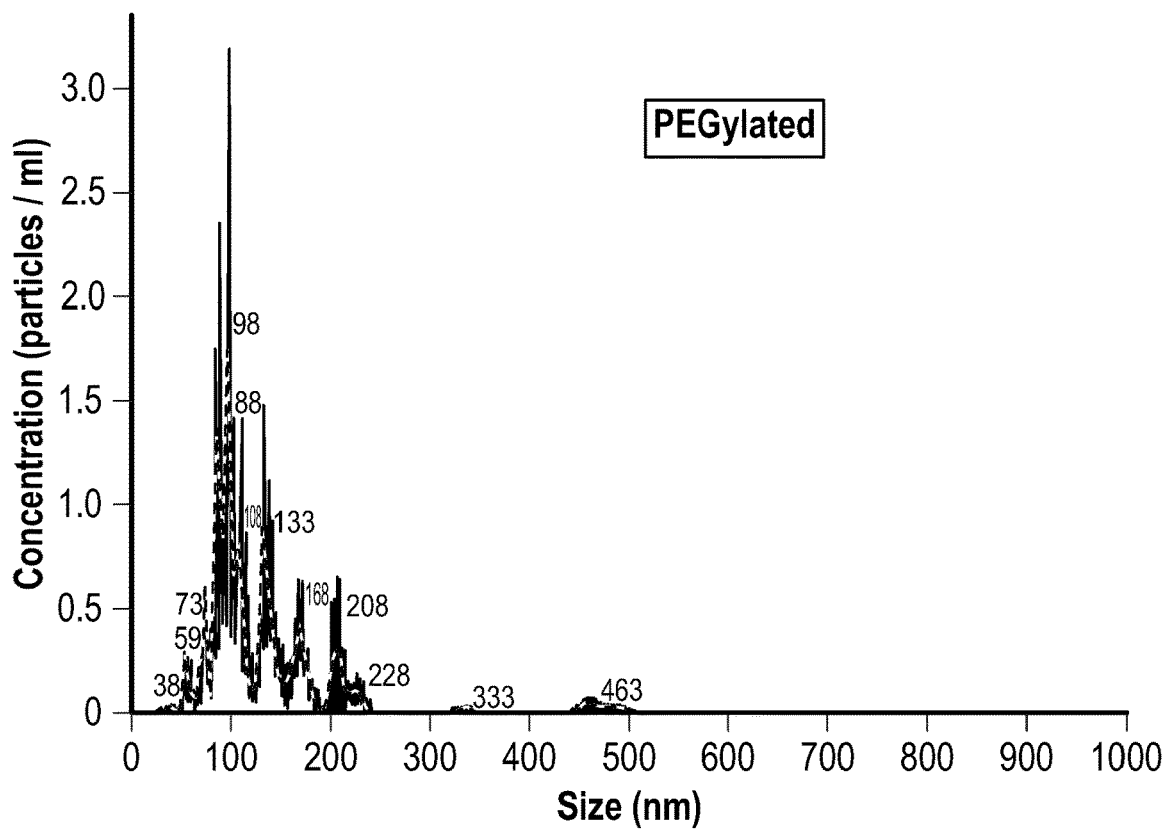

FIGS. 12a and 12b show nanoparticle tracking analysis (NTA) distribution for Sample 5. EV samples for particle size (nm) at x-axis and particle concentration distributions (particles/ml) at y-axis. The non-PEGylated sample shown has a definite peak at 112±nm and passed the quality test for NTA analysis although the PEGylated sample had less than 3 counts per frame and didn't pass the quality control test for NTA analysis i.e. particle free solution. The mean size distribution and particle concentration is shown in Table 9a below, and the total cell count and particle distribution of the source cell lysate is shown in Table 9b. Data is presented as mean, SEM, particle/cell and particles/volume of sample respectively.

TABLE 9a

| Sample 6 | Replicates | Mean Particle Size (nm) | | Total Particle Conc. (NPs/mL) | | Particle Conc. between 30-150 nm (NPs/mL) | |
|---|---|---|---|---|---|---|---|
| | | Mean | SEM | MEAN | SEM | Mean | SEM |
| Non-PEGylated | 6 | 112 | 5 | 4.78E+10 | 2.57E+09 | 3.65E+10 | 2.10E+09 |
| PEGylated | 6 | 117 | 23.50 | 7.52E+08 | 1.01E+08 | 3.60E+08 | 1.15E+08 |

TABLE 9b

| Viable Cells | Total Particle conc. (NPs/85 μls) | 30-150 nm Particles (NPs/85 μls) | Total Particles/ Cell | Total Particles (30-150 nm)/ Cell |
|---|---|---|---|---|
| 4.1E+07 | 4.1E+09 | 3.1E+09 | 99 | 76 |

Sample 7

Figure 13:
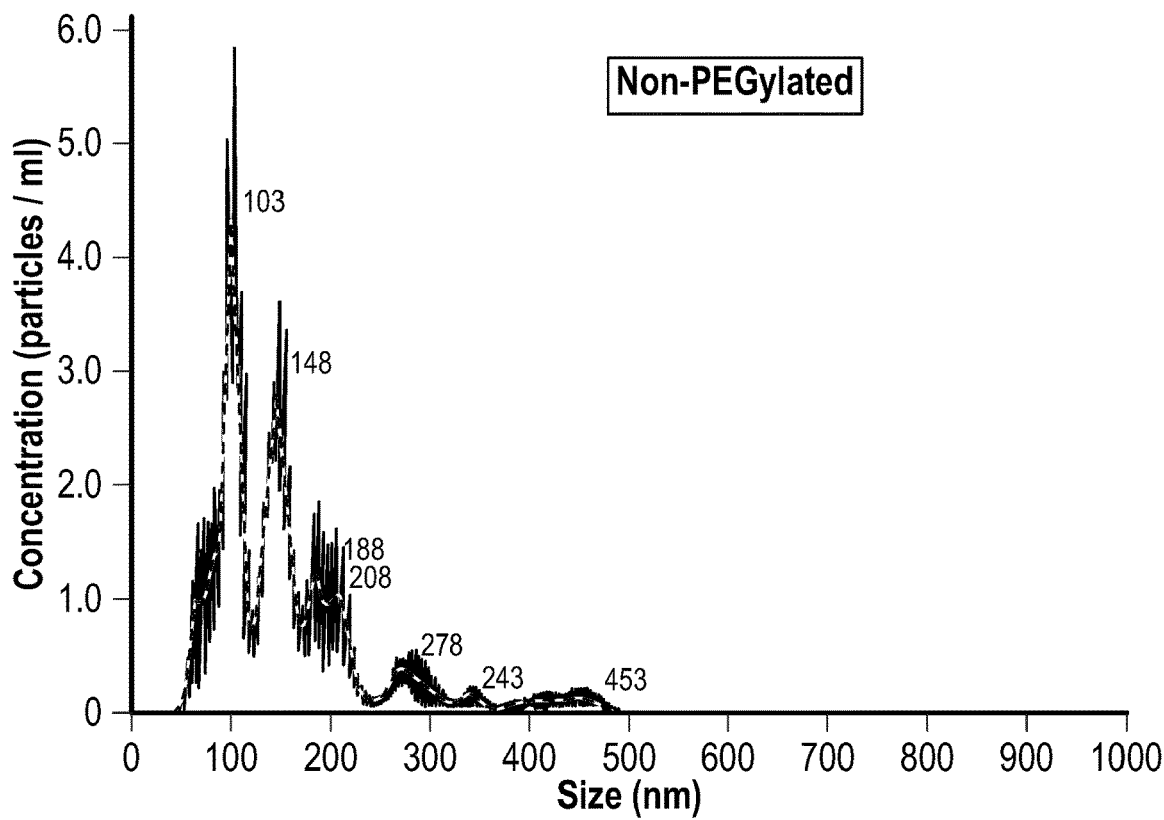
FIG. 13 is nanoparticle tracking analysis distribution for Sample 7.

FIG. 13 shows nanoparticle tracking analysis (NTA) distribution for Sample 7. EV samples for particle size (nm) at x-axis and particle concentration distributions (particles/ml) at y-axis. The non-PEGylated sample shown has a mean size distribution at 93.5±6 nm and has passed quality test for NTA analysis meeting the criteria for purified EV sample but has less than 10 counts per frame for SEM. The mean size distribution and particle concentration is shown in Table 10a below, and the total cell count and particle distribution of the source cell lysate is shown in Table 10b. Data is presented as mean, SEM, particle/cell and particles/volume of sample respectively.

TABLE 10a

| Sample 7 | Replicates | Mean Particle Size (nm) | | Total Particle Conc. (NPs/mL) | | Particle Conc. between 30-150 nm (NPs/mL) | |
|---|---|---|---|---|---|---|---|
| | | Mean | SEM | MEAN | SEM | Mean | SEM |
| Non-PEGylated | 6 | 96 | 3.5 | 2.72E+10 | 1.96E+09 | 1.76E+10 | 9.96E+08 |

TABLE 10b

| Viable Cells | Total Particle conc. (NPs/85 μls) | 30-150 nm Particles (NPs/85 μls) | Total Particles/ Cell | Total Particles (30-150 nm)/ Cell |
|---|---|---|---|---|
| 4.4E+07 | 2.3E+09 | 1.5E+09 | 53 | 34 |

Zeta Analysis

Figure 14A:
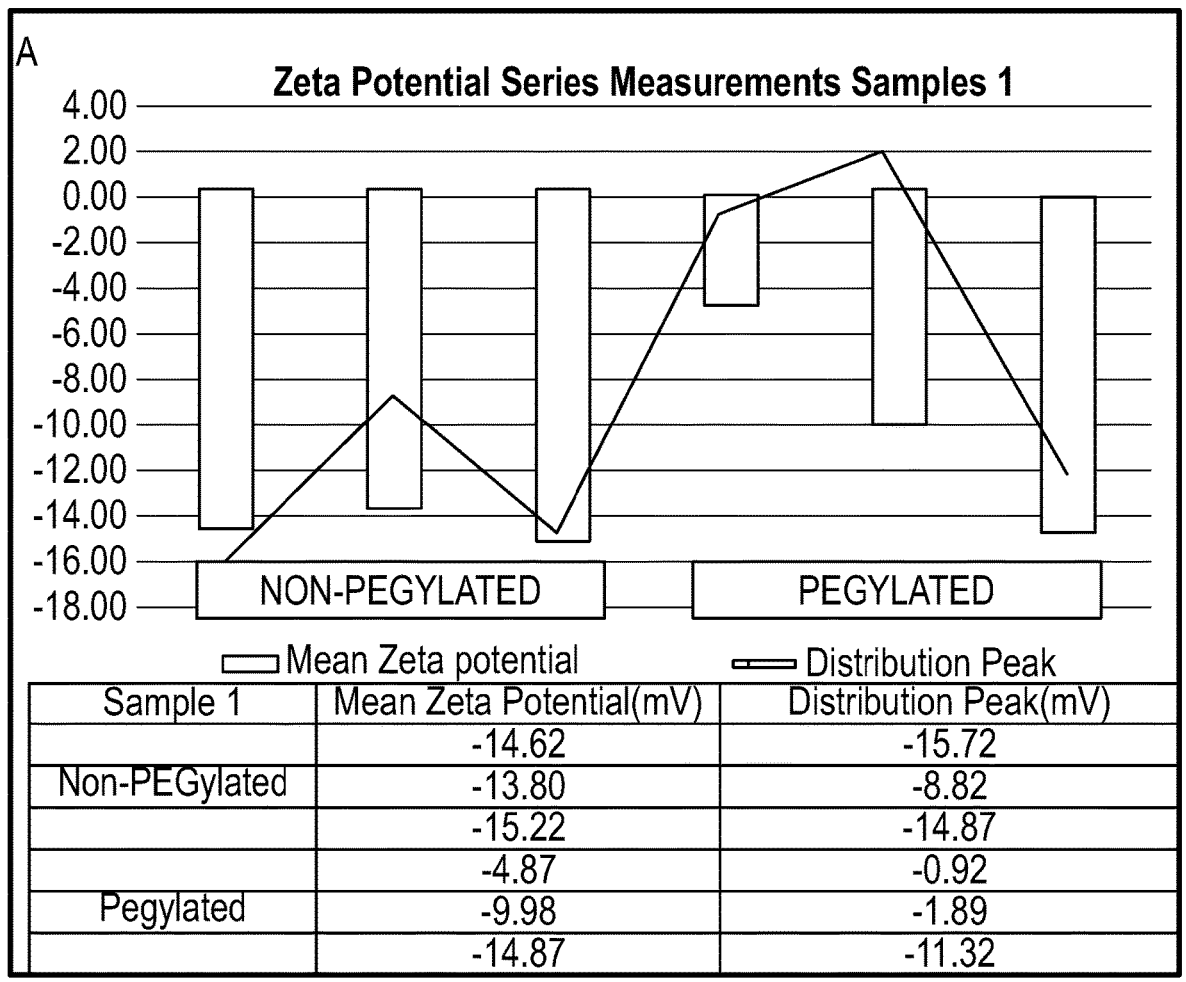
FIG. 14a is a plot showing zeta potential readings for PEGylated and non-PEGylated Sample 1.
Figure 14B:
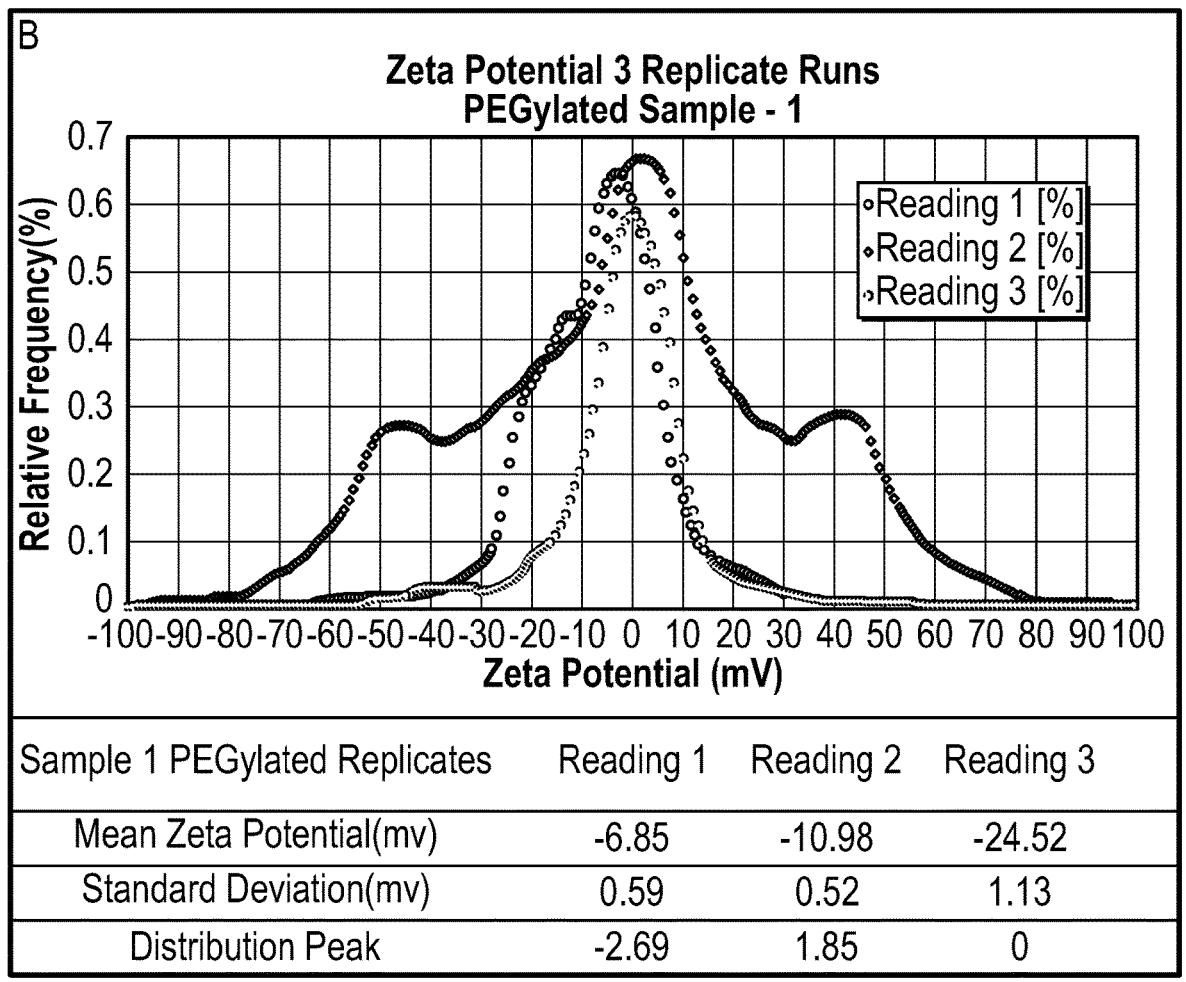
FIG. 14b is a plot of zeta potential intensity distributions for tree separate measurement for PEGylated Sample 1.

Sample 1 (PEG 100%) FIGS. 14a and 14b show mean zeta potential values for PEGylated and non-PEGylated EV isolate sample 1 (PEG 100%). FIG. 14a is a plot showing series measurement readings for PEGylated EV isolate sample with mean zeta potential and distribution peak (mode) value for each run (particle concentration; 1:100 in PBS). FIG. 14b show the zeta potential intensity distributions for three separate measurement reading for PEGylated EV isolate sample 1 (particle concentration: 1:100 in PBS) with relative frequency (%) on the y=axis and zeta potential (mV) on the x-axis. The different curves represent three consecutive measurements of the separate sample dilutions from same EV isolate. The zeta potentials were determined using the Smoluschowski approximation. The data is represented as Mean and SD. All data is in mV.

Sample 2 (PEG 50%)

Figure 15A:
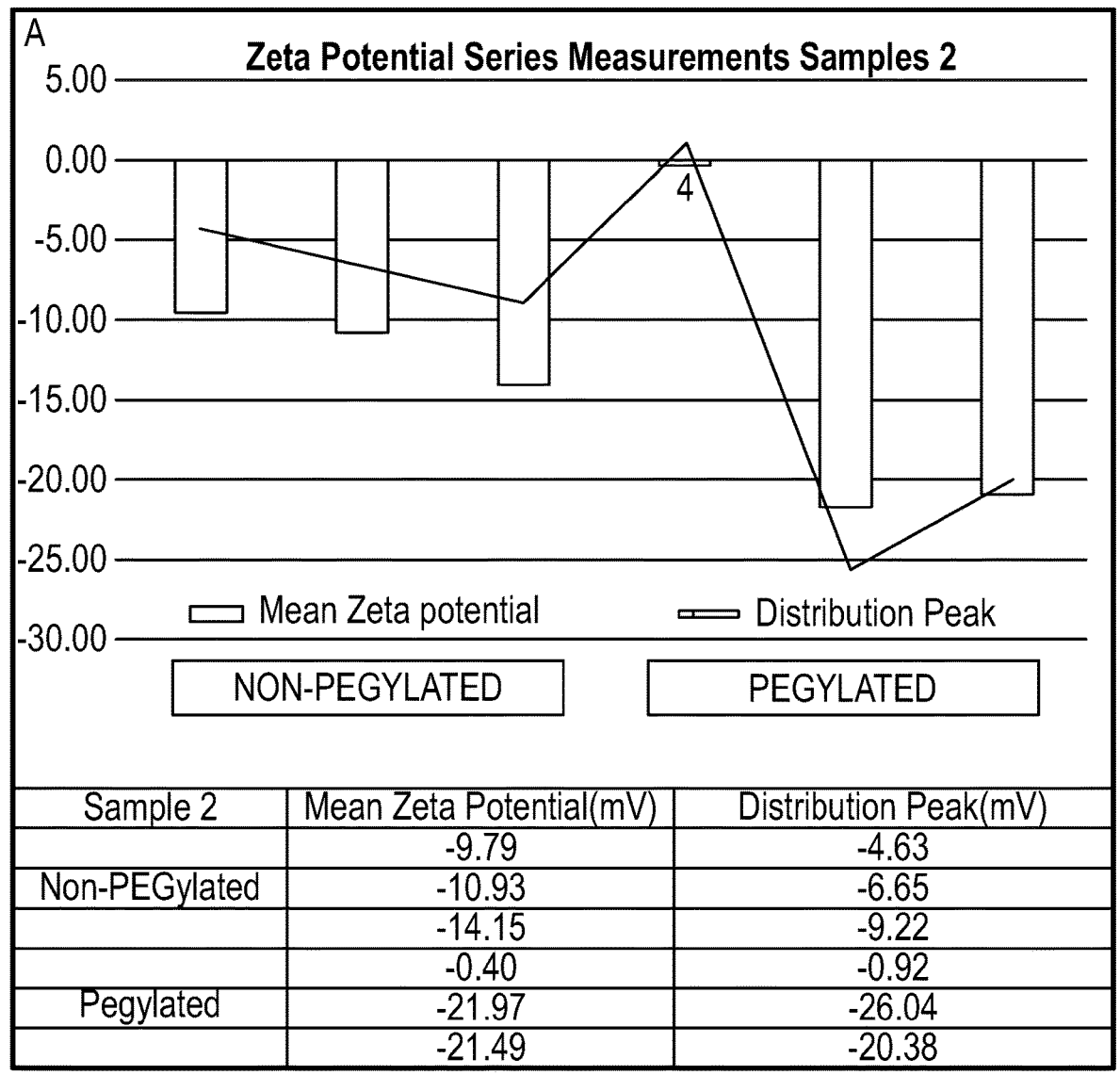
FIG. 15a is a plot showing zeta potential readings for PEGylated and non-PEGylated Sample 2.
Figure 15B:
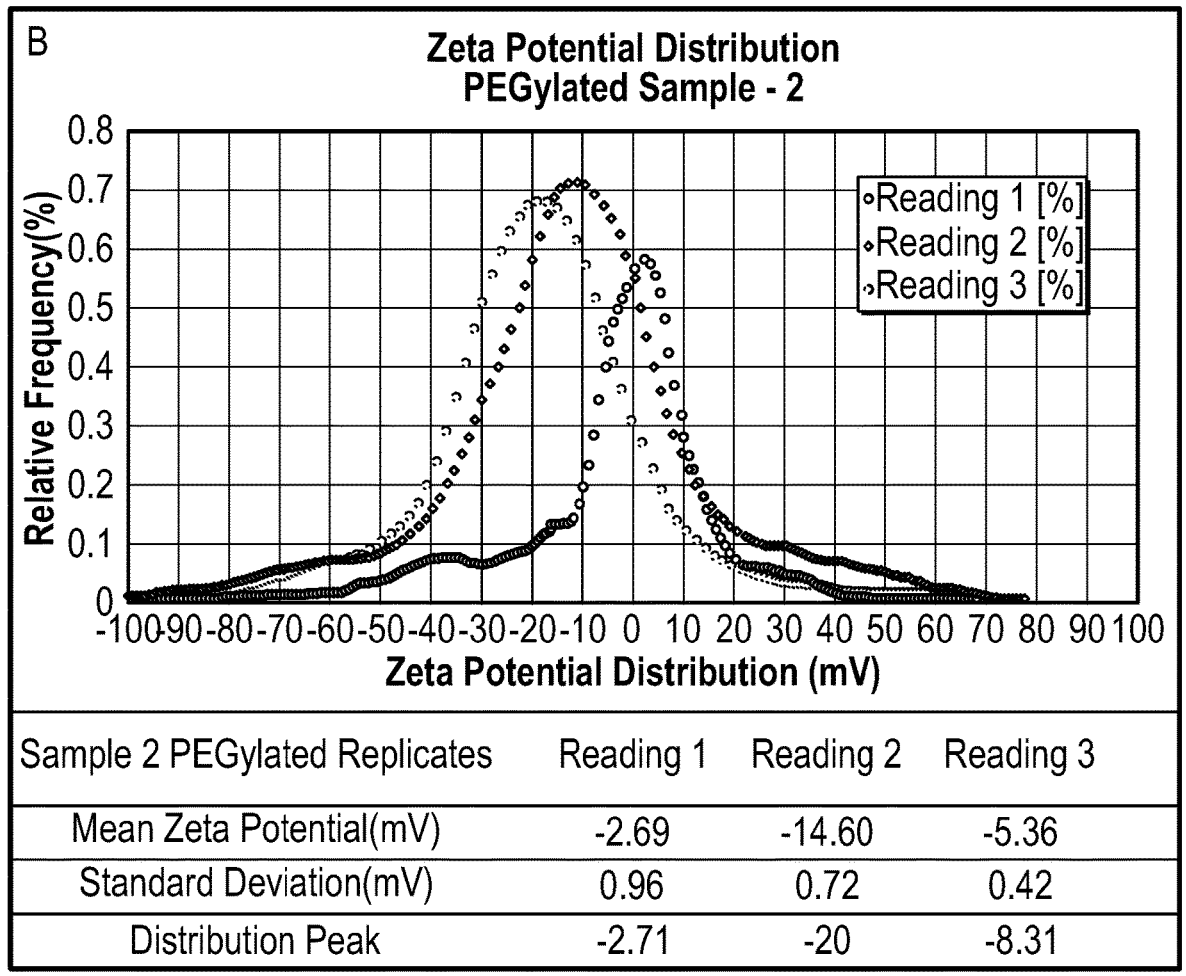
FIG. 15b is a plot of zeta potential intensity distributions for tree separate measurement for PEGylated Sample 2.

FIGS. 15a and 15b are equivalent to FIGS. 14a and 14b with respect of sample 2.

Sample 4 (PEG 50%)

Figure 16:
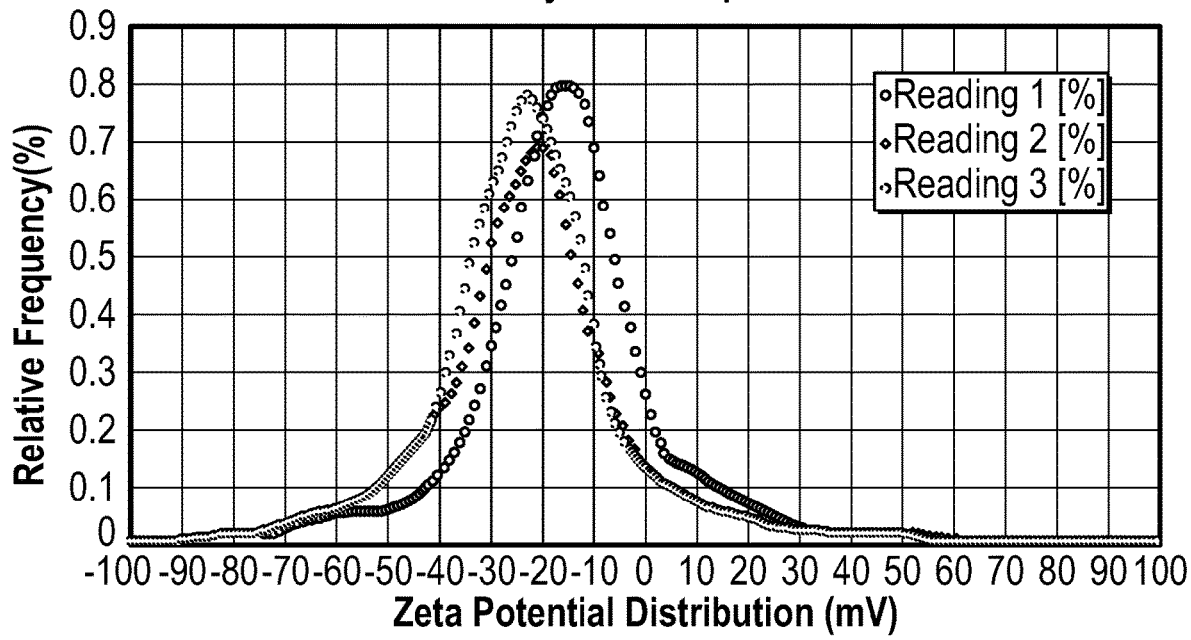
FIG. 16 is a plot showing mean zeta potential values for PEGylated and non-PEGylated Sample 4.

FIG. 16 show the mean zeta potential values for PEGylated and nonPEGylated EV isolate sample 4 (PEG 50%). Zeta potential intensity distributions for three separate measurement reading for PEGylate EV isolated sample 4 (particle concentration: 1:16 in PBS) with relative frequency (%) on the y-axis and zeta potential (mV) on the x-axis. The different curves represent three consecutive measurements of the same PEGylated EV isolate. Tables 11 a and 11b below shows single run measurement readings for non-PEGylated EV isolate sample with mean zeta potential, followed by specific values same sample after PEGylation. SD and distribution peak (mode) values for each run (particle concentration 1:100 in PBS). The zeta potentials were determined using the Smoluschowski approximation. The data is represented as Mean and SD. All data is in mV.

TABLE 11a

| Pre-PEG Mean Zeta Potential Readings in a 3 series replicate 1000 readings run (mV) | | | Average of pre-PEG readings | Mode NTA Before PEG (nM) |
|---|---|---|---|---|
| −12.93 | N/A | N/A | −12.93 | 120 |

TABLE 11b

| | Sample 4 PEGylated | | |
|---|---|---|---|
| | Reading 1 | Reading 2 | Reading 3 |
| Mean Zeta Potential (mV) | −18.00 | −22.95 | −19.13 |
| Standard Deviation (mV) | 0.80 | 0.96 | 0.93 |
| Distribution Peak | −15.11 | −22.16 | −23.25 |

Sample 5 (PEG 100%)

Figure 17:
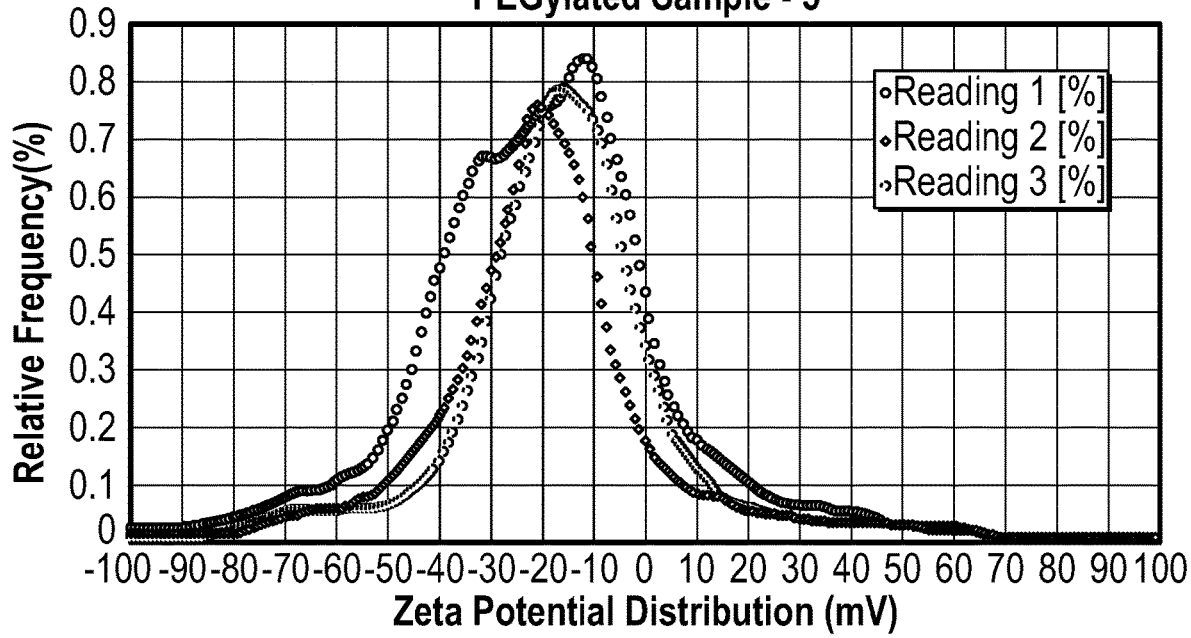
FIG. 17 is a plot showing mean zeta potential values for PEGylated and non-PEGylated Sample 5.

FIG. 17 show the mean zeta potential values for PEGylated and non-PEGylated EV isolate sample 5 (PEG 100%). Zeta potential intensity distributions for three separate measurement reading for PEGylate EV isolated sample 4 (particle concentration: 1:16 in PBS) with relative frequency (%) on the y-axis and zeta potential (mV) on the x-axis. The different curves represent three consecutive measurements of the same PEGylated EV isolate. Tables 12a and 12b below shows single run measurement readings for non-PEGylated EV isolate sample with mean zeta potential, followed by specific values same sample after PEGylation. SD and distribution peak (mode) values for each run (particle concentration 1:100 in PBS). The zeta potentials were determined using the Smoluschowski approximation. The data is represented as Mean and SD. All data is in mV.

TABLE 12a

| Pre-PEG Mean Zeta Potential Readings in a 3 series replicate 1000 readings run (mV) | | | Average of pre-PEG readings | Mode NTA Before PEG (nM) |
|---|---|---|---|---|
| −7.74 | −10.63 | −13.08 | −10.48 | 96 |

TABLE 12b

| | Sample 4 PEGylated | | |
|---|---|---|---|
| | Reading 1 | Reading 2 | Reading 3 |
| Mean Zeta Potential (mV) | −18.77 | −17/38 | −17.41 |
| Standard Deviation (mV) | 0.86 | 0.83 | 0.85 |
| Distribution Peak | −11.96 | −20.41 | −16.72 |

Sample 6 (PEG 75%)

Figure 18A:
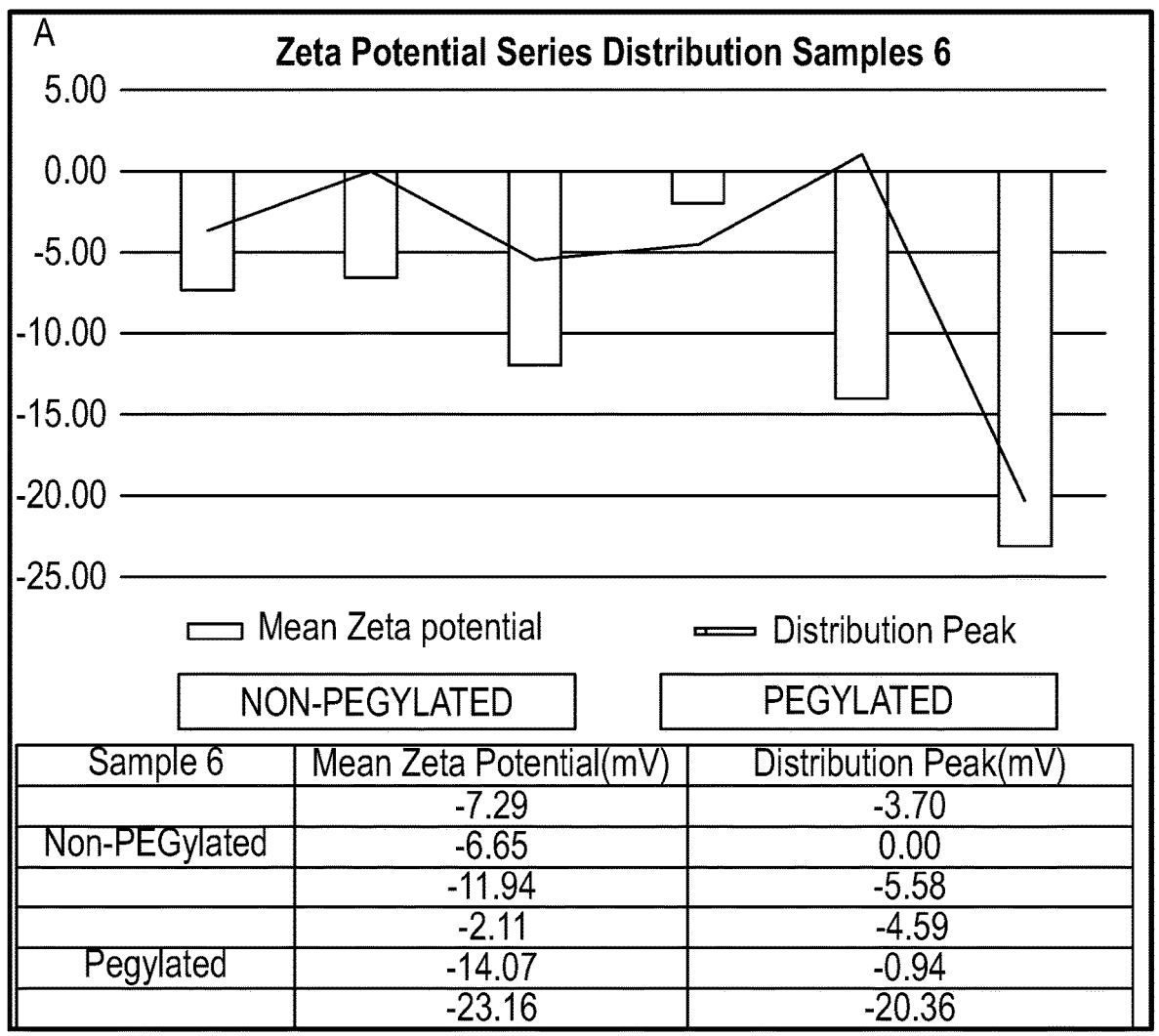
FIG. 18a is a plot showing zeta potential readings for PEGylated and non-PEGylated Sample 6.
Figure 18B:
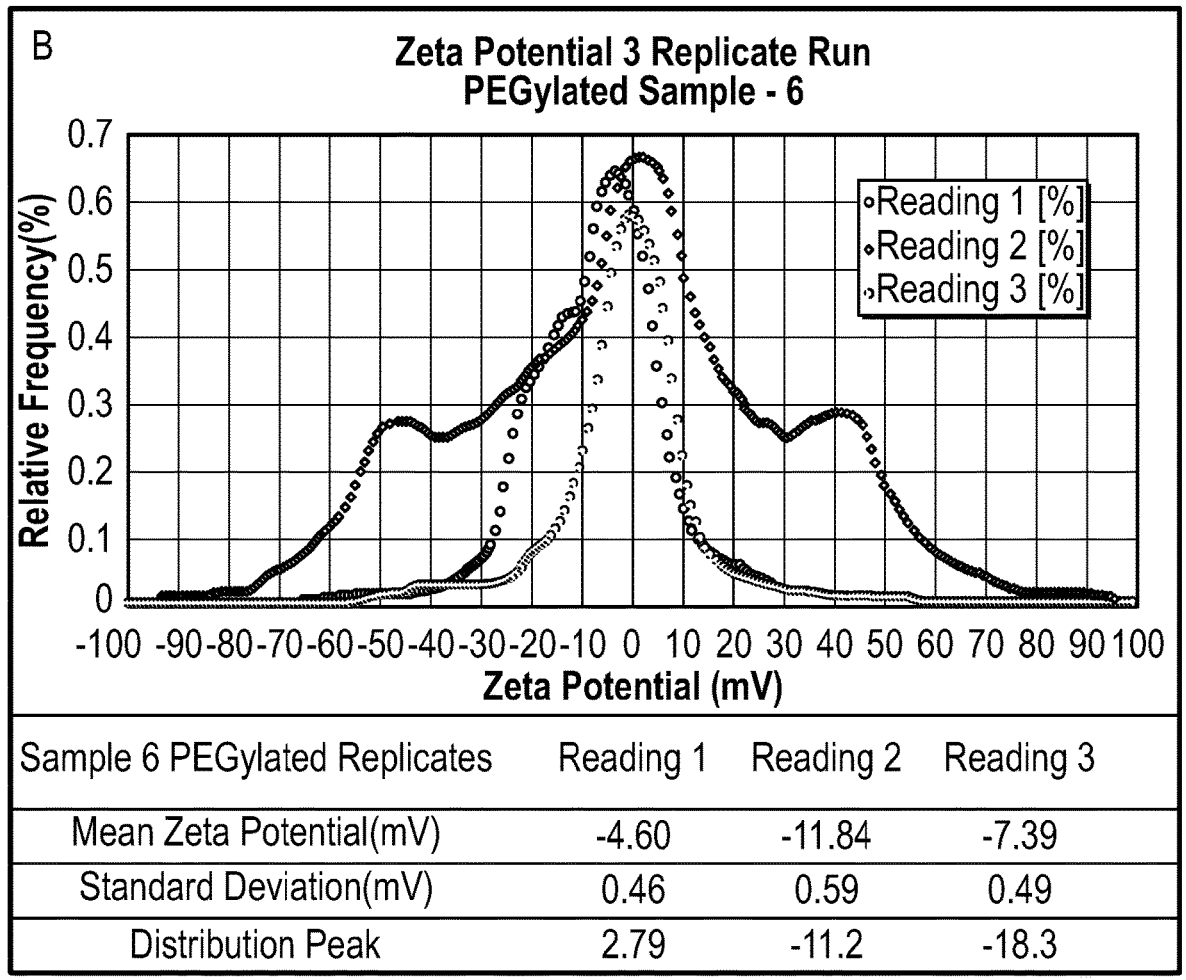
FIG. 18b is a plot of zeta potential intensity distributions for tree separate measurement for PEGylated Sample 6.

FIGS. 18a and 18b show mean zeta potential values for PEGylated and non-PEGylated EV isolate sample 6 (PEG 100%). FIG. 18a is a plot showing series measurement readings for PEGylated EV isolate sample with mean zeta potential and distribution peak (mode) value for each run (particle concentration; 1:100 in PBS). FIG. 18b show the zeta potential intensity distributions for three separate measurement reading for PEGylated EV isolate sample 6 (particle concentration: 1:100 in PBS) with relative frequency (%) on the y=axis and zeta potential (mV) on the x-axis. The different curves represent three consecutive measurements of the separate sample dilutions from same EV isolate. The zeta potentials were determined using the Smoluschowski approximation. The data is represented as Mean and SD. All data is in mV.

Sample 7 (PEG 150%)

Figure 19:
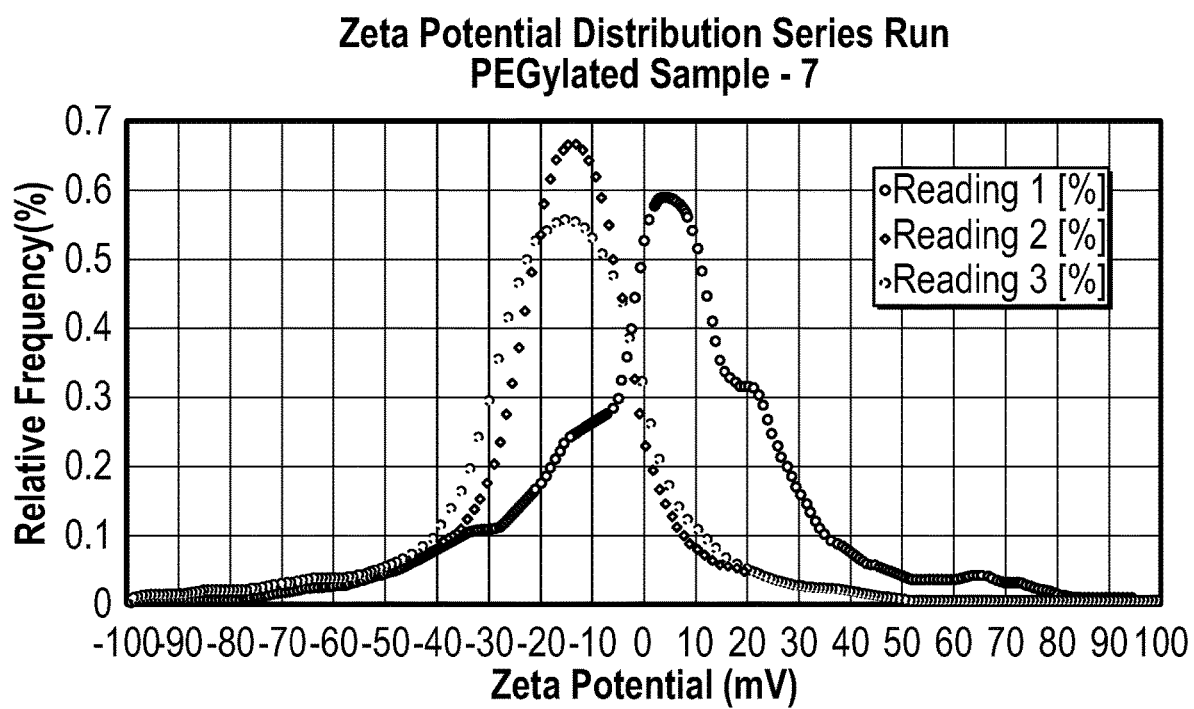
FIG. 19 is a plot showing mean zeta potential values for PEGylated and non-PEGylated Sample 7.

FIG. 19 show the mean zeta potential values for PEGylated and non-PEGylated EV isolate sample 7 (PEG 100%). Zeta potential intensity distributions for three separate measurement reading for PEGylate EV isolated sample 7 (particle concentration: 1:16 in PBS) with relative frequency (%) on the y-axis and zeta potential (mV) on the x-axis. The different curves represent three consecutive measurements of the same PEGylated EV isolate. Tables 13a and 13b below shows single run measurement readings for non-PEGylated EV isolate sample with mean zeta potential, followed by specific values same sample after PEGylation. SD and distribution peak (mode) values for each run (particle concentration 1:100 in PBS). The zeta potentials were determined using the Smoluschowski approximation. The data is represented as Mean and SD. All data is in mV.

TABLE 13a

| Pre-PEG Mean Zeta Potential Readings in a 3 series replicate 1000 readings run (mV) | | | Average of pre-PEG readings | Mode NTA Before PEG (nM) |
|---|---|---|---|---|
| −15.49 | −18.70 | −13.35 | −15.85 | 93.50 |

TABLE 13b

| | Sample 4 PEGylated | | |
|---|---|---|---|
| | Reading 1 | Reading 2 | Reading 3 |
| Mean Zeta Potential (mV) | −9.21 | −15.71 | −16.82 |
| Standard Deviation (mV) | 0.90 | 0.71 | 0.56 |
| Distribution Peak | 4.59 | −13.63 | −14.73 |

Transduction of MSCs

Transduction of hMSCs Donor #096 was completed using established protocols. Lentivirus particles were sourced from Genecopoeia Ltd.

We currently have 4 batches of Transduced hMSCs Cells listed below, some of the initial attempts with MOI of 1 to 2 to transduce the hMSCs were unsuccessful and are not included.

Lentivirus Titre Volumes

TABLE 14

| Lentivirus | TU/ml | TU/µl |
|---|---|---|
| LPP-CS-NEG | 1.63E+08 | 1.63E+05 |
| LPP-CS-CFTR | 1.82E+08 | 1.82E+05 |

* 1 TU = 100 copies of viral genomic RNA, which combined are able to infect 1 cell.

Transduction Volumes for hMSCs Transduction

TABLE 15

| LPP-CS-NEG Volume used (µls) | LPP-CS-CFTR Volume used (µls) | Transduction Dates | Current Stocks | |
|---|---|---|---|---|
| | | | EGFP-NEG | EGFP-CFTR |
| 18.00 | 18.00 | 22-May | 1 × T175 T-Flask | 1 × T75 T-Flask |
| 12.50 | 12.50 | 30-May | 2 × T75 T-Flask | 1 × T25 T-Flask |
| 18.00 | 18.00 | 07-Jun | 2 × T175 T-Flask | 2 × T175 T-Flask |
| 18.00 | 18.00 | 14-Jun | 1 × T75 + 1 × T25 T-Flask | 1 × T75 T Flask + 1 × T25 T-Flask |

Figure 20:
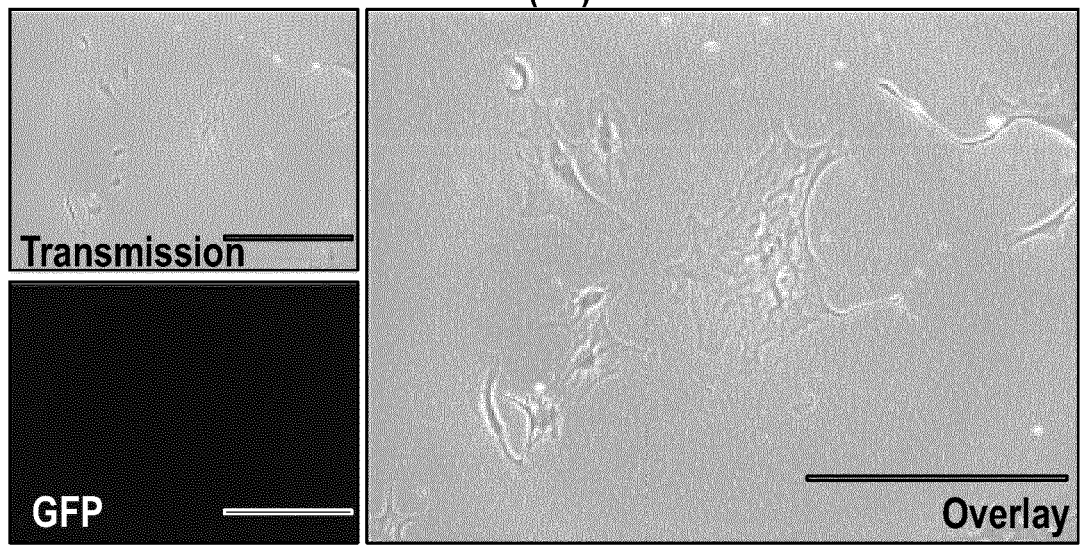
FIG. 20 shows GFP Fluorescence for hMSC cells with EGFP-CFTR Transduction.
Figure 21:
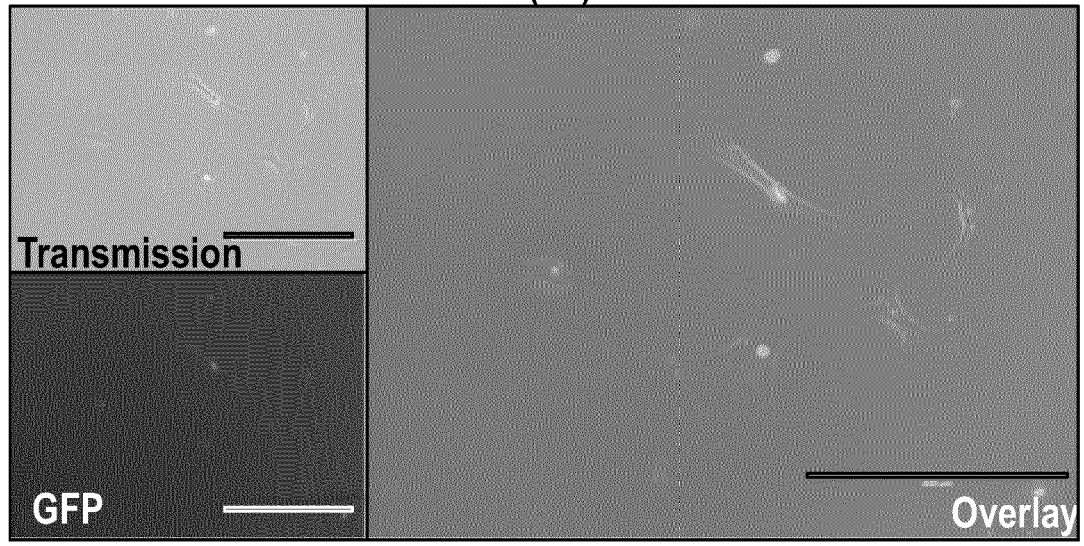
FIG. 21 shows GFP fluorescence for hMSC cells with EGFP-Negative Control Transduction.
Figure 22:
FIG. 22 shows the CFTR-EGFP positive MSCs taken on a fluorescence microscope following seeding the cells on slides, fixing and staining the nuclei with DAPI (blue) at ×10 magnification.
Figure 23:
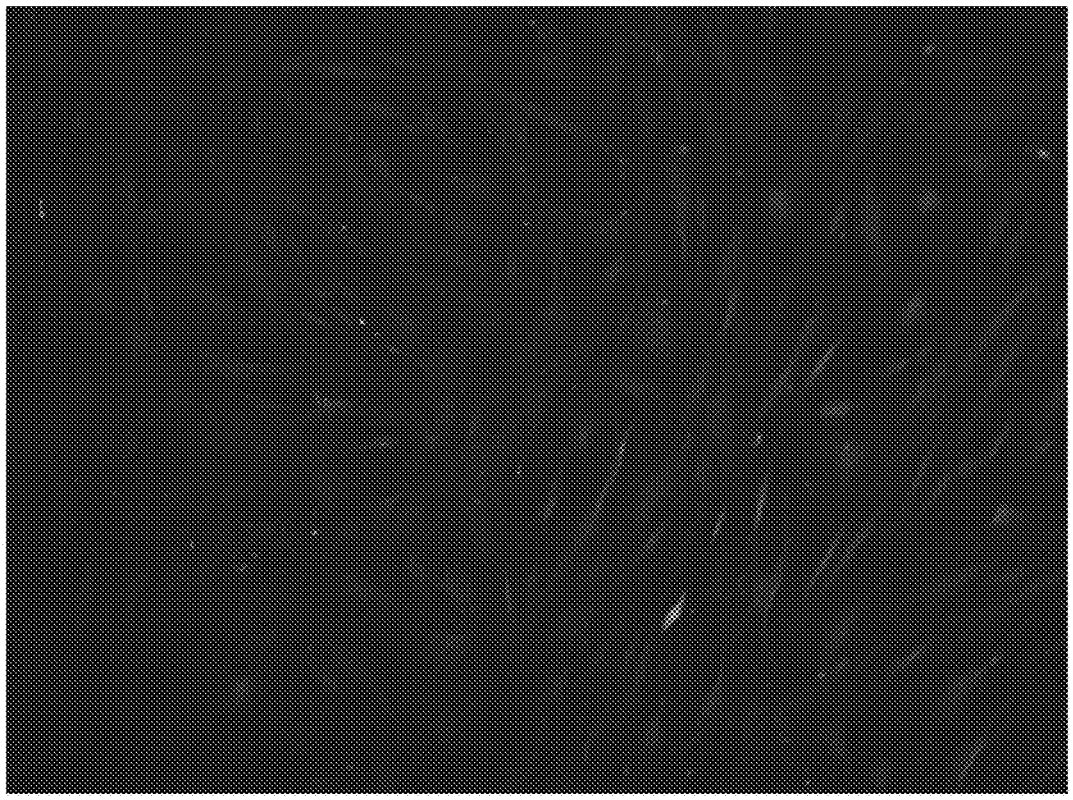
FIG. 23 shows the CFTR-EGFP positive MSCs taken on a fluorescence microscope following seeding the cells on slides at ×10 magnification.
Figure 24:
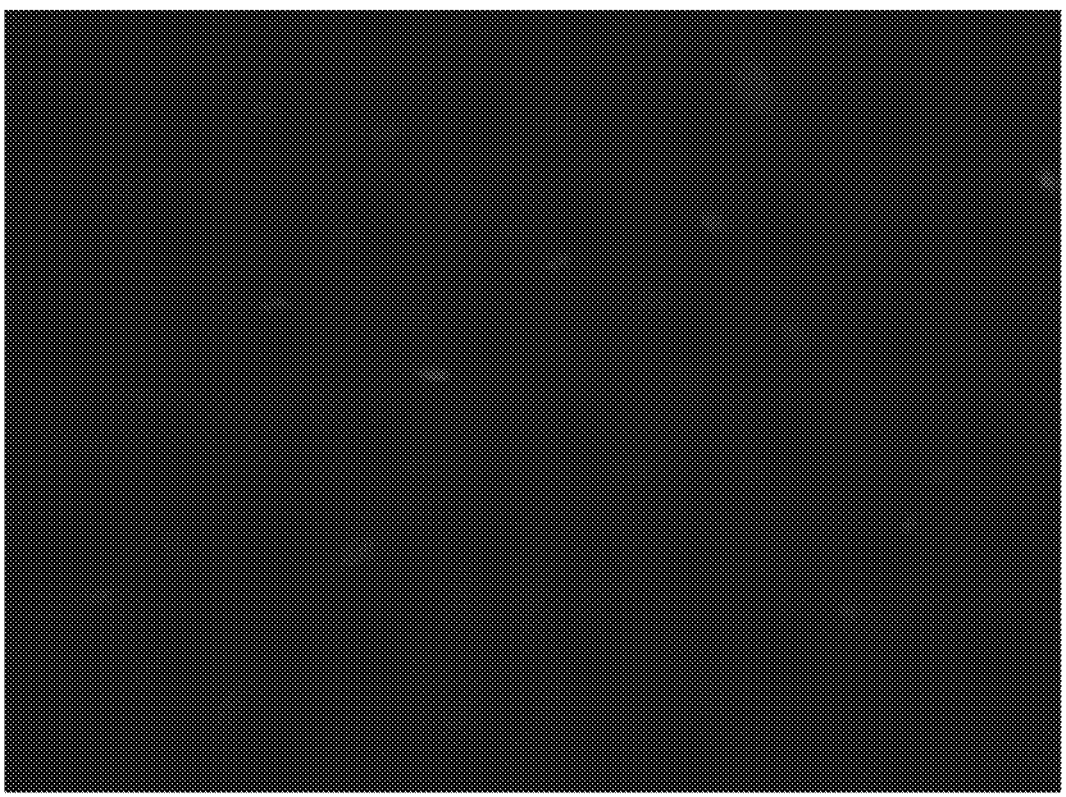
FIG. 24 shows the CFTR-EGFP positive MSCs taken on a fluorescence microscope following seeding the cells on slides, fixing and staining the nuclei with DAPI (blue) at ×20 magnification.
Figure 25:
FIG. 25 shows the CFTR-EGFP positive MSCs taken on a fluorescence microscope following seeding the cells on slides at ×20 magnification.

Fluorescence Images are shown in FIGS. 20 and 21.

Discussion

In this study, modification of EV fractions produced by cells were studied. As indicated by the NTA analysis in the previous study, the mean size of PEGylated exosomes was slightly higher than of PEGylated exosomes, although these experiments could not establish any specific co-relation between the hydrodynamic size difference of PEGylated vs Non-PEGylated EVs. This may be 1) because of the incorporation of PEG molecules onto the surface of the EVs modifying their behaviour in suspension; 2) leaching out of PEGylated EVs from the use of plastic tubes used for storage/incubation; 3) leaching out of EVs from Ultra Centrifuge Tubes during ultracentrifugation washing step after PEGylation is done; 4) precipitation of PEGylated EVs by the use of plastic/silicon pipettes. Additionally, the zeta potential measured using a Litesizer indicated the surface charge of unPEGylated EVs was in the range of −6.65 to −18.6 mV for series readings in which maximum 1000 runs was done by Anton Paar Software until a set algorithm for Phase quality control was reached or average of 1000 runs was considered automatically by the machine, whereas for PEGylated EVs in Series run similar to above for sample 1, 2 and 6 yields maximum mean zeta potential value of −0.40 mV to a minimum of −23.6 mV was observed, although consecutive zeta potential readings were observed to have a visible trend of significantly lower values than the initial readings, suggesting the modification of surface characteristics of PEGylated EVs due to applied voltage and PEGylation of EVs effectively bringing the surface charge of EVs towards a neutral value. This phenomenon may indeed help to explain that the surface modification of the exosomes is reversible which is a possible explanation for the observation that surface modification with low molecular weight PEG did not hinder cellular transmembrane uptake of the exosomes as we had expected to occur.

Another zeta test by replicates of same sample was performed in single run tests although the results were inconclusive, may be because of the storage capacity or PEG interactions with plastic. To further reduce possible interaction of plastic tubes with PEG particles during PEGylation incubation step by using glass vials although the ultracentrifugation step using the plastic ultracentrifuge tubes could not be skipped, nor could the use of plastic/silicon pipettes during transfer of DSPE-PEG or PEGylated EVs. In future, we will modify our experimental techniques accordingly, through the use of glassware vessels and instruments such as pipettes and modification of the EV purification technique post PEGylation by changing to SEC chromatography. The DSPE-PEG was also observed to be possibly degraded when some of these experiments were performed although we observed positive values at the modes in some of the sample indicating that effective PEGylation was possible using more PEG. This is a clear indication that some EVs were PEGylated, as PBS itself wouldn't cause the distribution peak to shift towards positive values and that the presence of PEG molecules on the membrane of exosomes nearly neutralised the surface charge. Furthermore, as exosome samples required an additional ultracentrifugation step to remove excess PEG molecules, the actual particle count after the isolation of exosomes may be higher than the number obtained after the PEGylation procedure.

The hMSCs were also transduced, although with initial setbacks a stable transduction was achievable at about MOI=4 or larger using spin protocol. Fluorescence Images produced from the transduced cells show GFP fluorescence in all transduced cells which is the result of the CFTR-EGFP fusion protein and the EGFP control lentivirus. This is shown in FIGS. 22-25 show GFP positive MSCs taken on a fluorescence microscope following seeding the cells on slides, fixing and staining the nuclei with DAPI (blue). This confirms the presence of cells, not just autofluoresence. Two magnifications are provided showing GFP expression in all cells.

In conclusion, it has been shown that EVs can be PEGylated to impart mucus penetrating abilities without impacting on intracellular trafficking of the EVs—further investigation of PEGylation using refined and specific tools is possible as suggested—and the EVs can be characterized—again this can be further explored for large scale production. Characterization of EVs and proteins from CFTR overexpressed cells for over expression of CFTR protein using RNA, gene and protein analysis will further show effective transduction and proof of concept. The functional transfer of CFTR expression mediated by these exosomes (in comparison to the Negative Controls) will be evaluated in Air Liquid Interface models of CF epithelial cells as this model recapitulates the conditions, inclusive of the mucus barrier, that an inhaled aerosol will encounter once the aerosol droplets deposit in the CF lung. These experiments are expected to show significant improvements over the state of the art viral vector and nanoparticle mediated gene transfer approaches i.e. greater transduction efficiency, functional transfer of CFTR protein and mRNA to virtually all cells in culture and demonstration of functionality of introduced actives in CF epithelial cells by assessment of chloride ion transport in Ussing chamber experiments of transduced cell cultures.

Also, scaling up of EV isolation using high cell density Bioreactor technologies and using more efficient and commercially scalable ways of EV isolation such as Tangential Flow Filtration and Size Exclusion Chromatography may raise the yield of EVs. The use of immortalised stem cells that are transduced with the CFTR overexpression lentivirus to create a master cell bank that is capable of reliably producing the overexpressed recombinant nucleic acids over extended passages is also highly beneficial for commercial scale production of EVs. Further optimization of the PEGylation protocol may neutralize charge of EVs separated from CFTR transduced mesenchymal stem cells without major loss, especially the storage and transfer of DSPE-PEG and PEGylated samples using organic solution safe apparatus.

REFERENCES

Bai, L. et al. (2017) 'Effects of Mesenchymal Stem Cell-Derived Exosomes on Experimental Autoimmune Uveitis', Scientific Reports, 7(1), pp. 1-11.

Beach, A. et al. (2014) 'Exosomes: An overview of biogenesis, composition and role in ovarian cancer', Journal of Ovarian Research. Journal of Ovarian Research, 7(1), pp. 1-10.

Cheng, Y. et al. (2018) 'Effect of pH, temperature and freezing-thawing on quantity changes and cellular uptake of exosomes', Protein & Cell.

Chia, D., Katsiougiannis, S., Kim, Y., Singh, R., and Wong, D. (2016). Saliva exosomes from pancreatic tumor—bearing mice modulate NK cell phenotype and antitumor cytotoxicity. The Faseb Journal, 31(3): 998-1010.

Chia, B., Low, Y., Wang, Q., Li, P. and Gao, Z. (2017). Advances in exosome quantification techniques. Trends in Analytical Chemistry, 0165-9936.

De Toro, J. et al. (2015) 'Emerging roles of exosomes in normal and pathological conditions: New insights for diagnosis and therapeutic applications', Frontiers in Immunology, 6(MAY), pp. 1-12.

Denzer, K. et al. (2000) 'Exosome: from internal vesicle of the multivesicular body to intercellular signalling device.', Journal of cell science, 113 Pt 19(19), pp. 3365-74.

Deregibus, M. C. et al. (2016) 'Charge-based precipitation of extracellular vesicles', International Journal of Molecular Medicine, 38(5), pp. 1359-1366.

Degiorgio, V., Corti, M. and Giglio, M. Light Scattering in Liquids and Macromolecular Solutions. (1979). Plenum Press, New York. See Section II, p. 111 on micelles, p. 125 on vesicles, and p. 139 on microemulsions Gerlach, J., Maguire, C., Krüger, A., Joshi, L., Prina-Mello, A., and Griffin, M. (2017). Urinary nanovesicles captured by lectins or antibodies demonstrate variations in size and surface glycosylation profile. Nanomedicine, 12:11

Hole, P., Sillence, K., Hannell, C., Maguire, C, Roesslein, M., Suarez, G., Capracotta, S., Magdolenova, Z., Horev-Azaria, L., Dybowska, A., Cooke, L., Haase, A., Contal, S., Manø, S., Vennemann, A12., Sauvain, J., Staunton, K., Anguissola, S., Luch, A., Dusinska, M., Korenstein, R., Gutleb, A., Wiemann, M., Prina-Mello, A2., Riediker, M., Wick, P. (2013). Interlaboratory comparison of size measurements on nanoparticles using nanoparticle tracking analysis (NTA). Journal of Nanoparticle Research, 15:2101

Kooijmans S A A, Fliervoet L A L, van der Meel R, Fens M H A M, Heijnen H F G, van Bergen En Henegouwen P M P, Vader P, Schiffelers R M. PEGylated and targeted extracellular vesicles display enhanced cell specificity and circulation time. J Control Release. 2016 Feb. 28; 224:77-85

Lai, R. C. et al. (2013) 'Exosomes for drug delivery—a novel application for the mesenchymal stem cell', Biotechnology Advances, 31(5), pp. 543-551.

Lankford, K. L. et al. (2018) 'Intravenously delivered mesenchymal stem cell-derived exosomes target M2-type macrophages in the injured spinal cord', PLoS ONE, 13(1), pp. 7-11.

Lin, J. et al. (2015) 'Exosomes: Novel Biomarkers for Clinical Diagnosis', The Scientific World Journal, 2015, pp. 1-8.

Lou, G. et al. (2017) 'Mesenchymal stem cell-derived exosomes as a new therapeutic strategy for liver diseases', Experimental & molecular medicine. Nature Publishing Group, 49(6), p. e346.

Li, C., Huang, Q., Zhang, G., Yang, Z., Lu, W., Zhang, R., Tian, M., Li, L. and Liang, D. (2009). Influence of anchoring ligands and particle size on the colloidal stability and in vivo bio-distribution of polyethylene glycol-coated gold nanoparticles in tumor-xenografted mice. Biomaterials, 30:10

Maguire, P., Parsons, M., McParland, D., Szklanna, P., Guang, M., O'Connell, K., O'Connor, H., McGuigan, C., Áinle, F. and McCann, A. (2017). A Protocol for Improved Precision and Increased Confidence in Nanoparticle Tracking Analysis Concentration Measurements between 50 and 120 nm in Biological Fluids. Frontiers in Cardiovascular Medicine, 4:68

Nag, O., and Awasthi, V., (2013). Surface Engineering of Liposomes for Stealth Behavior. Pharmaceutics, 5(4): 542-569.

Nag, O. K. et al. (2013) 'Post-modification of preformed liposomes with novel non-phospholipid poly(ethylene glycol)-conjugated hexadecylcarbamoylmethyl hexadecanoic acid for enhanced circulation persistence in vivo', International journal of pharmaceutics, 446(0), pp. 119-129.

Niu, Z. et al. (2017) 'Polymer-based precipitation preserves biological activities of extracellular vesicles from an endometrial cell line', PLoS ONE, 12(10), pp. 1-21.

O'Neill C P, Gilligan K E, Dwyer R M. Role of Extracellular Vesicles (EVs) in Cell Stress Response and Resistance to Cancer Therapy. Cancers (Basel). 2019 Jan. 24; 11(2).

Sato, Y. T. et al. (2016) 'Engineering hybrid exosomes by membrane fusion with liposomes', Scientific Reports. Nature Publishing Group, 6(February), pp. 1-11.

Stahl P D, Raposo G. Extracellular Vesicles: Exosomes and Microvesicles, Integrators of Homeostasis. Physiology (Bethesda). 2019 May 1; 34(3):169-177.

Sugama, S. et al. (2017) 'NHS Public Access', pp. 39-46.

Suk, J. S. et al. (2017) 'NHS Public Access', 99, pp. 28-51.

Théry, C., Amigorena, S., Raposo, G. and Clayton, A. (2006). Isolation and characterization of exosomes from cell culture supernatants and biological fluids. Current Protocols in Cell Biology, 3: 3.22

The invention claimed is:

1. An aerosolizable composition comprising exosomes from mesenchymal stem cells (MSCs), wherein the exosomes have a surface coating comprising a hydrophilic polymer that comprises polyethylene glycol (PEG), wherein the exosomes carry a cargo comprising a microRNA (miR), an anti-miR, an mRNA, a long non-coding RNA, a circular RNA, a small interfering RNA, a short hairpin RNA, a piwi-interacting RNA, a CRISPR RNA sequence, a protein, a cytokine, or a lipid, wherein the polymer has a molecular weight of less than 5 kDa, and wherein the surface coating covers at least 65% of the exosomes' surface and substantially neutralises the surface charge of the exosomes.

2. The composition according to claim 1, wherein the hydrophilic polymer comprises 1,2-Distearoyl-sn-glycero-3-phosphoethanolamine-PEG (DSPE-PEG).

3. The composition according to claim 1, wherein the hydrophilic polymer has a molecular weight of less than 3 kDa.

4. The composition according to claim 1, wherein the cargo comprises a microRNA (miR).

5. The composition according to claim 4, wherein the miR is selected from miR-125b-5p, miR-125b-1-3p, miR-513a-5p, and miR-17.

6. The composition according to claim 1, wherein the cargo comprises an mRNA or its translated protein.

7. The composition according to claim 6, wherein the cargo comprises an mRNA, wherein the mRNA is a modified cystic fibrosis transmembrane conductance regulator (CFTR) mRNA.

8. The composition according to claim 1, wherein the composition is an aqueous suspension or colloid.

9. The composition according to claim 1, wherein the surface charge of the exosomes is −8 mV to 0 mV.

* * * * *